United States Patent
Pero et al.

(10) Patent No.: US 9,624,208 B2
(45) Date of Patent: Apr. 18, 2017

(54) BENZOXAZOLINONE COMPOUNDS WITH SELECTIVE ACTIVITY IN VOLTAGE-GATED SODIUM CHANNELS

(71) Applicant: Merck Sharp & Dohme Corp., Rahway, NJ (US)

(72) Inventors: Joseph E. Pero, Harleysville, PA (US); Hannah D. G. F. Lehman, Boyertown, PA (US); Michael J. Kelly, III, Paoli, PA (US); Lianyun Zhao, Ambler, PA (US); Michael A. Rossi, Middleton, DE (US); Dansu Li, Warrington, PA (US); Kevin F. Gilbert, Barto, PA (US); Scott Wolkenberg, Wyndmoor, PA (US); James Mulhearn, Elkins Park, PA (US); Mark E. Layton, Harleysville, PA (US); Pablo de Leon, Baltimore, MD (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 14/437,315

(22) PCT Filed: Oct. 23, 2013

(86) PCT No.: PCT/US2013/066357
§ 371 (c)(1),
(2) Date: Apr. 21, 2015

(87) PCT Pub. No.: WO2014/066490
PCT Pub. Date: May 1, 2014

(65) Prior Publication Data
US 2015/0252034 A1    Sep. 10, 2015

Related U.S. Application Data

(60) Provisional application No. 61/719,040, filed on Oct. 26, 2012.

(51) Int. Cl.
C07D 413/12    (2006.01)
C07D 413/14    (2006.01)
C07D 263/58    (2006.01)
A61K 31/44    (2006.01)

(52) U.S. Cl.
CPC ............ C07D 413/14 (2013.01); A61K 31/44 (2013.01); C07D 263/58 (2013.01); C07D 413/12 (2013.01)

(58) Field of Classification Search
CPC .................................................... C07D 413/12
USPC ........................................ 546/271.7; 514/338
See application file for complete search history.

(56) References Cited

U.S. PATENT DOCUMENTS

| | | |
|---|---|---|
| 2009/0023740 A1 | 1/2009 | Fulp et al. |
| 2009/0312328 A1 | 12/2009 | Kubota et al. |
| 2011/0082117 A1 | 4/2011 | Martinborough et al. |
| 2012/0122849 A1 | 5/2012 | Salituro et al. |

*Primary Examiner* — Patricia L Morris
(74) *Attorney, Agent, or Firm* — H. Eric Fischer; John C. Todaro

(57) ABSTRACT

Disclosed are compounds of Formula A: Formula A, or a salt thereof, wherein "Het", $R^a$, and $R^b$ are defined herein, which have properties for blocking $Na_v$ 1.7 ion channels found in peripheral and sympathetic neurons. Also described are pharmaceutical formulations comprising the compounds of Formula A or their salts, and methods of treating neuropathic pain disorders using the same.

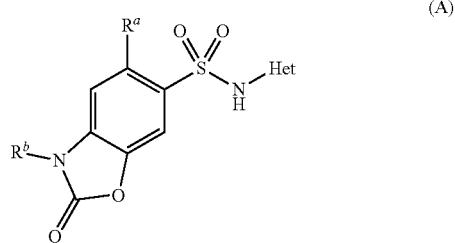

(A)

5 Claims, No Drawings

BENZOXAZOLINONE COMPOUNDS WITH SELECTIVE ACTIVITY IN VOLTAGE-GATED SODIUM CHANNELS

BACKGROUND

Voltage-gated sodium channels play a central role in initiating and propagating action potentials in electrically excitable cells, see for example Yu and Catterall, Genome Biology 4:207 (2003) and references therein. Voltage-gated sodium channels are multimeric complexes characterized by an Alpha-subunit which encompasses an ion-conducting aqueous pore, the site of the essential features of the channel, and at least one Beta-subunit that modifies the kinetics and voltage-dependence of the channel gating. These structures are ubiquitous in the central and peripheral nervous system and are believed to play a central role in initiation and propagation of electrical signals in the nervous system.

It has been shown in human patients as well as in animal models of neuropathic pain that damage to primary afferent sensory neurons may lead to neuroma formation and spontaneous activity, as well as evoked activity in response to normally innocuous stimuli. [Carter, G. T. and Galer, B. S., Advances in the Management of Neuropathic Pain, Physical Medicine and Rehabilitation Clinics of North America, 2001, 12(2): pp 447 to 459]. Injuries of the peripheral nervous system often result in neuropathic pain persisting long after an initial injury resolves. Examples of neuropathic pain include, for example, post herpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. The ectopic activity of normally silent sensory neurons is thought to contribute to the generation and maintenance of neuropathic pain, which is generally assumed to be associated with an increase in sodium channel activity in the injured nerve. [Baker, M. D. and Wood, J. N., Involvement of Na Channels in Pain Pathways, TRENDS is Pharmacological Sciences, 2001, 22(1): pp 27 to 31.

Nine different Alpha-subunits have been identified and characterized in mammalian voltage-gated sodium channels. These structures are designated $Na_v$ 1.X sodium channels (X=1 to 9) in accordance with currently accepted nomenclature practice, designating their ion selectivity (Na), the physiological regulator ('v', potential, i.e. voltage), and the gene subfamily encoding them (1.X), with the number designator X (1 to 9) being assigned for the alpha subunit present in the structure (see Aoldin et al., Neuron, 28:365-368 (2000)). $Na_v$1.7 voltage-gated sodium ion channels (herein designated "Nav 1.7 channels" in some instances for convenience) are expressed primarily in sensory and sympathetic neurons. They are believed to play a role in nociception and in particular have a central role in inflammatory pain perception, (see Wood et al. J. Neurobiol. 61: pp 55-71 (2004) and Nassar et al., *Proc. Nat. Acad. Sci.* 101(34): pp 12706-12711 (2004)). Accordingly it is believed that identification and administration of agents which interact to block $Na_v$ 1.7 voltage-gated sodium ion channels represents a rational approach for providing treatment or therapy for nociception disorders stemming from dysfunction of $Na_v$1.7 voltage-gated sodium ion channels (see Clare et al., Drug Discovery Today, 5: pp 506-520 (2000)).

Because voltage gated sodium ion channels are ubiquitous in the central and peripheral nervous system and conservation of structures in the various Alpha-subunits characterizing voltage-gated sodium ion channels implicates the potential for producing serious side effects when utilizing therapeutic agents that target blocking voltage-gated sodium ion channels, therapeutic agents suitable for use in addressing nociception disorders require specificity in their action, for example, low activity blocking $Na_v$1.5 sodium ion channels (which channels are thought to be important in regulation of cardiac function) while displaying potent activity in blocking $Na_v$1.7 sodium ion channels (which is believed to be central in providing therapy for inflammatory nociception and disorders arising from dysfunctional $Na_v$ 1.7 sodium ion channels). It will be appreciated that in general activity selectively targeting $Na_v$ 1.7 sodium ion channels while not significantly effecting other $Na_v$1.X channels would be advantageous in developing therapeutics for such disorders.

Published international application no. WO09/012242 (the '242 publication) describes compounds having the structure of Formula PA:

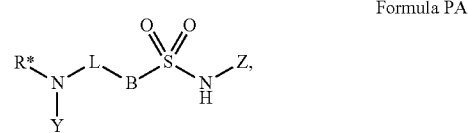

Formula PA wherein R* is a proton, alkyl or heteroalkyl, aryl, or heteroaryl group, Y is an aryl group or a 5 or 6 member-ring heteroaryl group, L is either not present or is a cyclic structure containing nitrogen or substituted with nitrogen, B is a cycloalkyl, heterocycloalkyl, aryl or heteroaryl moiety, and Z is a five or six-member ring heteroaryl moiety, and optionally R*, N, and Y form a cyclic structure which may be a heteroaryl moiety, for example, the compound of Formula PB:

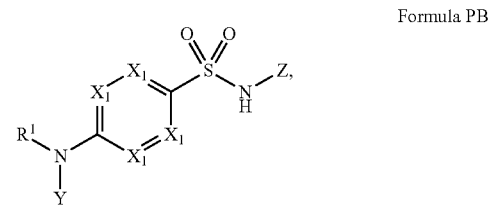

Formula PB wherein $R^1$, Y, and Z are as defined for the compound of Formula PA, and wherein each $X_1$ is independently N or unsaturated carbon optionally substituted with hydrogen, halogen, CN, OH, alkyl or substituted alkyl. These compounds are said to have activity as Nav 1.7 channel and Nav 1.3 channel blockers but are not shown to have selectivity as specific Nav 1.7 channel blockers.

Compounds having $Na_v$1.7 activity described in published international applications WO 2010/079443 (the '443 publication) and related WO2012/004706, WO2012/004714, WO2012/064984, WO2013/064983, and WO2013/064984 have the structure of Formula PC:

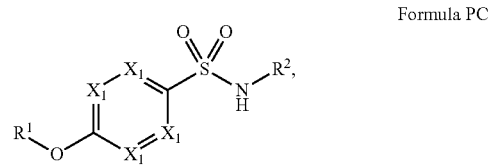

Formula PC wherein $X_1$ is N or C—$R^3$ ($R^3$ is a wide number of substituents including halogen), $R^1$ is a cycloalkyl, aryl or heteroaryl moiety and $R^2$ is a heteroaryl moiety.

Examples of these compounds include compounds of Formula PD:

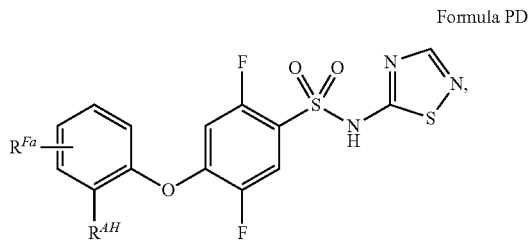

Formula PD where $R^{AH}$ is an aryl or heteroaryl moiety and $R^{Fa}$ is one or more of a wide variety of substituents, for example the hetero-substituted aryl compounds of Formula PE and Formula PF:

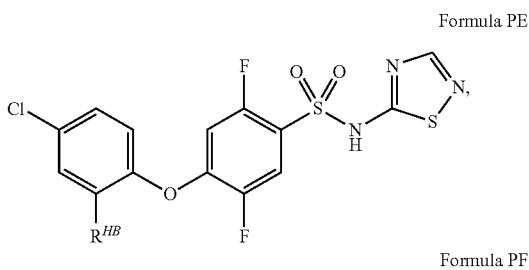

Formula PE

Formula PF wherein $R^{HB}$ is a heterobicyclo moiety.

An additional example of these compounds are the heterocycloalkyl-substituted compounds of Formula PG:

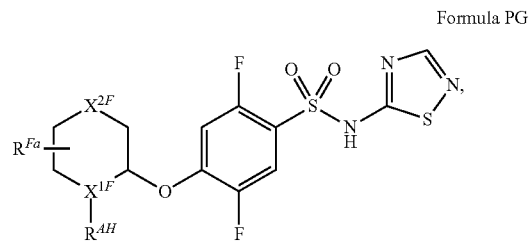

Formula PG wherein at least one of $X^{1F}$ and $X^{2F}$ are a heteroatom and the other is either a substituted carbon or CH, $R^{AH}$ is an aryl or heteroaryl moiety and $R^{Fa}$ is one or more of a wide variety of substituents. These foregoing compounds are said to have affinity for Nav 1.7 sodium channels and modest or low affinity for $Na_v1.5$ sodium channels, but do not offer much structural diversity.

Recently, compounds described in published international applications WO 2013/025883 WO2013/086229, and WO2013/134518, having the structure of Formula PH:

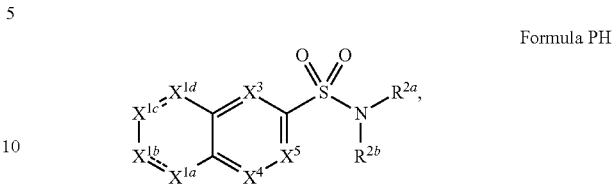

Formula PH wherein one of $R^{2a}$ or $R^{2b}$ is an aryl or heteroaryl moiety and the other is —H or alkyl, $X^3$ to $X^5$ are =N— or =CR$^5$— (where $R^5$ is a wide range of compatible substituents), $X^{1a-1d}$ are =N—, —NR$^4$— (where $R^4$ is H, alkyl, or a wide variety of other substituents compatible with N), or =CR$^3$— ($R^3$ is a wide number of substituents, including, H, alkyl, aryl and heteroaryl) and wherein $X^{1c}$ may be absent, in which case $X^{1b}$ is CH. These compounds claim activity for Nav1.7 sodium ion channels and selectivity over Nav1.5 channels.

There remains a need for additional compounds having high potency and selectivity for $Na_v$ 1.7 sodium channels, have acceptable bioavailability properties, and that offer a variety of cores to facilitate rational development of therapeutic agents for use as selective $Na_v$ 1.7 sodium ion channel blockers.

SUMMARY OF THE INVENTION

In one aspect, the invention provides compounds having selective activity as $Na_v$ 1.7 sodium ion channel blockers which have the structure of Formula A:

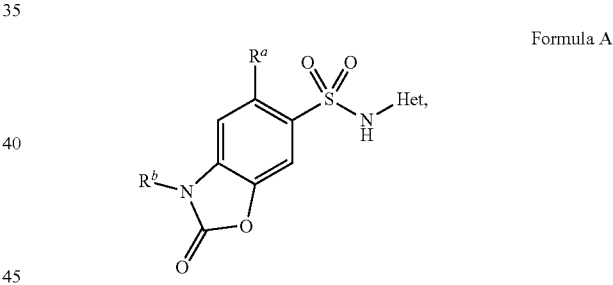

Formula A or a salt thereof,
wherein:
$R^a$ is —H, $C_{1-6}$ alkyl, $C_{1-6}$ alkoxy, —CN or halogen, and when selected to be a halogen is preferably —F;
"Het" is a heteroaryl moiety as defined herein, preferably a 6 member heteroaryl moiety comprising up to three heteroatoms selected from N, S, and O, bonded through any ring-atom of the aryl moiety available for bonding and optionally substituted with one or more "ring-system substitutes"; and
$R^b$ is: (i) $C_{1-8}$ linear-alkyl moiety; (ii) $C_{1-8}$-branched-alkyl moiety; (iii) $C_{3-8}$-cyclic-alkyl moiety; (iv) $C_{6-10}$-aryl moiety; (v) $C_{5-12}$-polycyclic-alkyl moiety; (vi) $C_{8-12}$-polycyclic-aryl-alkyl moiety; (viii) heterocycloalkyl-aryl-monocyclic or polycyclic moiety having up to 10 carbon atoms and up two three heteroatoms selected from N, O, or S; or (vii) heteroaryl-alkyl monocyclic or polycyclic moiety having up to 10 carbon atoms and up to three heteroatoms selected from N, O, or S, wherein any of said $R^b$ moieties is optionally substituted with one or more of: (1) monocyclic or polycyclic $C_{4-9}$ heteroaryl-moiety; (2) monocyclic or polycyclic $C_{3-10}$- alkyl-moiety; or (3) monocyclic or polycyclic $C_{6-10}$-aryl moiety, wherein said monocyclic or polycyclic moieties are optionally substituted with one or more "ring-system" substituents as that term is defined herein.

In some embodiments, where $R^b$ is selected to be a linear alkyl substituted with an aryl moiety, the aryl moiety optionally comprising one or more "ring-system substituents", and when present, preferably the "ring-system substituent" is a $C_{4-10}$-heterocycloalkyl moiety comprising up to three hetero atoms.

In some embodiments, preferably "Het" is a pyridin-2-yl moiety which optionally has one or more hydrogens residing at the carbon 4, 5, or 6 position on the ring substituented with a halogen and when so substituted, preferably the halogen is —F or —Cl.

In some embodiments, $R^b$ is preferably —$(C(R^{bd})_2)_{1-3}$—$R^{be}$—, wherein $R^{bd}$ is independently for each occurrence: —H or $C_{1-6}$-alkyl; and $R^{be}$ is an aryl moiety, optionally having one or more ring-system substituents, as defined herein. In some embodiments where $R^{bd}$ is any aryl moiety having one or more ring-system substituents, preferably ring-system substituents are independently for each occurrence: (i) heterocyclenyl; (ii) heterocyclyl; (iii) heteropyrazinyl or (iv) aminoalkyl.

In some embodiments wherein $R^{be}$ is aryl substituted with a heterocyclenyl moiety, $R^b$ is preferably a moiety of Formula $R^{b1}$:

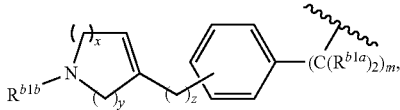

Formula $R^{b1}$ wherein: "m" is an integer 1 to 4; $R^{b1a}$ and $R^{b1b}$ are independently for each occurrence: —H or $C_{1-4}$-alkyl; "x" and "y" are independently 1 or 2 and "z" is 0, 1, 2 or 3.

In some embodiments wherein $R^{be}$ is aryl substituted with a heterocyclyl or heteropyrazinyl moiety, $R^b$ is preferably a moiety of Formula $R^{b2}$:

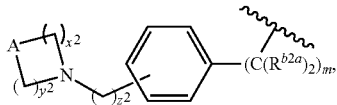

Formula $R^{b2}$ wherein: "m" is an integer 1 to 4; $R^{b2a}$ is independently for each occurrence: —H or $C_{1-4}$-alkyl; "x²" and "y²" are independently an integer of 1 to 3; "z²" is an integer of 0 to 4; and "A" is: (i) —($CH_2$)—; (ii) —($NR^{b2g}$)—, wherein "$R^{b2g}$" is —H or —$C_{1-6}$-alkyl; or (iii) —O—.

In some embodiments $R^b$ is preferably a moiety of Formula $R^{b3}$:

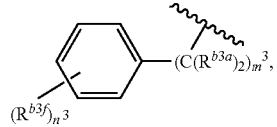

Formula $R^{b3}$ wherein: "m³" is an integer 1 to 4; "n³" is 1, 2, or 3; $R^{b3a}$ is independently for each occurrence: —H or $C_{1-4}$-alkyl; and $R^{b3f}$ is independently for each occurrence: (i) halogen; or (ii) —$C_{1-6}$-alkyl which is optionally substituted with: (i) —(N($R^{b3g}$)$_2$), wherein "$R^{b3g}$" is independently —H or $C_{1-6}$-alkyl, or both of "$R^{b3g}$" taken together with the nitrogen to which they are bonded form a cycloamine of up to 6 carbon atoms; or (ii) a moiety of Formula $R^{b3h}$:

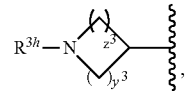

Formula $R^{b3h}$ wherein $R^{3h}$ is —H or $C_{1-6}$-alkyl, and independently, $y^3$ and $z^3$ are integers of 0 to 5 wherein the sum of $y^3+z^3$ is 2 to 5.

In some embodiments $R^b$ is preferably a moiety of Formula $R^{b4}$:

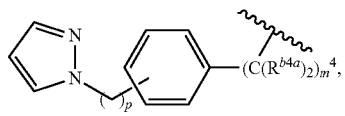

Formula $R^{b4}$ wherein: "m⁴" is an integer 1 to 4; $R^{b4a}$ is independently for each occurrence —H or $C_{1-4}$-alkyl; and "p" is an integer of 1 to 3.

In some embodiments it is preferred for $R^b$ to be:
(i) a moiety of Formula AI:

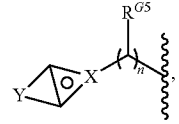

Formula AI wherein:
$R^{G5}$ is, independently for each occurrence, —H or a linear or branched $C_{1-5}$-alkyl moiety; "n" is an integer of 0 to 2;
"X", together with the bridging carbons to which it is bonded forms an aromatic ring or a $C_{5-8}$-heteroaromatic ring comprising one or more heteroatoms which are independently N, O or S, wherein one or more hydrogens on said aromatic or heteroaromatic ring are optionally substituted by a moiety which is independently for each occurrence:
(a) —N(R*)$_2$, wherein R* is —H or $C_{1-4}$-alkyl; (b) —$C_{1-6}$-alkyl, which is optionally substituted on any carbon thereof with one or more —F; (c) —OH; (d) —O—$C_{1-6}$-alkyl optionally substituted on any carbon thereof with one or more —F; (e) CN; (f) halogen; or (g) heteroaryl; and
"Y" together with the bridging carbon atoms to which it is bonded forms a a cycloalkyl moiety of up to 8 carbon atoms or a heterocycloalkyl moiety of up to 8 carbon atoms and one or more heteroatoms which are independently N, O or S, and which is optionally substituted by:
(a) —N(R*)$_2$, wherein R* is —H or $C_{1-4}$-alkyl; (b) —$C_{1-6}$-alkyl, which is optionally substituted on any carbon thereof with one or more —F; (c) —OH; (d) —O—$C_{1-6}$-alkyl optionally substituted on any carbon thereof with one or more —F; (e) CN; (f) halogen; or (g) heteroaryl;

(ii) a moiety of Formula AII:

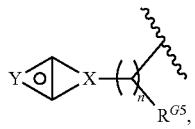

Formula AII wherein:

R$^{G5}$ is independently for each occurrence, —H or a linear or branched C$_{1-5}$-alkyl moiety;

"n" is an integer of 0 to 2;

"X", together with the bridging carbon atoms to which it is bonded forms an optionally-substituted cycloalkyl moiety of up to 8 carbon atoms or a heterocycloalkyl moiety of up to 8 carbon atoms and one or more heteroatoms which are independently N, O or S, and which is optionally substituted by:

(a) —N(R*)$_2$, wherein R* is —H or C$_{1-4}$-alkyl; (b) —C$_{1-6}$-alkyl, which is optionally substituted on any carbon thereof with one or more —F; (c) —OH; (d) —O—C$_{1-6}$-alkyl optionally substituted on any carbon thereof with one or more —F; (e) CN; (f) halogen; or (g) heteroaryl; and "Y", together with the bridging carbons to which it is bonded forms an aromatic ring or a C$_{5-8}$-heteroaromatic ring comprising one or more heteroatoms which are independently N, O or S, wherein one or more hydrogens on said aromatic or heteroaromatic ring are optionally substituted by a moiety which is independently for each occurrence:

a) —N(R*)$_2$, wherein R* is —H or C$_{1-4}$-alkyl; (b) —C$_{1-6}$-alkyl, which is optionally substituted on any carbon thereof with one or more —F; (c) —OH; (d) —O—C$_{1-6}$-alkyl optionally substituted on any carbon thereof with one or more —F; (e) CN; (f) halogen; or (g) heteroaryl; or (iii) a moiety of Formula AIII:

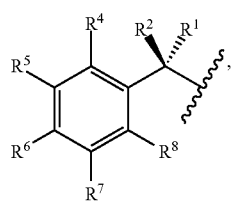

Formula AIII wherein:

R$^1$ and R$^2$ are independently: (i) —H; (ii) C$_{1-8}$ alkyl, preferably methyl, ethyl, propyl, or cyclopropyl, more preferably methyl or cyclopropyl; (iii) C$_{1-4}$ alkenyl, preferably —CH$_2$—CH=CH$_2$; or (iv) C$_{5-8}$-aryl or a 5 to 8-member heteroaryl moiety comprising 1 or more heteroatoms which are independently nitrogen, sulfur, or oxygen, and when a five-member heteroaryl moiety, is preferably oxazole which is optionally substituted;

R$^4$, R$^5$, and R$^6$ are independently:

(i) —H;

(ii) halogen;

(iii) C$_{1-8}$-alkyl, C$_{2-8}$ alkenyl, or C$_{2-6}$ alkynyl, as these moieties are defined herein, which substituents may optionally be substituted by one or more moieties which are:

(a) halogen, preferably fluorine;

(b) hydroxyl;

(c) (R$^{aa}$)$_2$N-(J)-, wherein R$^{aa}$ is: (1) independently for each occurrence: —H; —SO$_2$C$_{1-8}$-alkyl; —SO$_2$-aryl; —(O=C)C$_{1-8}$-alkyl; C$_{1-6}$-linear alkyl; or C$_{3-6}$-cycloalkyl, and when R$^{aa}$ is selected to be an alkyl moiety it may be optionally substituted with one or more fluorine substituents; or (2) both R$^{aa}$ together with the nitrogen atom to which they are bonded form a 4 to 7 member heterocycloalkyl moiety, and wherein "J" is a moiety of the structure:

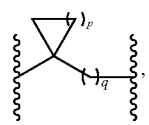

wherein "p" is an integer of 1 to 4 and "q" is an integer of 0 to 5;

(d) —N(R$^{ab}$)$_2$, wherein R$^{ab}$ is: (1) independently for each occurrence: —H; —SO$_2$C$_{1-8}$-alkyl; —SO$_2$-aryl; —(O=C)C$_{1-8}$-alkyl; C$_{1-6}$-linear alkyl; or C$_{3-6}$-cycloalkyl and is optionally bonded to the ring through —S(O$_2$)— or —C(O)— moiety; or (2) both R$^{aa}$ together with the nitrogen atom to which they are bonded form a 4 to 8 member heterocycloalkyl moiety or heterocycloalkenyl moiety which is optionally substituted on one or more carbon atoms, independently, by —OH or halogen;

(e) C$_{1-6}$-alkoxy;

(iv) a moiety of the formula

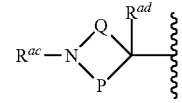

wherein:

R$^{ac}$ is: C$_{1-6}$-alkyl; R$^{ae}$—SO$_2$—, where R$^{ae}$ is -aryl, heteroaryl, or -alkyl; R$^{af}$—CO—, where R$^{af}$ is -aryl, heteroaryl, or -alkyl; or —H;

R$^{ad}$ is: C$_{1-6}$-alkyl; C$_{1-6}$-alkoxy; —OH; —CN; —F; or —H;

"P" and "Q" are independently:

(a) a direct bond;

(b) C$_{1-4}$ alkyl or C$_{1-4}$ alkenyl, and when selected to be alkyl or alkenyl may optionally be substituted by one or more moieties which are independently: (1) halogen, preferably fluorine; (2) —OH; (3) C$_{1-6}$-alkoxy; (4) —CN; or (5) a moiety of the formula —(CH$_2$)$_{1-4}$— which is bonded between a carbon atom in the "P" portion of the heterocycle and a carbon atom in the "Q" portion of the heterocycle forming thereby a bicyclo structure; and R$^7$, and R$^8$ are independently: —H; C$_{1-4}$-alkyl; C$_{1-6}$-alkoxy; C$_{1-6}$—SO$_2$—; or halogen, and when selected to be a halogen, preferably the halogen is chlorine.

In one aspect the invention provides a pharmaceutical composition comprising at least one compound of Formula A and at least one pharmaceutically acceptable excipient adapted for administration to a patient via oral, intravenous, subcutaneous, transcutaneous, intramuscular, intradermal, transmucosal, or intramucosal routes of administration.

In one aspect the invention provides a pharmaceutical composition comprising a pharmaceutical carrier, an effective amount of at least one compound of Formula A or a salt thereof, and an effective amount of at least one other pharmaceutically active ingredient which is: (i) an opiate agonist or antagonist; (ii) a calcium channel antagonist; (iii) an NMDA receptor agonist or antagonist; (iv) a COX-2 selective inhibitor; or (v) an NSAID (non-steroidal anti-inflammatory drug).

In one aspect the invention provides a method of treatment, management, alleviation or amelioration of conditions or disease states which may be treated, managed, alleviated or ameliorated by specific blocking of Nav 1.7 channel activity, the method comprising administering to a patient in need thereof a composition comprising at least one compound of Formula A in an amount providing a serum level of at least one said compound which sufficient to effect said treatment, management, alleviation or amelioration of the condition or disease state. Preferably the condition to be treated, managed, alleviated or ameliorated is a chronic pain disorder

DETAILED DESCRIPTION OF THE INVENTION

As mentioned above, the invention provides compounds having selective activity as $Na_v$ 1.7 sodium ion channel blockers which have the structure of Formula A:

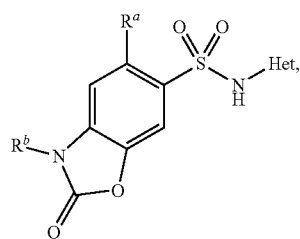

Formula A or a salt thereof, where $R^a$, $R^b$, and "Het" are defined herein.

Compounds of the invention comprising the core structure of Formula A, as defined herein, surprisingly have potent activity for blocking Nav 1.7 channels with high specificity when evaluated using the assay assay techniques, described in more detail herein, and are believed to provide advantageous PK properties in vivo. Accordingly, compounds of the invention and compounds comprising formulations of the invention are believed to be useful in providing treatment, management, alleviation or amelioration of conditions or disease states which may be treated, managed, alleviated or ameliorated by specific blocking of Nav 1.7 channel activity in mammals. Examples of disease states which may be desirably affected using such therapy include, but are not limited to, chronic, visceral, inflammatory or neuropathic pain.

In some embodiments compounds of the invention have the structure of Formula AIV

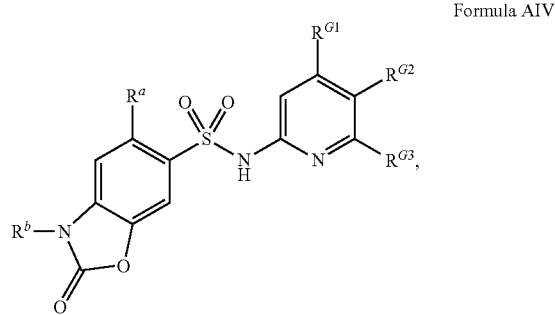

Formula AIV or a salt thereof, wherein, $R^a$ and $R^b$ are defined above, one of $R^{G1}$ to $R^{G3}$ is —F or —Cl and the other two are —H.

With reference to Formula AIV, in some embodiments where one of $R^{G1}$ to $R^{G3}$ is —F or —Cl and the other two are —H: preferably $R^a$ is —H, $C_{1-6}$ alkyl, $C_{1-6}$ alkoxy, —CN or halogen, and when selected to be a halogen is preferably —F; and $R^b$ is (i) a $C_{1-8}$ alkyl or arylalkyl-, either of which are optionally substituted with a halogen or an amino moiety; (ii) a benzyl moiety optionally substituted with a "ring-system substituent" as defined herein, and wherein the methylene carbon of said benzyl moiety may optionally be substituted as defined for alkyl substituents herein; (iii) a heteroaryl-alkyl-moiety, optionally substituted with a "ring-system substituent" as defined herein; or (iv) a heteroalkylaryl-moiety which is optionally substituted as described herein.

In some embodiments, compounds of the invention preferably have the structure of Formula B:

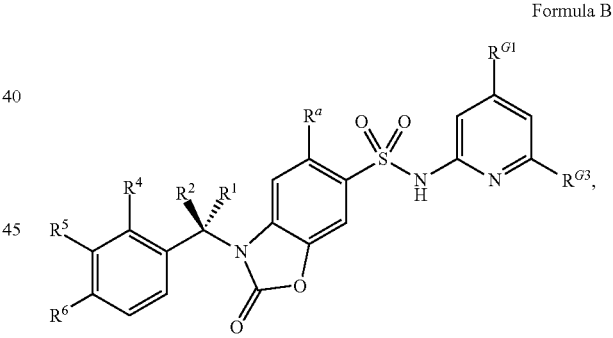

Formula B or a salt thereof,
wherein:
one of $R^1$ and $R^2$ is —H and the other is:
(i) —H;
(ii) —$C_{1-8}$ alkyl, preferably methyl, ethyl, propyl, or cyclopropyl, more preferably methyl or cyclopropyl, wherein the alkyl moiety is optionally substituted with a $C_{3-6}$ cycloalkyl moiety, preferably cyclopropyl;
(iii) —$C_{1-4}$ alkenyl, preferably —$CH_2$—CH=$CH_2$;
(iv) -aryl; or
(v) 5 to 8-member heteroaryl moiety comprising one or more heteroatoms which are independently nitrogen, sulfur, or oxygen, and when a five-member heteroaryl moiety, is preferably oxazole which is optionally substituted;
$R^a$ is —H, $C_{1-6}$ alkyl, $C_{1-6}$ alkoxy, —CN or halogen, and when selected to be a halogen is preferably —F;

one of $R^{G1}$ and $R^{G3}$ is —H and the other is —H or Halogen, and when halogen, is preferably —F or —Cl; and $R^4$, $R^5$, and $R^6$ are independently:
(i) —H;
(ii) halogen, and when halogen, preferably —Br;
(iii) linear $C_{1-8}$-alkyl, $C_{3-8}$-branched alkyl, $C_{3-8}$-cycloalkyl, $C_{2-8}$ alkenyl, or $C_{2-6}$ alkynyl, as these moieties are defined herein, which substituents may optionally be substituted by one or more moieties which are:
(a) halogen, preferably fluorine;
(b) hydroxyl;
(c) $C_{3-6}$-cycloalkyl substituted with an amino-moiety;
(d) Heteroarylalkyl;
(e) $(R^{aa})_2N$-(J)-, wherein $R^{aa}$ is:
(1) independently for each occurrence —H or is $C_{1-6}$-linear alkyl or $C_{3-6}$-cycloalkyl; or
(2) both $R^{aa}$ together with the nitrogen atom to which they are bonded from a 4 to 6 member heterocycloalkyl moiety, and wherein "J" is a moiety of the structure:

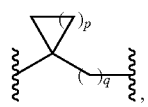

wherein "p" is an integer of 1 to 4 and "q" is an integer of 0 to 5;
(f) —$N(R^{ab})_2$, wherein $R^{ab}$ is: (1) independently for each occurrence —H or is $C_{1-6}$-linear alkyl or is $C_{3-6}$-cycloalkyl, which is optionally bonded to the ring through —$S(O_2)$— or —C(O)— moiety; or (2) both $R^{aa}$ together with the nitrogen atom to which they are bonded form a 4 to 8 member heterocycloalkyl moiety or heterocycloakenyl moiety which is optionally substituted on one or more carbon atoms, independently, by —OH or halogen;
(iv) a moiety of the formula:

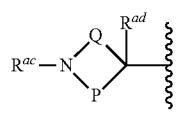

wherein:
$R^{ac}$ is: $C_{1-6}$-alkyl; $R^{ae}$—$SO_2$—, where $R^{ae}$ is -aryl, heteroaryl, or -alkyl; $R^{af}$—CO—, where $R^{af}$ is -aryl, heteroaryl, or -alkyl; or —H;
$R^{ad}$ is: $C_{1-6}$-alkyl-; —OH; $C_{1-6}$-alkyl-O—; —F; —CN; or —H;
"P" and "Q" are independently:
(a) a direct bond;
(b) $C_{1-4}$ alkyl or $C_{2-4}$ alkenyl, and when selected to be alkyl or alkenyl may optionally be substituted by one or more moieties which are independently: (1) halogen, preferably fluorine; (2) —OH; (3) $C_{1-6}$-alkoxy; (4) —CN; or (5) a moiety of the formula —$(CH_2)_{1-4}$— which is bonded between a carbon atom in the "P" portion of the heterocycle and a carbon atom in the "Q" portion of the heterocycle forming thereby a bicyclo structure.

In some embodiments, compounds of the invention preferably have the structure of Formula C:

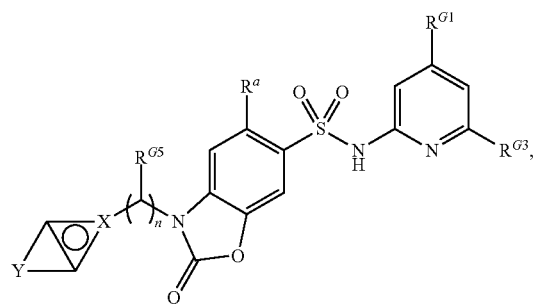

Formula C or a salt thereof,
wherein:
"n" is an integer of 1 to 2;
$R^a$ is —H, $C_{1-6}$ alkyl, $C_{1-6}$ alkoxy, —CN or halogen, and when selected to be a halogen is preferably —F;
One of $R^{G1}$ and $R^{G3}$ is —H and the other is —H or Halogen, and when halogen, is preferably —F or —Cl;
$R^{G5}$ is, independently for each occurrence, —H or a linear or branched $C_{1-5}$-alkyl moiety;
"X", together with the bridging carbons to which it is bonded forms an aromatic ring or a 5 to 8 carbon atom heteroaromatic ring comprising additionally one or more heteroatoms which are independently N, O or S, wherein one or more hydrogen atoms on a carbon atom in said aromatic or heteroaromatic ring are optionally substituted by a moiety which is independently for each occurrence:
(a) —$N(R^*)_2$, wherein $R^*$ is —H or a $C_{1-4}$-alkyl; (b) halogen; (c) $C_{3-10}$-heteroaryl; (d) $C_{1-6}$-alkyl-, which is optionally substituted on any carbon with one or more —F substituents; (e) $C_{1-6}$-alkyl-O—, which is optionally substituted on any carbon with one or more —F substituents; or (f) —CN; and
"Y" together with the bridging carbon atoms to which it is bonded forms a a cycloalkyl moiety of up to 8 carbon atoms or a heterocycloalkyl moiety of up to 8 to carbon atoms and one or more heteroatoms which are independently N, O or S, and which is optionally substituted by:
(a) —$N(R^*)_2$, wherein $R^*$ is —H or a $C_{1-4}$-alkyl; (b) halogen; (c) $C_{3-10}$-heteroaryl; (d) $C_{1-6}$-alkyl-, which is optionally substituted on any carbon with one or more F substituents; (e) $C_{1-6}$-alkyl-O—, which is optionally substituted on any carbon with one or more F substituents; or (f) —CN.

In some embodiments compounds of the invention preferably have the structure of Formula D:

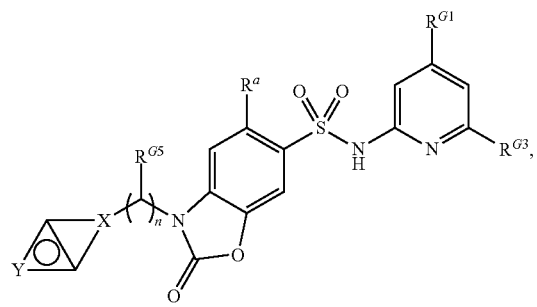

Formula D or a salt thereof
wherein:
"n" is an integer of 0 to 2;
$R^3$ is —H, $C_{1-6}$ alkyl, $C_{1-6}$ alkoxy, —CN or halogen, and when selected to be a halogen is preferably —F;
One of $R^{G1}$ and $R^{G3}$ is —H and the other is —H or Halogen, and when halogen, is preferably —F or —Cl;
$R^{G5}$ is, independently for each occurrence, —H or a linear or branched $C_{1-5}$-alkyl moiety;
"X", together with the bridging carbon atoms to which it is bonded forms a a cycloalkyl moiety of up to 8 carbon atoms or a heterocycloalkyl moiety of up to 8 to carbon atoms and one or more heteroatoms which are independently N, O or S, and which is optionally substituted by:
  (a) —N(R*)$_2$, wherein R* is —H or a $C_{1-4}$-alkyl; (b) halogen; (c) $C_{3-10}$-heteroaryl; (d) $C_{1-6}$-alkyl-, which is optionally substituted on any carbon with one or more —F substituents; (e) $C_{1-6}$-alkyl-O—, which is optionally substituted on any carbon with one or more F substituents; or (f) —CN; and
"Y", together with the bridging carbons to which it is bonded forms an aromatic ring or a 5 to 8 carbon atom heteroaromatic ring comprising additionally one or more heteroatoms which are independently N, O or S, wherein one or more hydrogen atoms on a carbon atom in said aromatic or heteroaromatic ring are optionally substituted by a moiety which is independently for each occurrence:
  (a) —N(R*)$_2$, wherein R* is —H or a $C_{1-4}$-alkyl; (b) halogen; (c) $C_{3-10}$-heteroaryl; (d) $C_{1-6}$-alkyl-, which is optionally substituted on any carbon with one or more —F substituents; (e) $C_{1-6}$-alkyl-O—, which is optionally substituted on any carbon with one or more F substituents; or (f) —CN In some embodiments compounds of the invention are preferably:

N-(6-fluoropyridin-2-yl)-2-oxo-3-[(1R)-1-(1,2,3,4-tetrahydroisoquinolin-8-yl)ethyl]-2,3-dihydro-1,3-benzoxazole-6-sulfonamide;
5-fluoro-N-(6-fluoropyridin-2-yl)-2-oxo-3-[(1R)-1-(1,2,3,4-tetrahydroisoquinolin-8-yl)ethyl]-2,3-dihydro-1,3-benzoxazole-6-sulfonamide;
3-(7-amino-1,2,3,4-tetrahydronaphthalen-1-yl)-5-fluoro-N-(6-fluoropyridin-2-yl)-2-oxo-2,3-dihydro-1,3-benzoxazole-6-sulfonamide;
5-fluoro-N-(6-fluoropyridin-2-yl)-3-(7-fluoro-1,2,3,4-tetrahydronaphthalen-1-yl)-2-oxo-2,3-dihydro-1,3-benzoxazole-6-sulfonamide;
5-fluoro-N-(6-fluoropyridin-2-yl)-3-[(4-fluoro-1,2,3,4-tetrahydroisoquinolin-8-yl)methyl]-2-oxo-2,3-dihydro-1,3-benzoxazole-6-sulfonamide;
(R)-5-fluoro-N-(6-fluoropyridin-2-yl)-3-[(4-fluoro-1,2,3,4-tetrahydroisoquinolin-8-yl)methyl]-2-oxo-2,3-dihydro-1,3-benzoxazole-6-sulfonamide;
(S)-5-fluoro-N-(6-fluoropyridin-2-yl)-3-[(4-fluoro-1,2,3,4-tetrahydroisoquinolin-8-yl)methyl]-2-oxo-2,3-dihydro-1,3-benzoxazole-6-sulfonamide;
5-fluoro-N-(6-fluoropyridin-2-yl)-2-oxo-3-{(1R)-1-[2-(1,2,3,6-tetrahydropyridin-4-yl)phenyl]ethyl}-2,3-dihydro-1,3-benzoxazole-6-sulfonamide;
3-{(1R)-1-[2-(4-aminocyclohex-1-en-1-yl)phenyl]ethyl}-5-fluoro-N-(6-fluoropyridin-2-yl)-2-oxo-2,3-dihydro-1,3-benzoxazole-6-sulfonamide;
5-fluoro-N-(6-fluoropyridin-2-yl)-2-oxo-3-{(1R)-1-[2-(2,5,6,7-tetrahydro-1H-azepin-4-yl)phenyl]ethyl}-2,3-dihydro-1,3-benzoxazole-6-sulfonamide;
3-[(1R)-1-{2-[(1S,5R)-8-azabicyclo[3.2.1]oct-2-en-3-yl]phenyl}ethyl]-5-fluoro-N-(6-fluoropyridin-2-yl)-2-oxo-2,3-dihydro-1,3-benzoxazole-6-sulfonamide;
5-fluoro-N-(6-fluoropyridin-2-yl)-2-oxo-3-{(1R)-1-[2-(1,2,5,6-tetrahydropyridin-3-yl)phenyl]ethyl}-2,3-dihydro-1,3-benzoxazole-6-sulfonamide;
3-{(1R)-1-[2-(3-aminoprop-1-yn-1-yl)phenyl]ethyl}-5-fluoro-N-(6-fluoropyridin-2-yl)-2-oxo-2,3-dihydro-1,3-benzoxazole-6-sulfonamide;
(R)-5-fluoro-N-(6-fluoropyridin-2-yl)-2-oxo-3-(1-(2-(3-(pyrrolidin-1-yl)prop-1-yn-1-yl)phenyl)ethyl)-2,3-dihydrobenzo[d]oxazole-6-sulfonamides;
3-[(1R)-1-(2-{[(1R,2R)-2-aminocyclohexyl]ethynyl}phenyl)ethyl]-5-fluoro-N-(6-fluoropyridin-2-yl)-2-oxo-2,3-dihydro-1,3-benzoxazole-6-sulfonamide;
3-{(1R)-1-[2-(3-amino-4-hydroxybut-1-yn-1-yl)phenyl]ethyl}-5-fluoro-N-(6-fluoropyridin-2-yl)-2-oxo-2,3-dihydro-1,3-benzoxazole-6-sulfonamide;
3-[(1R)-1-(2-{[(1R,2S)-2-aminocyclohexyl]ethynyl}phenyl)ethyl]-5-fluoro-N-(6-fluoropyridin-2-yl)-2-oxo-2,3-dihydro-1,3-benzoxazole-6-sulfonamide;
3-[(1R)-1-{2-[(1-aminocyclohexyl)ethynyl]phenyl}ethyl]-5-fluoro-N-(6-fluoropyridin-2-yl)-2-oxo-2,3-dihydro-1,3-benzoxazole-6-sulfonamide;
3-{(1R)-1-[2-(4-amino-4-methylpent-1-yn-1-yl)phenyl]ethyl}-5-fluoro-N-(6-fluoropyridin-2-yl)-2-oxo-2,3-dihydro-1,3-benzoxazole-6-sulfonamide;
5-fluoro-N-(6-fluoropyridin-2-yl)-3-[(1R)-1-{2-[3-(3-hydroxypyrrolidin-1-yl)prop-1-yn-1-yl]phenyl}ethyl]-2-oxo-2,3-dihydro-1,3-benzoxazole-6-sulfonamide;
3-[(1R)-1-{2-[3-(dimethylamino)prop-1-yn-1-yl]phenyl}ethyl]-5-fluoro-N-(6-fluoropyridin-2-yl)-2-oxo-2,3-dihydro-1,3-benzoxazole-6-sulfonamide;
3-{(1R)-1-[2-(3-azetidin-1-ylprop-1-yn-1-yl)phenyl]ethyl}-5-fluoro-N-(6-fluoropyridin-2-yl)-2-oxo-2,3-dihydro-1,3-benzoxazole-6-sulfonamide;
3-{(1R)-1-[2-(aminomethyl)phenyl]ethyl}-5-fluoro-N-(6-fluoropyridin-2-yl)-2-oxo-2,3-dihydro-1,3-benzoxazole-6-sulfonamide;
3-[(1R)-1-{2-[(dimethylamino)methyl]phenyl}ethyl]-5-fluoro-N-(6-fluoropyridin-2-yl)-2-oxo-2,3-dihydro-1,3-benzoxazole-6-sulfonamide;
5-fluoro-N-(6-fluoropyridin-2-yl)-2-oxo-3-{(1R)-1-[2-(piperidin-1-ylmethyl)phenyl]ethyl}-2,3-dihydro-1,3-benzoxazole-6-sulfonamide;
3-[(1R)-1-(2-azetidin-3-ylphenyl)ethyl]-5-fluoro-N-(6-fluoropyridin-2-yl)-2-oxo-2,3-dihydro-1,3-benzoxazole-6-sulfonamide;
5-fluoro-N-(6-fluoropyridin-2-yl)-3-[(1R)-1-{2-[1-(methylsulfonyl)azetidin-3-yl]phenyl}ethyl]-2-oxo-2,3-dihydro-1,3-benzoxazole-6-sulfonamide;
5-fluoro-N-(6-fluoropyridin-2-yl)-3-{(1R)-1-[2-(3-hydroxyazetidin-3-yl)phenyl]ethyl}-2-oxo-2,3-dihydro-1,3-benzoxazole-6-sulfonamide;
5-fluoro-3-{(1R)-1-[2-(3-fluoroazetidin-3-yl)phenyl]ethyl}-N-(6-fluoropyridin-2-yl)-2-oxo-2,3-dihydro-1,3-benzoxazole-6-sulfonamide;
3-[(7-amino-5,6,7,8-tetrahydronaphthalen-1-yl)methyl]-5-fluoro-N-(6-fluoropyridin-2-yl)-2-oxo-2,3-dihydro-1,3-benzoxazole-6-sulfonamide;
3-[(7-amino-5,6,7,8-tetrahydronaphthalen-1-yl)methyl]-5-fluoro-N-(6-fluoropyridin-2-yl)-2-oxo-2,3-dihydro-1,3-benzoxazole-6-sulfonamide;
3-[(7-amino-5,6,7,8-tetrahydronaphthalen-1-yl)methyl]-N-(6-fluoropyridin-2-yl)-2-oxo-2,3-dihydro-1,3-benzoxazole-6-sulfonamide;

3-[(1R)-1-(2-bromo-3-methylphenyl)ethyl]-5-fluoro-N-(6-fluoropyridin-2-yl)-2-oxo-2,3-dihydro-1,3-benzoxazole-6-sulfonamide;
5-fluoro-N-(5-fluoropyridin-2-yl)-2-oxo-3-[(1R)-1-(1,2,3,4-tetrahydroisoquinolin-8-yl)ethyl]-2,3-dihydro-1,3-benzoxazole-6-sulfonamide;
3-[(1R)-1-(2-azetidin-3-ylphenyl)ethyl]-5-fluoro-N-(5-fluoropyridin-2-yl)-2-oxo-2,3-dihydro-1,3-benzoxazole-6-sulfonamide;
N-(4-chloropyridin-2-yl)-5-fluoro-2-oxo-3-[(1R)-1-(1,2,3,4-tetrahydroisoquinolin-8-yl)ethyl]-2,3-dihydro-1,3-benzoxazole-6-sulfonamide;
N-(6-fluoropyridin-2-yl)-5-methyl-2-oxo-3-[(1R)-1-(1,2,3,4-tetrahydroisoquinolin-8-yl)ethyl]-2,3-dihydro-1,3-benzoxazole-6-sulfonamide;
3-[(7-amino-5,6,7,8-tetrahydronaphthalen-1-yl)methyl]-N-(6-fluoropyridin-2-yl)-5-methyl-2-oxo-2,3-dihydro-1,3-benzoxazole-6-sulfonamide;
3-[(7-amino-5,6,7,8-tetrahydronaphthalen-1-yl)methyl]-N-(6-fluoropyridin-2-yl)-5-methyl-2-oxo-2,3-dihydro-1,3-benzoxazole-6-sulfonamide;
3-{(1R)-1-[2-(aminomethyl)phenyl]ethyl}-N-(6-fluoropyridin-2-yl)-5-methyl-2-oxo-2,3-dihydro-1,3-benzoxazole-6-sulfonamide;
N-(6-fluoropyridin-2-yl)-5-methyl-2-oxo-3-{(1R)-1-[2-(1,2,3,6-tetrahydropyridin-4-yl)phenyl]ethyl}-2,3-dihydro-1,3-benzoxazole-6-sulfonamide; or
N-(6-fluoropyridin-2-yl)-5-methyl-2-oxo-3-[(1R)-1-(2-piperidin-4-ylphenyl)ethyl]-2,3-dihydro-1,3-benzoxazole-6-sulfonamide, or a salt of any thereof.

In some embodiments compounds of the invention are preferably:

3-[(1R)-1-(2-bromophenyl)ethyl]-5-fluoro-N-(6-fluoropyridin-2-yl)-2-oxo-2,3-dihydro-1,3-benzoxazole-6-sulfonamide;
3-[(1R)-1-(3-bromophenyl)ethyl]-5-fluoro-N-(6-fluoropyridin-2-yl)-2-oxo-2,3-dihydro-1,3-benzoxazole-6-sulfonamide;
3-[(1R)-1-(3-bromophenyl)ethyl]-N-(6-fluoropyridin-2-yl)-5-methyl-2-oxo-2,3-dihydro-1,3-benzoxazole-6-sulfonamide;
3-[(1R)-1-(3-bromo-2-methylphenyl)ethyl]-N-(6-fluoropyridin-2-yl)-5-methyl-2-oxo-2,3-dihydro-1,3-benzoxazole-6-sulfonamide;
3-[(1R)-1-(2-bromo-3-methylphenyl)ethyl]-N-(6-fluoropyridin-2-yl)-5-methyl-2-oxo-2,3-dihydro-1,3-benzoxazole-6-sulfonamide;
3-[(1R)-1-(2-bromophenyl)ethyl]-N-(6-fluoropyridin-2-yl)-5-methyl-2-oxo-2,3-dihydro-1,3-benzoxazole-6-sulfonamide;
3-[(1R)-1-(3-bromo-2-methylphenyl)ethyl]-N-(6-fluoropyridin-2-yl)-5-fluoro-2-oxo-2,3-dihydro-1,3-benzoxazole-6-sulfonamide;
3-{(1R)-1-[2-(aminomethyl)-3-methylphenyl]ethyl}-5-fluoro-N-(6-fluoropyridin-2-yl)-2-oxo-2,3-dihydro-1,3-benzoxazole-6-sulfonamide;
3-{(1R)-1-[2-(aminomethyl)-3-methylphenyl]ethyl}-N-(6-fluoropyridin-2-yl)-5-methyl-2-oxo-2,3-dihydro-1,3-benzoxazole-6-sulfonamide;
3-{(1R)-1-[2-(aminomethyl)phenyl]ethyl}-N-(6-fluoropyridin-2-yl)-5-methyl-2-oxo-2,3-dihydro-1,3-benzoxazole-6-sulfonamide;
3-{(1R)-1-[3-(aminomethyl)-2-methylphenyl]ethyl}-5-fluoro-N-(6-fluoropyridin-2-yl)-2-oxo-2,3-dihydro-1,3-benzoxazole-6-sulfonamide;
3-{(1R)-1-[3-(aminomethyl)phenyl]ethyl}-5-fluoro-N-(6-fluoropyridin-2-yl)-2-oxo-2,3-dihydro-1,3-benzoxazole-6-sulfonamide;
5-fluoro-N-(6-fluoropyridin-2-yl)-3-{(1R)-1-[3-(morpholin-4-ylmethyl)phenyl]ethyl}-2-oxo-2,3-dihydro-1,3-benzoxazole-6-sulfonamide;
5-fluoro-N-(6-fluoropyridin-2-yl)-3-[(1R)-1-{3-[(4-methylpiperazin-1-yl)methyl]phenyl}ethyl]-2-oxo-2,3-dihydro-1,3-benzoxazole-6-sulfonamide;
3-[(1R)-1-{3-[(dimethylamino)methyl]phenyl}ethyl]-5-fluoro-N-(6-fluoropyridin-2-yl)-2-oxo-2,3-dihydro-1,3-benzoxazole-6-sulfonamide;
5-fluoro-N-(6-fluoropyridin-2-yl)-3-[(1R)-1-{3-[(3-fluoropyrrolidin-1-yl)methyl]phenyl}ethyl]-2-oxo-2,3-dihydro-1,3-benzoxazole-6-sulfonamide;
3-[(1R)-1-{3-[(tert-butylamino)methyl]phenyl}ethyl]-5-fluoro-N-(6-fluoropyridin-2-yl)-2-oxo-2,3-dihydro-1,3-benzoxazole-6-sulfonamide;
3-{(1R)-1-[3-(2-amino ethyl)phenyl]ethyl}-5-fluoro-N-(6-fluoropyridin-2-yl)-2-oxo-2,3-dihydro-1,3-benzoxazole-6-sulfonamide;
3-{(1R)-1-[3-(2-aminoethyl)-2-methylphenyl]ethyl}-5-fluoro-N-(6-fluoropyridin-2-yl)-2-oxo-2,3-dihydro-1,3-benzoxazole-6-sulfonamide;
5-fluoro-N-(6-fluoropyridin-2-yl)-2-oxo-3-{(1R)-1-[2-(pyrrolidin-2-yl)phenyl]ethyl}-2,3-dihydro-1,3-benzoxazole-6-sulfonamide;
5-fluoro-N-(6-fluoropyridin-2-yl)-3-{(1R)-1-[3-methyl-2-(pyrrolidin-2-yl)phenyl]ethyl}-2-oxo-2,3-dihydro-1,3-benzoxazole-6-sulfonamide;
5-fluoro-N-(6-fluoropyridin-2-yl)-2-oxo-3-{(1R)-1-[3-(pyrrolidin-2-yl)phenyl]ethyl}-2,3-dihydro-1,3-benzoxazole-6-sulfonamide;
3-{(1R)-1-[3-(3-amino-3-methylbut-1-yn-1-yl)phenyl]ethyl}-5-fluoro-N-(6-fluoropyridin-2-yl)-2-oxo-2,3-dihydro-1,3-benzoxazole-6-sulfonamide;
5-fluoro-N-(6-fluoropyridin-2-yl)-3-[(1R)-1-{3-[3-(methylamino)prop-1-yn-1-yl]phenyl}ethyl]-2-oxo-2,3-dihydro-1,3-benzoxazole-6-sulfonamide;
3-[(1R)-1-{3-[3-(dimethylamino)prop-1-yn-1-yl]phenyl}ethyl]-5-fluoro-N-(6-fluoropyridin-2-yl)-2-oxo-2,3-dihydro-1,3-benzoxazole-6-sulfonamide;
3-[(1R)-1-{3-[(1-amino cyclohexyl)ethynyl]phenyl}ethyl]-5-fluoro-N-(6-fluoropyridin-2-yl)-2-oxo-2,3-dihydro-1,3-benzoxazole-6-sulfonamide;
3-{(1R)-1-[3-(3-aminobut-1-yn-1-yl)phenyl]ethyl}-5-fluoro-N-(6-fluoropyridin-2-yl)-2-oxo-2,3-dihydro-1,3-benzoxazole-6-sulfonamide;
3-[(1R)-1-{3-[3-(cyclohexylamino)prop-1-yn-1-yl]phenyl}ethyl]-5-fluoro-N-(6-fluoropyridin-2-yl)-2-oxo-2,3-dihydro-1,3-benzoxazole-6-sulfonamide;
5-fluoro-N-(6-fluoropyridin-2-yl)-2-oxo-3-[(1R)-1-{3-[3-(pyrrolidin-1-yl)prop-1-yn-1-yl]phenyl}ethyl]-2,3-dihydro-1,3-benzoxazole-6-sulfonamide;
5-fluoro-N-(6-fluoropyridin-2-yl)-3-[(1R)-1-{3-[3-(morpholin-4-yl)prop-1-yn-1-yl]phenyl}ethyl]-2-oxo-2,3-dihydro-1,3-benzoxazole-6-sulfonamide;
5-fluoro-N-(6-fluoropyridin-2-yl)-2-oxo-3-{(1R)-1-[3-(piperidin-2-ylethynyl)phenyl]ethyl}-2,3-dihydro-1,3-benzoxazole-6-sulfonamide;
5-fluoro-N-(6-fluoropyridin-2-yl)-2-oxo-3-{(1R)-1-[3-(pyrrolidin-2-ylethynyl)phenyl]ethyl}-2,3-dihydro-1,3-benzoxazole-6-sulfonamide;
5-fluoro-N-(6-fluoropyridin-2-yl)-2-oxo-3-[(1R)-1-{3-[3-(piperazin-1-yl)prop-1-yn-1-yl]phenyl}ethyl]-2,3-dihydro-1,3-benzoxazole-6-sulfonamide;

3-[(1R)-1-{3-[(1-aminocyclopropyl)ethynyl]phenyl}ethyl]-5-fluoro-N-(6-fluoropyridin-2-yl)-2-oxo-2,3-dihydro-1,3-benzoxazole-6-sulfonamide;

3-[(1R)-1-{3-[3-(azetidin-1-yl)prop-1-yn-1-yl]phenyl}ethyl]-5-fluoro-N-(6-fluoropyridin-2-yl)-2-oxo-2,3-dihydro-1,3-benzoxazole-6-sulfonamide;

5-fluoro-N-(6-fluoropyridin-2-yl)-3-[(1R)-1-{3-[3-(4-methylpiperazin-1-yl)prop-1-yn-1-yl]phenyl}ethyl]-2-oxo-2,3-dihydro-1,3-benzoxazole-6-sulfonamide;

3-[(1R)-1-{3-[3-(diethylamino)prop-1-yn-1-yl]phenyl}ethyl]-5-fluoro-N-(6-fluoropyridin-2-yl)-2-oxo-2,3-dihydro-1,3-benzoxazole-6-sulfonamide;

5-fluoro-N-(6-fluoropyridin-2-yl)-3-[(1R)-1-{3-[3-(3-hydroxypyrrolidin-1-yl)prop-1-yn-1-yl]phenyl}ethyl]-2-oxo-2,3-dihydro-1,3-benzoxazole-6-sulfonamide;

3-[(1R)-1-(3-{[(1S,2S)-2-aminocyclohexyl]ethynyl}phenyl)ethyl]-5-fluoro-N-(6-fluoropyridin-2-yl)-2-oxo-2,3-dihydro-1,3-benzoxazole-6-sulfonamide;

3-[(1R)-1-{3-[(2-aminocyclopentyl)ethynyl]phenyl}ethyl]-5-fluoro-N-(6-fluoropyridin-2-yl)-2-oxo-2,3-dihydro-1,3-benzoxazole-6-sulfonamide;

5-fluoro-N-(6-fluoropyridin-2-yl)-2-oxo-3-[(1R)-1-{3-[4-(piperazin-1-yl)but-1-yn-1-yl]phenyl}ethyl]-2,3-dihydro-1,3-benzoxazole-6-sulfonamide;

3-[(1R)-1-{3-[3-(azetidin-1-yl)prop-1-yn-1-yl]phenyl}ethyl]-N-(6-fluoropyridin-2-yl)-5-methyl-2-oxo-2,3-dihydro-1,3-benzoxazole-6-sulfonamide;

3-{(1R)-1-[3-(3-aminoprop-1-yn-1-yl)phenyl]ethyl}-5-fluoro-N-(6-fluoropyridin-2-yl)-2-oxo-2,3-dihydro-1,3-benzoxazole-6-sulfonamide;

3-{(1R)-1-[3-(3-aminoprop-1-yn-1-yl)-2-methylphenyl]ethyl}-5-fluoro-N-(6-fluoropyridin-2-yl)-2-oxo-2,3-dihydro-1,3-benzoxazole-6-sulfonamide;

3-{(1R)-1-[3-(3-aminoprop-1-yn-1-yl)phenyl]ethyl}-N-(6-fluoropyridin-2-yl)-5-methyl-2-oxo-2,3-dihydro-1,3-benzoxazole-6-sulfonamide;

3-{(1R)-1-[3-(3-aminoprop-1-yn-1-yl)-2-methylphenyl]ethyl}-N-(6-fluoropyridin-2-yl)-5-methyl-2-oxo-2,3-dihydro-1,3-benzoxazole-6-sulfonamide;

3-[(1R)-1-(2-{[(1S,2S)-2-aminocyclohexyl]ethynyl}-3-methylphenyl)ethyl]-N-(6-fluoropyridin-2-yl)-5-methyl-2-oxo-2,3-dihydro-1,3-benzoxazole-6-sulfonamide;

3-[(1R)-1-(2-{[(1R,2R)-2-aminocyclohexyl]ethynyl}-3-methylphenyl)ethyl]-N-(6-fluoropyridin-2-yl)-5-methyl-2-oxo-2,3-dihydro-1,3-benzoxazole-6-sulfonamide;

3-[(1R)-1-(2-{[(1S,2S)-2-aminocyclohexyl]ethynyl}-3-methylphenyl)ethyl]-5-fluoro-N-(6-fluoropyridin-2-yl)-2-oxo-2,3-dihydro-1,3-benzoxazole-6-sulfonamide;

3-{(1R)-1-[3-(3-aminopropyl)phenyl]ethyl}-5-fluoro-N-(6-fluoropyridin-2-yl)-2-oxo-2,3-dihydro-1,3-benzoxazole-6-sulfonamide;

3-{(1R)-1-[3-(3-amino-propyl)phenyl]ethyl}-N-(6-fluoropyridin-2-yl)-5-methyl-2-oxo-2,3-dihydro-1,3-benzoxazole-6-sulfonamide;

3-{(1R)-1-[3-(3-amino-propyl)-2-methylphenyl]ethyl}-5-fluoro-N-(6-fluoropyridin-2-yl)-2-oxo-2,3-dihydro-1,3-benzoxazole-6-sulfonamide;

3-[(1R)-1-{3-[3-(azetidin-1-yl)propyl]phenyl}ethyl]-5-fluoro-N-(6-fluoro-pyridin-2-yl)-2-oxo-2,3-dihydro-1,3-benzoxazole-6-sulfonamide;

3-{(1R)-1-[2-(2-amino ethyl)phenyl]ethyl}-5-fluoro-N-(6-fluoropyridin-2-yl)-2-oxo-2,3-dihydro-1,3-benzoxazole-6-sulfonamide; or 3-{(1R)-1-[2-(2-aminoethyl)-3-methylphenyl]-ethyl}-5-fluoro-N-(6-fluoropyridin-2-yl)-2-oxo-2,3-dihydro-1,3-benzoxazole-6-sulfonamide or a salt of any thereof.

In some embodiments, compounds of the invention are preferably:

5-fluoro-N-(6-fluoropyridin-2-yl)-2-oxo-3-{(1R)-1-[3-(1,2,3,6-tetrahydropyridin-4-yl)phenyl]ethyl}-2,3-dihydro-1,3-benzoxazole-6-sulfonamide;

5-fluoro-N-(6-fluoropyridin-2-yl)-2-oxo-3-{(1R)-1-[3-(1,2,5,6-tetrahydropyridin-3-yl)phenyl]ethyl}-2,3-dihydro-1,3-benzoxazole-6-sulfonamide;

5-fluoro-N-(6-fluoropyridin-2-yl)-2-oxo-3-{(1R)-1-[3-(1H-pyrazol-5-yl)phenyl]ethyl}-2,3-dihydro-1,3-benzoxazole-6-sulfonamide;

5-fluoro-N-(6-fluoropyridin-2-yl)-2-oxo-3-{(1R)-1-[2-(piperazin-1-yl)phenyl]ethyl}-2,3-dihydro-1,3-benzoxazole-6-sulfonamide; or N-(6-fluoropyridin-2-yl)-5-methyl-2-oxo-3-{(1R)-1-[2-(piperazin-1-yl)phenyl]ethyl}-2,3-dihydro-1,3-benzoxazole-6-sulfonamide.

In some embodiments, a compound of the invention is 3-[(4,4-difluoro-1,2,3,4-tetrahydroisoquinolin-8-yl)methyl]-5-fluoro-N-(6-fluoropyridin-2-yl)-2-oxo-2,3-dihydro-1,3-benzoxazole-6-sulfonamide.

As used herein, unless otherwise specified, the term "Na$_v$ 1.7 (equivalently, Nav 1.7) blocker" means a compound of the invention exhibiting a potency (IC$_{50}$) of less than about 2 μM when assayed in accordance with the PatchXpress® assay described herein. Preferred compounds exhibit at least 10-fold selectivity for Na$_v$ 1.7 sodium channels over Na$_v$ 1.5 sodium channels, more preferably at least 100-fold selectivity for Na$_v$ 1.7 sodium channels over Na$_v$ 1.5 sodium channels when functional potency for each channel are compared using the PatchXpress® assay system described herein. Where the term "Na$_v$ 1.7 activity" is used herein, it refers to the ability of a compound to block activity in a Na$_v$ 1.7 sodium ion channel;

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

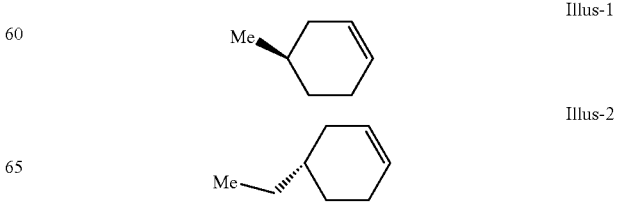

Illus-1

Illus-2

-continued

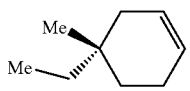

Illus-3

As is conventional, ordinary "stick" bonds or "wavy" bonds are used where there is a mixture of possible isomers present, including a racemic mixture of possible isomers As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level of a substance appropriate for pharmaceutical use.

"at least one" used in reference to substituents on a compound or moiety appended to the core structure of a compound means that one substituent of the group of substituents specified is present, and more than one substituent may be bonded to chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of compound or of a composition comprising a compound of the present invention which is effective in treating or inhibiting the diseases or conditions described herein, and thus producing the desired therapeutic, ameliorative, inhibitory or preventative effect. For example, in the methods of treating or managing neuropathic pain with one or more of the compounds described herein it means the amount of a compound of Formula A that results in therapeutic response of a neuropathic pain condition ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

"solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is water.

The term "substituted" means that one or more of the enumerated substituents (or, where a list of substituents are not specifically enumerated, the default substituents specified in this "Definitions" section for the particular type of substrate which contains variable substituents) may occupy one or more of the bonding positions on the substrate typically occupied by "—H", provided that such substitution does not exceed the normal valency rules for the atom in the bonding configuration present in the substrate, and that the substitution ultimate provides a stable compound, e.g., mutually reactive substituents are not present geminal or vicinal to each other, and wherein such a compound is sufficiently robust to survive isolation to a useful degree of purity from a reaction mixture; when the text indicates optional substitution of a moiety (e.g. "optionally substituted") the term means "if present, one or more of the enumerated (or default substituents for the specified substrate) may be present on the substrate in a bonding position normally occupied by a hydrogen atom" in accordance with the definition of "substituted" presented herein;

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)—", or by the structural representation:

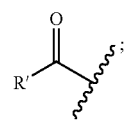

"acyl" means an R'—C(O)—, where R' is linear, branched or cyclic alkyl; linear, branched or cyclic alkenyl; or linear, branched or cyclic alkynyl moiety, each of which moieties may be substituted; wherein the acyl substituent is bonded through the carbonyl carbon to the substrate of which it is a substituent; non-limiting examples of suitable acyl groups include formyl, acetyl, propanoyl, 2-methylpropanoyl, butanoyl and cyclohexanoyl;

"alkenyl" means an aliphatic hydrocarbon moiety which is not aromatic but includes in its structure at least one constituent of the structure —(R'C═CR'$_2$) or (R'C═CR')—, where R' is a defined substituent, for example —H or -alkyl; the alkenyl moiety may be incorporated into a linear hydrocarbon chain, or incorporated into a cyclic hydrocarbon chain (termed "cycloalkenyl") and may comprise further, linear, branched, or cyclic substituents depending from the carbon atoms of the chain, preferably the chain comprises about 2 to about 15 carbon atoms; more preferably from about 2 to about 12 carbon atoms; and more preferably chains comprise from about 2 to about 6 carbon atoms;

the term "substituted alkenyl", unless specified otherwise by a recitation of specific substituents defining the term where used, means that the alkenyl group is substituted by one or more substituents which are independently for each occurrence: aryl; and $C_{1-10}$-alkyl, optionally substituted, as defined herein;

"alkoxy" means a moiety of the structure: alkyl-O— (i.e., the bond to the substrate moiety is through the ether oxygen), wherein the alkyl portion of the moiety is as defined below for alkyl; non-limiting examples of suitable alkoxy groups include methoxy, ethoxy, n-propoxy, isopropoxy, n-butoxy and heptoxy;

"alkoxycarbonyl" means a moiety of the structure alkyl-O—C(O)—, equivalently represented as [alkyl-O—(C═O)—] and also as R—O(C═O)—, where "R" is a defined alkyl moiety, (i.e., the bond to the parent moiety is through the carbonyl carbon) wherein the alkyoxy portion of the moiety is as previously defined; non-limiting examples of suitable alkoxycarbonyl groups include methoxycarbonyl and ethoxycarbonyl;

"alkyl" (including the alkyl portions of other moieties, such as trifluoromethyl-alkyl- and alkoxy-) means an aliphatic hydrocarbon chain comprising from about 1 to about 20 carbon atoms (that is, "$C_{1-20}$ alkyl"), preferably 1 to about 10 carbon atoms (herein "$C_{1-10}$ alkyl"), unless the term is modified by an indication that a shorter chain is contemplated, for example, an alkyl moiety of up to 8 carbon atoms (designated herein "$C_{1-8}$ alkyl"); the term "alkyl", unless specifically limited by another term, for example, "linear", "branched", or "cyclic", includes alkyl moieties which are linear (a hydrocarbon chain with no aliphatic hydrocarbon "branches" appended to it); branched (a main hydrocarbon chain comprising up to the maximum specified number of carbon atoms with a lower-alkyl chain appended to one or more carbon atoms comprising, but not terminating, the main hydrocarbon chain); and cyclic (the main hydrocarbon chain forms an cyclic aliphatic moiety of from 3 carbon atoms, the minimum number necessary to provide a cyclic moiety, up to the maximum number of specified carbon atoms), accordingly when unmodified, the term "$C_{1-X}$ alkyl" refers to linear, branched, or cyclic alkyl, and the "$C_{1-X}$" designation means: for a cyclic moiety a ring comprising at minimum 3 carbon atoms up to "X" carbon atoms; for a branched moiety, a main chain of at least 3 carbon atoms up to "X" carbon atoms with at least one linear or branched alkyl moiety bonded to a carbon atom which does not terminate the chain; and for a linear alkyl, a moiety comprising one carbon atom (i.e., -methyl), up to "X" carbon atoms; when the term "alkyl" is modified by "substituted" or "optionally substituted" it means an alkyl group having substituents in accordance with the relevant definitions appearing below; where use of the terms "substituted" or "optionally substituted" modify "alkyl" and substituent moieties are not specifically enumerated, the substituents bonded to the alkyl substrate are independently for each occurrence (in accordance with definitions appearing herein): $C_{1-20}$ alkyl; halogen; -alkoxy; —OH; —CN; alkylthio-; amino, —NH(linear or branched alkyl), —NH(cycloalkyl), —N(alkyl)$_2$, —(C═O)—OH; —C(O)O-alkyl; —S(alkyl); or —S(O$_2$)-alkyl; or -aryl; cycloalkyl moieties may alternatively, or in addition, be substituted with one or more, "ring-system substituents" as that term is defined herein;

"lower alkyl" means a group comprising about 1 to about 6 carbon atoms in the chain (i.e. $C_{1-6}$); non-limiting examples of suitable alkyl groups include methyl (also abbreviated in the structures as "Me-"), ethyl, n-propyl, isopropyl, cyclopropyl, n-butyl, t-butyl, cyclobutyl, n-pentyl, neopentyl, cyclopentyl, n-hexyl, cyclohexyl and the like, fluoromethyl, trifluoromethyl, cyclopropylmethyl, and the like;

where the term "alkyl" is indicated with two hyphens (i.e., "-alkyl-" it indicates that the alkyl moiety is bonded in a manner that the alkyl moiety connects a substrate with another moiety, for example, "-alkyl-OH" indicates an alkyl moiety connecting a hydroxyl moiety to a substrate;

"alkylaryl" (or alkaryl) means an alkyl-aryl-group (i.e., the bond to the parent moiety is through the aryl group) wherein the alkyl group is unsubstituted or substituted as defined above, and the aryl group is unsubstituted or substituted as defined below; preferred alkylaryl moieties comprise a lower alkyl group; non-limiting examples of suitable alkylaryl groups include o-tolyl, p-tolyl and xylyl;

in general, as exemplified by the term "alkyl-aryl" defined above, a substituent which is called out by the combination of terms used to define two other substituent fragments indicates that the substituent called out by the last term used is bonded to the substrate whilst the preceding term called out is bonded in turn to the substituent fragment it precedes, proceeding right to left to understand the order in which the various fragments are bonded to the substrate;

"alkylsulfinyl" means an alkyl-S(O)— moiety (i.e., the moiety is bonded to a substrate through the sulfur atom of the sulfinyl moiety); "alkylthio" means an alkyl-S— group (i.e., the moiety is bonded to a substrate through the sulfur atom of the moiety); "alkylsulfonyl" means an alkyl-S(O$_2$)— group (i.e., the moiety is bonded to a substrate through the sulfur atom of the sulfonyl moiety), suitable alkyl groups may be unsubstituted or substituted as previously defined; preferred groups are those in which the alkyl group is lower alkyl;

"alkynyl" means an aliphatic hydrocarbon group (chain) comprising at least one moiety of the structure:

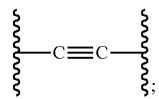

or the structure:

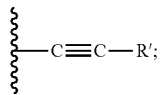

wherein R' is a defined substituent, the alkynyl moiety may be incorporated into a linear or branched hydrocarbon chain, or incorporated into a cyclic hydrocarbon chain (non-aromatic, termed "cycloalkynyl"); preferably hydrocarbon chains of an alkynyl moiety comprises about 2 to about 15 carbon atoms; more preferably alkynyl groups comprise about 2 to about 12 carbon atoms in the chain; and more preferably about 2 to about 4 carbon atoms in the chain;

"amino" means an —NR$_2$ group wherein R is selected independently for each occurrence from —H or alkyl, alkylamino means —NR'$_2$, wherein one R' is -alkyl and the other is —H or -alkyl selected independently for each occurrence, non-limiting examples of alkylamino moieties are —NH—CH$_3$ (methylamino-) and —N(CH$_3$)$_2$ (dimethylamino);

"ammonium ion" means —N$^+$R$_3$, wherein R is independently —H, alkyl, substituted alkyl, or the cationic portion of a dissociated acid capable of producing an ammonium ion from an amine; when not explicitly shown in representations herein the presence of an ammonium ion presumes that a charge-balancing anion is associated with the ammonium ion moiety, which anion is derived from the anionic portion of the acid used to provide said ammonium ion, it will be appreciated that many of the nitrogen atoms present in compounds of the invention may be converted to an ammonium ion thereby providing a salt of the parent compound, which is within the scope of the invention;

"aryl" (sometimes abbreviated "ar") means an aromatic monocyclic or multicyclic ring-system comprising about 6 to about 14 carbon atoms (denoted herein also as "C$_{6-14}$-aryl"), preferably about 6 to about 10 carbon atoms ("C$_{6-10}$-aryl"); the aryl group may be optionally substituted with one or more independently selected "ring-system substituents" (defined below). Non-limiting examples of suitable aryl groups include:

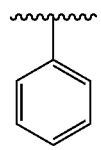

(phenyl) and

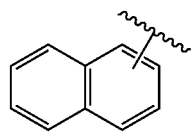

(naphthyl), wherein bonding can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"aryloxy" means an aryl-O— group (i.e., the moiety is bonded to a substrate through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to a substrate is through the carbonyl carbon) wherein the aryl group is unsubstituted or substituted as previously defined; non-limiting examples of suitable aryloxycarbonyl groups include phenoxycarbonyl and naphthoxycarbonyl;

the term the terms "sulfinyl" means (—SO—), "sulfonyl" means (—S(O$_2$)—), and the term "thio" means (—S—), and in combination with any other substituent terms, mean the same thing, thus, for example: "arylsulfinyl" means an aryl-S(O)— group; "arylsulfonyl" means an aryl-S(O$_2$)— group; and "arylthio" means an aryl-S— group (i.e., the bond of the first-named substituent is to the substrate through the sulfur atom in each case) wherein aryl is unsubstituted or substituted as previously defined;

a "carboxylic acid" moiety means a substituent having the formula "—C(O)—OH", wherein the moiety is bonded to a substrate is through the carbonyl carbon;

"cycloalkyl", also defined above with the "alkyl" definition, means a non-aromatic mono- or multicyclic ring-system comprising, unless specified otherwise, from 3 to about 20 carbon atoms which may be optionally substituted with one or more "ring-system substituents" as defined herein; cycloalkyl includes multicyclic cycloalkyls, for example, 1-decalin, norbornyl, adamantyl and the like;

"halogen" means fluorine, chlorine, bromine, or iodine; preferred halogens are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl means that all bonding positions not participating in bonding the alkyl substituent to a substrate are occupied by a halogen, for example, perfluoroalkyl, where alkyl is methyl, means —CF$_3$;

"heteroaryl" means an aromatic substituent comprising a monocyclic or multicyclic ring of from 5 to about 14 ring atoms, preferably about 5 to about 10 ring atoms, in which one or more of the ring atoms is an element other than carbon, for example nitrogen, oxygen or sulfur, alone or in combination; preferred heteroaryl moieties comprise 5 ring atoms, for example, thiazole thiadiazole, imidazole, isothiazole, oxazole, oxadiazole, or pyrazole; the "heteroaryl" may be optionally substituted at chemically available ring atoms by one or more independently selected "ring-system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: tetrahydroquinolinyl-moiety

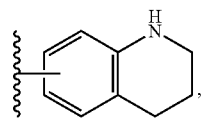

pyridyl-

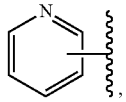

thiopenyl-

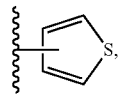

furanyl-

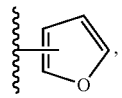

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, for example:

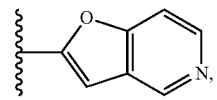

and the like (unless otherwise noted, bonded to the substrate through any available atom that results in a stable bonding arrangement);

"heterocyclyl" (or heterocycloalkyl) means a non-aromatic saturated monocyclic or multicyclic ring-system comprising about 3 to about 10 ring atoms, preferably about 5 to about 10 ring atoms, in which one or more of the atoms in the ring-system is an element other than carbon, for example nitrogen, oxygen or sulfur, alone or in combination, provided that there are no adjacent oxygen and/or sulfur atoms present in the ring system and in some embodiments, preferably, heterocyclyl moieties contain about 5 to about 6 ring atoms;

the prefix aza, oxa or thia before the heterocyclyl root name means that at least one nitrogen, oxygen or sulfur atom, respectively, is present as a ring atom;

a heterocyclyl moiety may be optionally substituted by one or more "ring-system substituents" (defined below) which are selected independently for each occurrence;

the nitrogen or sulfur atom of the heterocyclyl can be optionally oxidized to the corresponding N-oxide, S-oxide or S,S-dioxide;

non-limiting examples of suitable monocyclic heterocyclyl rings include piperidyl, pyrrolidinyl, piperazinyl, morpholinyl, (where unless otherwise noted the moiety is bonded to the substrate through any of ring carbon atoms C2, C3, C5, or C6), as carbon numbers are illustrated:

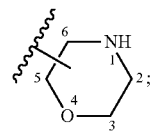

thiomorpholinyl, thiomorpholinyl dione, thiazolidinyl, 1,3-dioxolanyl, 1,4-dioxanyl, tetrahydrofuranyl, tetrahydrothiophenyl, tetrahydrothiopyranyl, and the like;

"Ring-system substituent" means a substituent attached to a carbon atom in the cyclic or heterocyclic portion of an aromatic or non-aromatic moiety that, for example, replaces a bonding position normally occupied by a hydrogen atom on the ring system. Unless modified by exclusions or additions, the term "ring-system substituent" means one or more moieties independently selected from: alkyl, aryl, heteroaryl, aralkyl, alkylaryl, aralkenyl, heteroaralkyl, alkylheteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently: hydrogen, alkyl, aryl, and aralkyl (as defined herein);

"tetrahydropyranyl" moiety means a 6-member cyclic ether of the formula:

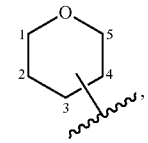

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate may optionally be occupied by specified or optional substituents;

"piperidinyl" means:

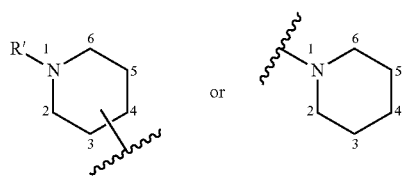

where, the open bond line terminated on one end with a wavy line indicates the ring atom through which the moiety is bonded to the substrate (i.e., any of carbon atoms 2 to 6 (left-hand structure) or the ring nitrogen atom (right-hand structure), which moiety is also optionally substituted on any of the bonding positions on the nitrogen atom or on carbon atoms 2 to 6 of the ring which are not participating in a bond to the substrate, with a "ring-system substituent" or a specified or optional substituent, and wherein R', if present, is either —H or another specified substituent;

"pyridinyl" means:

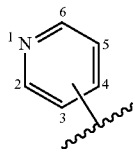

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, may optionally be occupied by a specified substituent;

"quinoline" means:

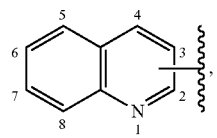

where, the bond-terminated-with-wavy-line indicates that the moiety is bonded to the substrate through any of carbon atoms 2 to 8, and wherein any of the bonding positions on carbon atoms 2 to 8 normally occupied by a hydrogen atom, that is, any bonding positions on carbon atoms 2 to 8 which are not bonded to the substrate, may optionally be occupied by one of a list of enumerated substituents;

For any of the foregoing ring-system moieties, bonding of the moiety through a specific ring carbon atom (or heteroatom) is sometimes described for convenience and "bonded through C—X to C—Y carbon atoms", where "X" and "Y" are integers referring to the carbon atoms, for example, as numbered in the examples above;

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example

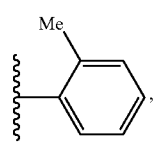 [SMILES: *c1ccccc1C]

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding, for example:

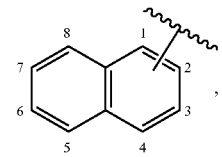

indicates that the naphthalene moiety may be bonded to the substrate through any of carbons 1 to 8.

Any carbon or heteroatom with unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit may contain fixed amounts of the afore-said "more than one pharmaceutically active agents". The term "bulk composition" is a pharmaceutical composition that has not yet been formed into individual dosage units.

This invention also includes the compounds of this invention in isolated and purified form. Polymorphic forms of the compounds of Formula A, and of the salts, solvates and prodrugs of the compounds of Formula A, are intended to be included in the present invention. Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including prodrugs of compounds of the invention as well as the salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention may have the S or R configuration as defined by the *IUPAC* 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diasteromeric mixtures can be separated into their individual diastereomers on the basis of their physical chemical differences by methods well known to those skilled in the art, for example, by chiral chromatography and/or fractional crystallization. As is know, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding enantiomers.

Where the compounds of the invention form salts by known, ordinary methods, these salts are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, for example, but not limited to, a nitrogen atom, for example, an amine, pyridine or imidazole, and an acidic moiety, for example, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the invention may be formed, for example, by reacting a compound of the invention with an amount of acid or base, for example, an equivalent amount, in a medium in which the salt precipitates or in an aqueous medium wherein the product is obtained by lyophilization. Acids (and bases) which are generally considered suitable for the formation of pharmaceutically useful salts from basic (or acidic) pharmaceutical compounds are discussed, for example, by S. Berge et al., *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference.

Exemplary acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methylsulfates, 2-naphthalene-sulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. In some embodiments, HCl salts are preferred.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylene-diamine), N-methyl-D-glucamines, N-methyl-D-glucamides, t-butyl amines, piperazine, phenylcyclohexyl-amine, choline, nitromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of the invention, their salts and solvates and prodrugs thereof, may exist in different tautomeric forms. All such forms are embraced and included within the scope of the invention, for example, ketone/enol tautomeric forms, imine-enamine tautomeric forms, and for example heteroaromatic forms such as the following moieties:

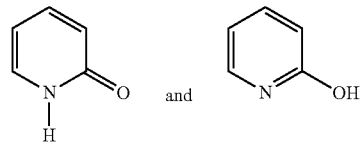 [SMILES: O=c1cccc[nH]1 ; Oc1ccccn1]

are considered equivalent in certain embodiments of this invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or other processes described herein or well known to the skilled artisan, and providing said compound in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When a variable (e.g., aryl, heterocycl, $R^3$, etc.) appears more than once in any moiety or in any compound of the invention, the selection of moieties defining that variable for each occurrence is independent of its definition at every other occurrence unless specified otherwise in the variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that may be preferentially incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively and other isotopes disclosed herein.

Certain isotopically-labeled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detection. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention may generally be prepared from precursor compounds prepared using procedures analogous to those disclosed in the Schemes and/or in the Examples herein below, by substituting an appropriate isotopically labeled reagent for a non-isotopically labeled reagent or using well-known schemes for the preparation of labeled compounds. It will be appreciated that other isotopes disclosed herein may also be used for such purposes.

In one aspect, as mentioned above, the present invention provides pharmaceutical formulations (pharmaceutical compositions) suitable for use in selectively blocking $Na_v1.7$ sodium channels found in sensory and sympathetic neurons, comprising at least one compound of Formula A:

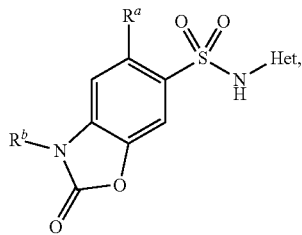

Formula A or a salt thereof,
wherein $R^a$, $R^b$, and "Het" are defined herein, and at least on pharmaceutically acceptable carrier (described below).

It will be appreciated that pharmaceutically formulations of the invention may comprise more than one compound of Formula A, for example, the combination of two or three compounds of Formula A, each present by adding to the formulation the desired amount of the compound in a pharmaceutically acceptably pure form. It will be appreciated that compositions of the invention may optionally comprise, in addition to one or more of the compounds of Formula A, one or more other compounds which also have pharmacological activity, for example, but not limited to: (i) an opiate agonist or antagonist; (ii) a calcium channel antagonist; (iii) an NMDA receptor agonist or antagonist; (iv) a COX-2 selective inhibitor; or (v) an NSAID (non-steroidal anti-inflammatory drug).

While formulations of the invention may be employed in bulk form, it will be appreciated that is some applications the inventive formulations may be incorporated into a dosage form suitable for administration to a patient, each dosage form comprising an amount of the selected formulation which contains an effective amount of said one or more compounds of Formula A. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachet or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions from the compounds described by this invention, generally pharmaceutically active compounds are combined with one or more pharmaceutically inactive excipients. These pharmaceutically inactive excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier".

Pharmaceutical compositions may be solid, semi-solid or liquid. Solid form preparations may be adapted to a variety of modes of administration and include powders, dispersible granules, mini-tablets, beads, and the like for example, for tableting, encapsulation, or direct administration. Typically formulations may comprise up to about 95 percent active ingredient, although formulations with greater amounts may be prepared.

Liquid form preparations include solutions, suspensions and emulsions. Examples of liquid forms of medicament include, but are not limited to, water or water/surfactant mixtures, for example a water-propylene glycol solution, which may be employed in the preparation of formulations intended, for example, for parenteral injection, for example, as a solvent or as a suspending medium for the preparation of suspensions and emulsions where a medicament comprises constituents which are insoluble in water or water/surfactant mixtures. Liquid form preparations may also include solutions for intranasal administration which may also include, for example, viscosity modifiers to adapt the formulation to target application of the formulation to particular mucosa tissues accessible via nasal administration.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension, solution, or a solution, for example, for oral or parenteral administration. Examples of such solid forms include freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions may take also the form of creams, lotions, aerosols and/or emulsions and may be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for treatment, management, prevention, alleviation or amelioration of conditions or disease states which may be treated, managed, prevented, alleviated or ameliorated by specific blocking of Nav 1.7 channel activity. Examples of this may include blocking neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associate with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain.

In accordance with the present invention, treatment, alleviation, amelioration, or management of a disease state amenable to blocking Na$_v$1.7 channel activity, for example a state of neuropathic pain, comprises administering to a patient in need thereof an effective amount of one or more compounds of Formula A, as defined herein, or a pharmaceutically acceptable salt of one or more compounds of Formula A, as defined herein. In some embodiments it may be preferred to effect a state of neuropathic pain disease by administering to a patient in need thereof of at least one compound of the invention defined herein.

As mentioned above, administration of a compound of Formula A in accordance with the present invention may be accomplished by incorporating the compound into a pharmaceutical formulation incorporated into a dosage form, for example, one of the above-described dosage forms comprising an effective amount of at least one compound of Formula A (e.g., 1, 2 or 3, or 1 or 2, or 1, and usually 1 compound of Formula A), or a pharmaceutically acceptable salt thereof, for example. Methods for determining safe and effective administration of compounds which are pharmaceutically active, for example, a compound of Formula A, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the instant invention may be administered at a total daily dosage of up to 1,000 mg, which may be administered in one daily dose or may be divided into two to four doses per day.

In general, in what ever form administered, the dosage form administered will contain an amount of at least one compound of Formula A, or a salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention, e.g., a compound of Formula A, may be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention may incorporate additional pharmaceutically active components or be administered simultaneously, contemporaneously, or sequentially with other pharmaceutically active compositions as may be additionally needed in the course of providing treatment. Such additional therapeutic agents may include, for example, i) opiate agonists or antagonists, ii) calcium channel antagonists, iii) NMDA receptor agonists or antagonists, iv) COX-2 selective inhibitors, and v) non-steroidal anti-inflammatory drugs ("NSAID").

Those skilled in the art will appreciate that treatment protocols utilizing at least one compound of Formula A may be varied according to the needs of the patient. Thus, compounds of Formula A used in the methods of this invention may be administered in variations of the protocols described above. For example, the compounds of this invention may be administered discontinuously rather than continuously during the treatment cycle.

The following examples are presented to further illustrate, but not limit the invention.

EXAMPLES

In general, compounds of the invention may be prepared by coupling an "alcohol precursor" which supplies the desired substituents for the "left-side" of the compound, or supplies a moiety having suitably reactive substituents which can be subsequently modified to provide the desired "left-side" portion of the compound, with a "core" precursor which supplies the "right side" of the compound, or contains suitably reactive substituents which can be subsequently modified to provide the desired "right-side" of the compound, as illustrated in Scheme Prep A:

In scheme Prep A, "$R^{bp}$" is either an alcohol form of the desired substituent "$R^b$", or is a precursor containing reactive substituents which can be modified in subsequent reactions to provide the desired substituent. As will be appreciated, "—$R^{cp}$" is either a protected sulfonamide substituent or another substituent which can provide the desired "—$SO_2NH$-Het" portion of the compound subsequent to the coupling procedure, for example, as illustrated below in Scheme 2 ($R^{cp}$ is a protected sulfonamide) or Scheme 16 ($R^{cp}$ is a protected sulfide). These schemes illustrate the scheme of Prep A by coupling, respectively, a protected sulfonamide-substituted "core" precursor or a thiol-substituted "core" precursor with an "alcohol precursor" under Mitsunobu reaction conditions mediated by diethylazodicarboxylate (DEAD). Thus, as illustrated in Scheme 2, below, a suitably substituted and protected "core" precursor (e.g., with reference to Scheme 2, compound 2-3) may be coupled to a suitable "alcohol precursor" (e.g., with reference to Scheme 2, compound 1-5) in the presence of polystyrene-bound triphenyl phosphine (PS-PPh$_3$) and DEAD to provide a compound of the invention (Scheme 2, compound 2-5)) after deprotection of the coupling product. Scheme 16, below, illustrates a variation of this by coupling a sulfide "core"-precursor compound (Scheme 16, cmpd 16-5) with a suitably protected "alcohol precursor" (Scheme 16, cmpd 1-5) using tributyl phosphine and DEAD, followed by a series of reaction steps which convert the sulfide moiety into a sulfonylchloride moiety (Scheme 16, cmpd 16-7) and subsequently reacting it with 2-amino-4-chloropyridine to provide a compound of the invention (Scheme 16, cmpd 16-8). Preparation of various precursors and other coupling and derivative reactions are presented in the Examples below which illustrate the preparation of various compounds of the invention.

Example 1

Preparation of (R)—N-(6-fluoropyridin-2-yl)-2-oxo-3-(1-(1,2,3,4-tetrahydroisoquinolin-8-yl)ethyl)-2,3-dihydrobenzo[d]oxazole-6-sulfonamide hydrochloride (2-5)

Scheme 1 illustrates the preparation of a suitable "alcohol precursor", tert-Butyl 8-[(1S)-1-hydroxyethyl]-3,4-dihydroisoquinoline-2(1H)-carboxylate (compound 1-5) from commercially available starting materials.

Prep A

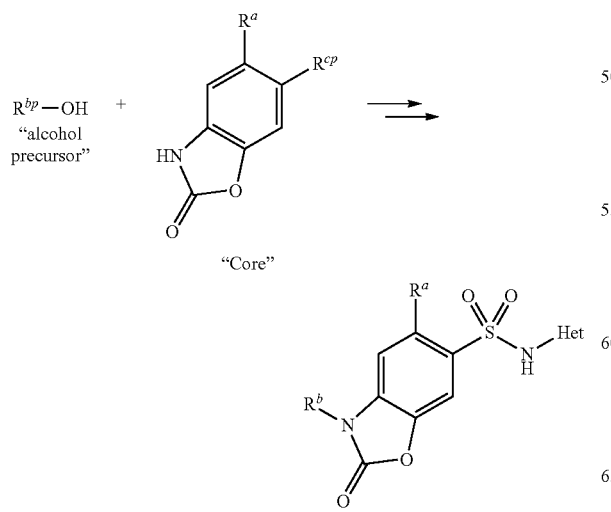

Scheme 1

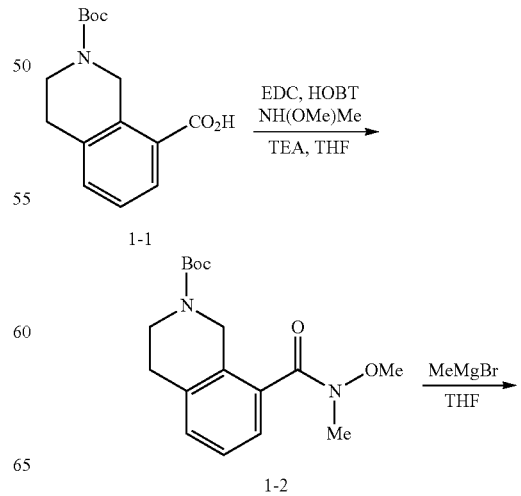

37

-continued

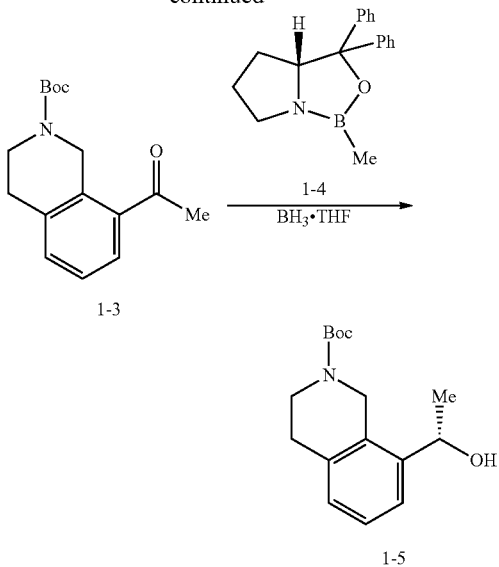

Preparation of tert-Butyl 8-[methoxy(methyl)-carbamoyl]-3,4-dihydroisoquinoline-2(1H)-carboxylate (1-2)

With reference to Scheme 1, 12.5 g of 1-1 (45.1 mmol, prepared from commercially available isoquinoline-8-carboxylic acid by literature methods) and 18.8 g triethylamine (135 mmol) were dissolved in 150 mL THF. This solution was treated with N,O-dimethylhydroxylamine hydrochloride (5.72 g, 58.6 mmol), followed by 1.73 g N-hydroxybenzotriazole (HOBT, 11.3 mmol) and 8.73 g ethyl-(N',N'-dimethylamino)propyl-carbodimide-hydrochloride (EDC, 45.5 mmol). The reaction was stirred overnight at RT. After removal of most of the solvent under reduced pressure, the residue was suspended in EtOAc (250 mL) and washed with 1N HCl (2×50 mL). The organic layer was washed with saturated sodium bicarbonate (2×50 mL), followed by brine. The organic layer was dried over sodium sulfate, filtered and concentrated. Purification by normal phase chromatography (0-50% EtOAc in hexane) yielded 1-2 (tert-Butyl 8-[methoxy(methyl)-carbamoyl]-3,4-dihydroisoquinoline-2(1H)-carboxylate) as a clear light yellow oil.

Preparation of tert-Butyl 8-acetyl-3,4-dihydroisoquinoline-2(1H)-carboxylate (1-3)

The compound of 1-2 previously prepared (1.26 g, 3.93 mmol) was dissolved in 39.3 mL THF and the solution was cooled to 0° C., then treated with a THF solution of methylmagnesium bromide (9.18 mL, 27.5 mmol). This reaction mixture was stirred at 0° C. for 4 hours, then quenched with saturated ammonium chloride (50 mL) and warmed to RT. The layers were split, the aqueous layer was back-extracted with EtOAc (3×75 mL) and the organic layers were combined, then washed with brine, dried over sodium sulfate, filtered and concentrated. The concentrate was purified by normal phase chromatography (0-50% EtOAc in hexane) yielding the compound of Formula 1-3 (tert-Butyl 8-acetyl-3,4-dihydroisoquinoline-2(1H)-carboxylate) as a colorless oil, used without further purification in the next step.

38

Preparation of tert-Butyl 8-[(1S)-1-hydroxyethyl]-3,4-dihydroisoquinoline-2(1H)-carboxylate (1-5)

Into an oven-dried 1-dram vial containing 224 microliters of anhydrous THF (RT) was added 24.7 mg of the compound of Formula 1-3 (previously prepared, 0.090 mmol) and 17.94 µl of (3aR)-1-methyl-3,3-diphenyltetrahydro-3H-pyrrolo[1,2-c][1,3,2]oxazaborole (1-4, 0.018 mmol). Into the reaction mixture thus provided was added (via 500 µL air-tight syringe) 90 µL BH$_3$-THF (0.090 mmol) in 224 µL anhydrous THF, dropwise over 20 min followed by a 50 µL anhydrous THF rinse. After an additional 30 min LCMS analysis showed complete consumption of starting material. The reaction mixture was cautiously quenched with 2M HCl (3 mL) and diluted with EtOAc (5 mL). The layers were separated and the aqueous layer was back-extracted with EtOAc (3×3 mL). The combined organics were dried over Na$_2$SO$_4$, filtered and concentrated to give a white solid. Chiral separation (ChiralPak AD-H) provided the compound of Formula 1-5 (tert-Butyl 8-[(1S)-1-hydroxyethyl]-3,4-dihydroisoquinoline-2(1H)-carboxylate).

Scheme 2 illustrates first preparation of a suitable "core" precursor (Compound 2-3) and its conversion to Compound 2-5, a compound of the invention.

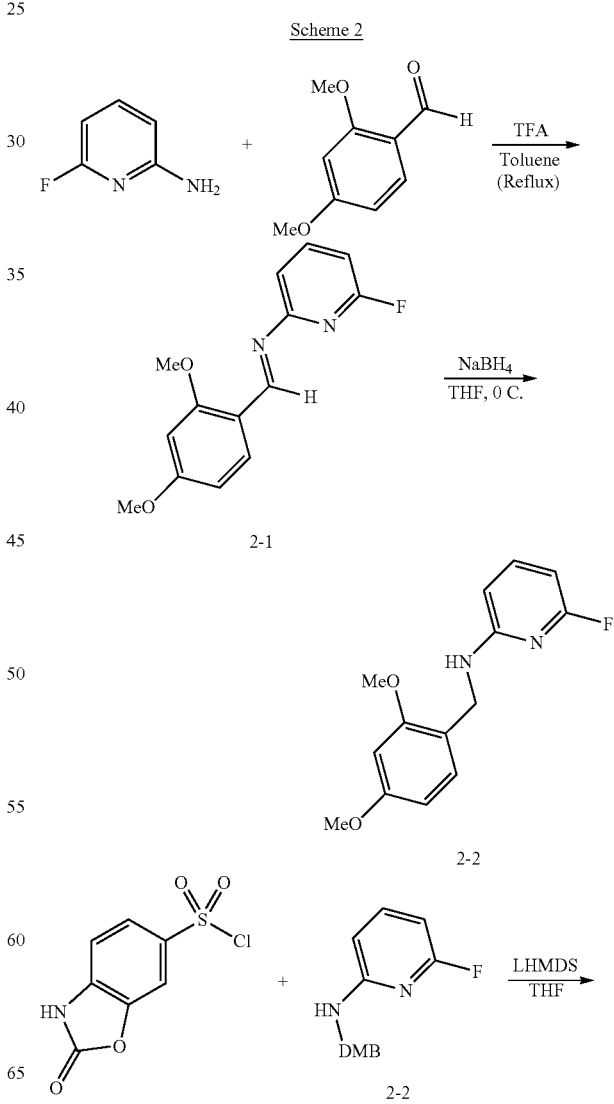

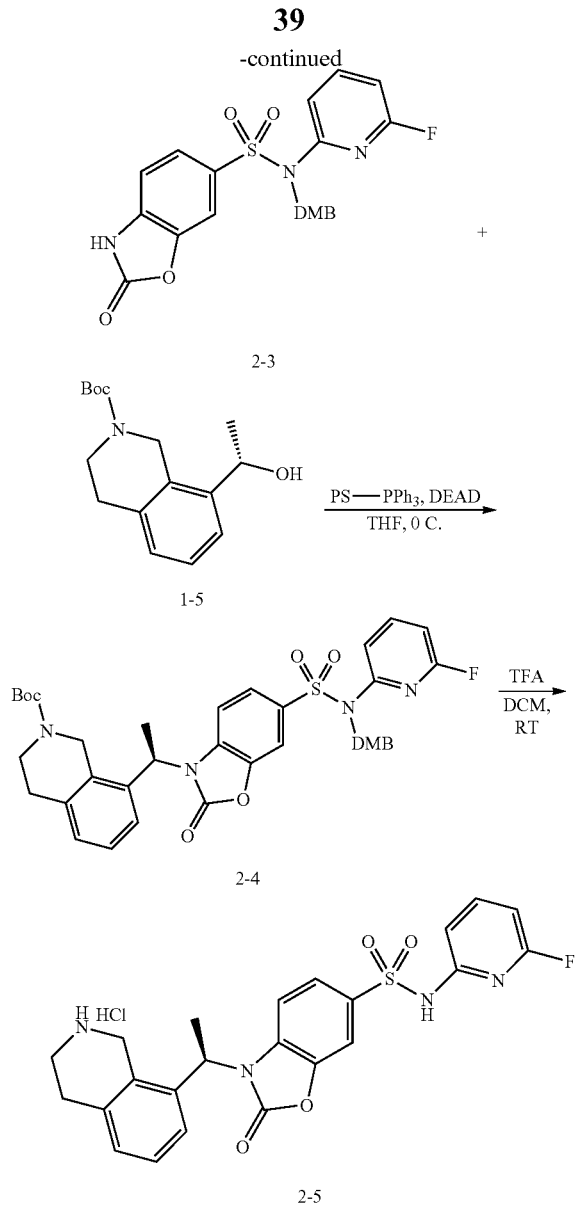

N-(2,4-dimethoxybenzylidene)-6-fluoropyridin-2-amine (2-1)

To a flask containing commercially available 2-Amino-6-fluoropyridine (10.2 g, 91 mmol) & commercially available 2,4-dimethoxybenzaldehyde (15.4 g, 93 mmol) was added anhydrous toluene (300 mL), then TFA (1 ml, 12.98 mmol). The reaction mixture was then heated to 135° C. while stirring in the hood with an water cooled reflux condenser attached to a Dean Stark trap. Followed by LC/MS. Heated overnight, then cooled to room temperature, then concentrated to yield crude N-(2,4-dimethoxybenzylidene)-6-fluoropyridin-2-amine (2-1).

N-(2,4-dimethoxybenzyl)-6-fluoropyridin-2-amine (2-2)

To a flask containing crude N-(2,4-dimethoxybenzylidene)-6-fluoropyridin-2-amine (2-1) (20.5 g, 79 mmol) in anhydrous THF (120 mL) was cooled to 0° C. (ice water bath) then added NaBH$_4$ (8.94 g, 236 mmol) as a solid in one portion. Stirred at 0° C. (capped, but not under N$_2$). Followed by LC/MS. After 2.5 hours the reaction mixture was uncapped & quenched by addition of saturated NaHCO$_3$ (slowly) at 0° C. (lots of bubbling/gas evolution), then the reaction mixture was suspended in EtOAc, washed with saturated NaHCO$_3$, then filtered to remove the precipitate, the filtrate was then separated, then the organics were washed with saturated NaHCO$_3$, then water, then brine; the organics were dried over Na$_2$SO$_4$, filtered & concentrated. Purification by silica gel chromatography (0-40% EtOAc/Hex; 330 g ISCO); desired fractions concentrated to yield N-(2,4-dimethoxybenzyl)-6-fluoropyridin-2-amine (2-2). HRMS [M+H]: calculated; 263.1190, observed; 263.1184.

N-(2,4-dimethoxybenzyl)-N-(6-fluoropyridin-2-yl)-2-oxo-2,3-dihydrobenzo[d]oxazole-6-sulfonamide (2-3)

To a flask was added N-(2,4-dimethoxybenzyl)-6-fluoropyridin-2-amine (2-2) (1.29 g, 4.92 mmol), then anhydrous THF (10 mL). The reaction mixture was stirred and cooled to -78° C. (dry ice/acetone) under N$_2$. Then a 1M solution of LHMDS in THF (9 mL, 9.00 mmol) was added dropwise and left to stir for 10 min at -78 C. The reaction mixture was then warmed to room temperature and left to stir for 30 min, then cooled back to -78° C. To this solution was added commercially available 2-oxo-2,3-dihydrobenzo[d]oxazole-6-sulfonyl chloride (773 mg, 3.31 mmol) at -78° C., the reaction mixture was permitted to stir at -78° C. (under N$_2$) for 10 minutes, then warmed to room temperature. Followed by LC/MS. After 30 min at room temperature the reaction mixture was quenched with saturated NaHCO$_3$, then water, then diluted with EtOAc, organics separated, then washed with water, then brine; dried over Na$_2$SO$_4$, filtered & concentrated. The resulting residue was dissolved in DCM & purified by silica gel chromatography (0-100% EtOAc/Hex; 120 g ISCO); desired fractions concentrated to yield N-(2,4-dimethoxybenzyl)-N-(6-fluoropyridin-2-yl)-2-oxo-2,3-dihydrobenzo[d]oxazole-6-sulfonamide (2-3). HRMS [M+H]: calculated; 460.0973, observed; 460.0959.

(R)-tert-butyl 8-(1-(6-(N-(2,4-dimethoxybenzyl)-N-(6-fluoropyridin-2-yl)sulfamoyl)-2-oxobenzo[d]oxazol-3(2H)-yl)ethyl)-3,4-dihydroisoquinoline-2(1H)-carboxylate (2-4)

To a vial containing N-(2,4-dimethoxybenzyl)-N-(6-fluoropyridin-2-yl)-2-oxo-2,3-dihydrobenzo[d]oxazole-6-sulfonamide (2-3) (282 mg, 0.614 mmol), resin bound (PS) triphenylphosphine (661 mg, 1.42 mmol), was added anhydrous THF (5 mL), followed by DEAD (0.225 mL, 1.418 mmol). The reaction mixture was then cooled to 0° C. (ice water bath) (capped, but not under N$_2$), then added (S)-tert-butyl 8-(1-hydroxyethyl)-3,4-dihydroisoquinoline-2(1H)-carboxylate (1-5) (304 mg, 1.10 mmol) as a solid in 1 portion. The reaction mixture (clear tan & solid resin) was then continued to stir at 0° C. (never warmed to room temperature). Followed by LC/MS. After 2 hrs at 0° C. (still some R1/R2 remained; seemed to stall); the reaction mixture was filtered (to remove resin), then concentrated. This material was dissolved in DMSO/MeOH then purified by reverse phase chromatography (10-100% MeCN/water; 0.1% TFA in AQ; 20 min gradient; Waters 30×150 mm Sunfire 5 micron C18 column); desired fractions were free based (suspended in EtOAc, washed with saturated NaHCO$_3$, then water, then brine); organics dried over Na$_2$SO$_4$, filtered & concentrated to yield (R)-tert-butyl 8-(1-(6-(N-(2,4-dimethoxybenzyl)-N-(6-fluoropyridin-2-yl)sulfamoyl)-2-oxobenzo[d]oxazol-3(2H)-yl)ethyl)-3,4-dihydroisoquinoline-2(1H)-carboxylate (2-4). HRMS [M+H]: calculated; 719.2545, observed; 719.2517.

(R)—N-(6-fluoropyridin-2-yl)-2-oxo-3-(1-(1,2,3,4-tetrahydroisoquinolin-8-yl)ethyl)-2,3-dihydrobenzo[d]oxazole-6-sulfonamide hydrochloride (2-5)

To a flask containing (R)-tert-butyl 8-(1-(6-(N-(2,4-dimethoxybenzyl)-N-(6-fluoropyridin-2-yl)sulfamoyl)-2-oxobenzo[d]oxazol-3(2H)-yl)ethyl)-3,4-dihydroisoquinoline-2(1H)-carboxylate (2-4) (135 mg, 0.188 mmol) in DCM (5 mL) was added TFA (0.5 mL, 6.49 mmol). The reaction mixture was then stirred at room temperature open to the atmosphere. Followed by LC/MS. After 20 minutes the reaction mixture was diluted/quenched with DMSO, then filtered (syringe filter) then concentrated (to remove DCM), then diluted with MeOH/DMSO & filtered again (syringe filter) then the filtrate was purified (without workup) by reverse phase chromatography (5-70% MeCN/water; 0.1% TFA in AQ; 20 min gradient; Waters 30×150 mm Sunfire 5 micron C18 column); desired fractions concentrated, then dissolved in MeOH/DCM & added a saturated solution of HCl in EtOAc (~4N) & concentrated to yield (R)—N-(6-fluoropyridin-2-yl)-2-oxo-3-(1-(1,2,3,4-tetrahydroisoquinolin-8-yl)ethyl)-2,3-dihydrobenzo[d]oxazole-6-sulfonamide hydrochloride (2-5). HRMS [M+H]: calculated; 469.1340, observed; 469.1329. $^1$H NMR (400 MHz, CD$_3$ OD): δ 7.87 (d, J=1.8 Hz, 1H); 7.78 (d, J=8.2 Hz, 1H); 7.76-7.70 (m, 2H); 7.50-7.44 (m, 1H); 7.31 (d, J=7.7 Hz, 1H); 7.06 (d, J=8.4 Hz, 1H); 6.97 (dd, J=7.9, 2.0 Hz, 1H); 6.58 (dd, J=8.0, 2.5 Hz, 1H); 5.75-5.66 (m, 1H); 4.47 (d, J=15.7 Hz, 1H); 4.12 (d, J=15.7 Hz, 1H); 3.49-3.40 (m, 1H); 3.37-3.31 (m, 1H); 3.21-3.03 (m, 2H); 1.90 (d, J=7.0 Hz, 3H).

Example 2

Preparation of (R)-5-fluoro-N-(6-fluoropyridin-2-yl)-2-oxo-3-(1-(1,2,3,4-tetrahydroisoquinolin-8-yl)ethyl)-2,3-dihydrobenzo[d]oxazole-6-sulfonamide hydrochloride (3-5)

Scheme 3 illustrates first preparation of a suitable fluoro-substituted "core" precursor (Compound 3-3) and its conversion to Compound 3-5, a compound of the invention.

Scheme 3

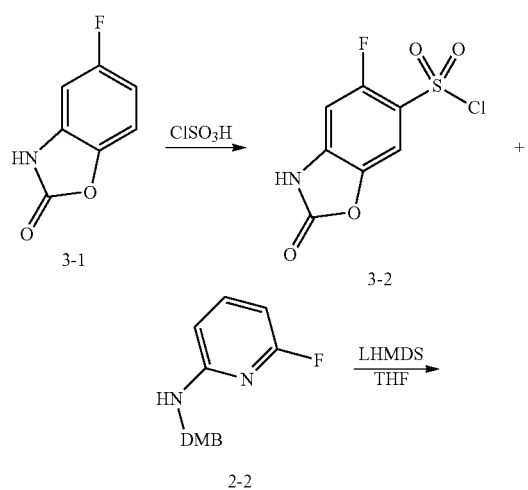

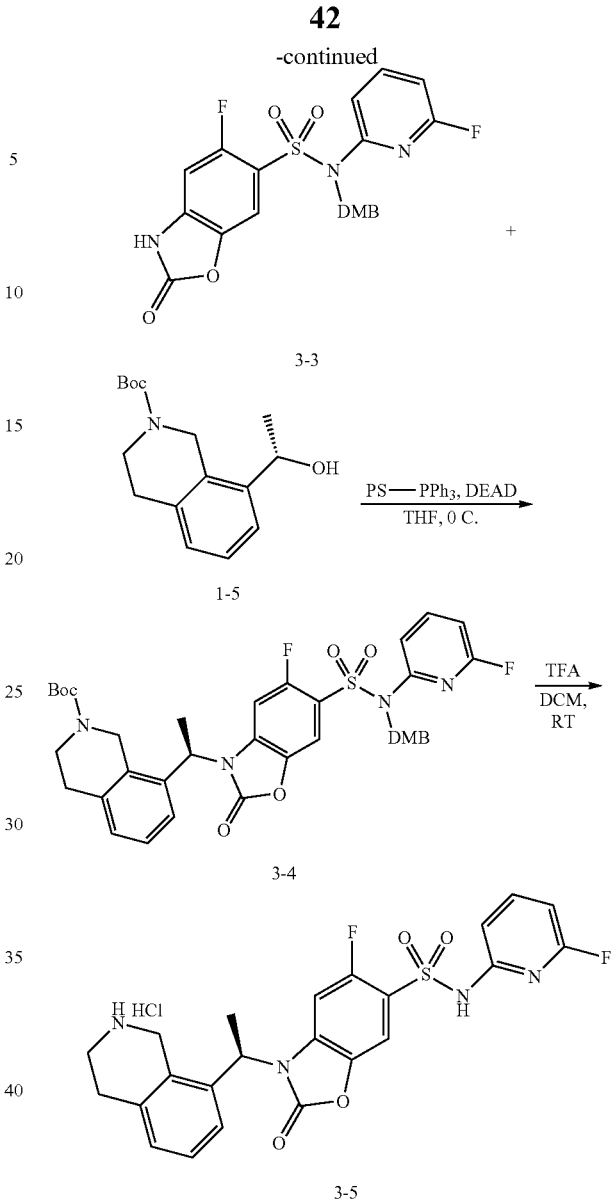

Preparation of 5-Fluoro-2-oxo-2,3-dihydro-1,3-benzoxazole-6-sulfonyl chloride (3-2)

A mixture of commercially-available 5-fluoro-1,3-benzoxazol-2(3H)-one (3-1, 1.02 g, 6.66 mmol) in DCM (66.6 mL) at RT was added chlorosulfonic acid (4.46 mL, 66.6 mmol). The suspension gradually became a solution and was stirred for 18 h at RT. Following this duration, LCMS showed complete consumption of starting material. The solution was cooled to 0° C. and carefully quenched with ice chips and then partitioned between water (100 mL) and EtOAc (100 mL). The layers were separated and the aqueous layer was back-extracted with 3×20 mL DCM and 2×20 mL EtOAc. The combined organic layers were washed with saturated aqueous NaHCO$_3$ (30 mL), dried over sodium sulfate and filtered. Concentration in vacuo to yield 3-2 (5-Fluoro-2-oxo-2,3-dihydro-1,3-benzoxazole-6-sulfonyl chloride), which was used without purification.

Compound 3-2 was reacted with dimethoxybenzene-protected 2-amino-6-fluoro pyridine (Compound 2-2) under the same conditions employed in Scheme 2 for the preparation of Compound 2-3, to provided N-(2,4-dimethoxybenzyl)-5- fluoro-N-(6-fluoropyridin-2-yl)-2-oxo-2,3-dihydrobenzo[d]oxazole-6-sulfonamide (Compound 3-3), the 5-fluoro analog of Compound 2-3 prepared in the same manner in Scheme 2.

Preparation of (R)-5-fluoro-N-(6-fluoropyridin-2-yl)-2-oxo-3-(1-(1,2,3,4-tetrahydroisoquinolin-8-yl)ethyl)-2,3-dihydrobenzo[d]oxazole-6-sulfonamide hydrochloride (3-5)

To a flask containing (R)-tert-butyl 8-(1-(6-(N-(2,4-dimethoxybenzyl)-N-(6-fluoropyridin-2-yl)sulfamoyl)-5-fluoro-2-oxobenzo[d]oxazol-3(2H)-yl)ethyl)-3,4-dihydroisoquinoline-2(1H)-carboxylate (3-4) (221 mg, 0.300 mmol) (which was prepared from compound 3-3 and Compound 1-5 using an analogous to the sequence described in Scheme 2) in DCM (5 mL) was added TFA (0.8 mL, 10.4 mmol). The reaction mixture was then stirred at room temperature open to the atmosphere. Followed by LC/MS. After 20 minutes the reaction mixture was diluted/quenched with DMSO, then filtered (syringe filter), then concentrated (to remove DCM), then diluted with MeOH/DMSO & filtered again (syringe filter), then the filtrate was purified (without workup) by reverse phase chromatography (5-75% MeCN/water; 0.1% TFA in AQ; 20 min gradient; Waters 30×150 mm Sunfire 5 micron C18 column); desired fractions concentrated, then dissolved in MeOH/DCM & added a saturated solution of HCl in EtOAc (~4N) & concentrated to yield (R)-5-fluoro-N-(6-fluoropyridin-2-yl)-2-oxo-3-(1-(1,2,3,4-tetrahydroisoquinolin-8-yl)ethyl)-2,3-dihydrobenzo[d]oxazole-6-sulfonamide hydrochloride (3-5). HRMS [M+H]: calculated; 487.1246, observed; 487.1239. $^1$H NMR (400 MHz, CD$_3$OD): δ 7.85 (d, J=5.7 Hz, 1H); 7.76-7.66 (m, 2H); 7.43 (t, J=7.8 Hz, 1H); 7.28 (d, J=7.8 Hz, 1H); 6.88 (dd, J=7.9, 2.0 Hz, 1H); 6.82 (d, J=9.8 Hz, 1H); 6.55 (dd, J=8.0, 2.5 Hz, 1H); 5.65 (q, J=7.0 Hz, 1H); 4.44 (d, J=15.7 Hz, 1H); 4.11 (d, J=15.7 Hz, 1H); 3.46-3.37 (m, 1H); 3.35-3.30 (m, 1H); 3.14-2.99 (m, 2H); 1.85 (d, J=7.0 Hz, 3H).

Example 3

Preparation of Preparation of 3-(7-amino-1,2,3,4-tetrahydronaphthalen-1-yl)-5-fluoro-N-(6-fluoropyridin-2-yl)-2-oxo-2,3-dihydro-1,3-benzoxazole-6-sulfonamide (Compound 4-4)

Scheme 4 illustrates first preparation of a suitably functionalized "alcohol precursor" (Compound 4-2) and its use in preparation of Compound 4-4 by a reaction sequence analogous to that shown in Examples 1 and 2.

Scheme 4

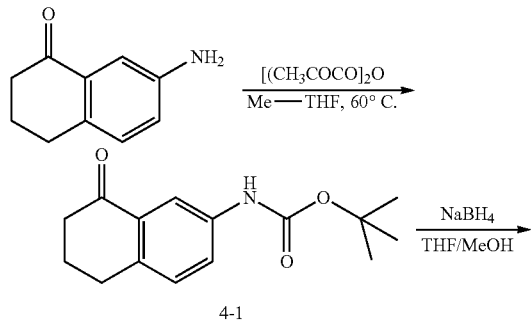

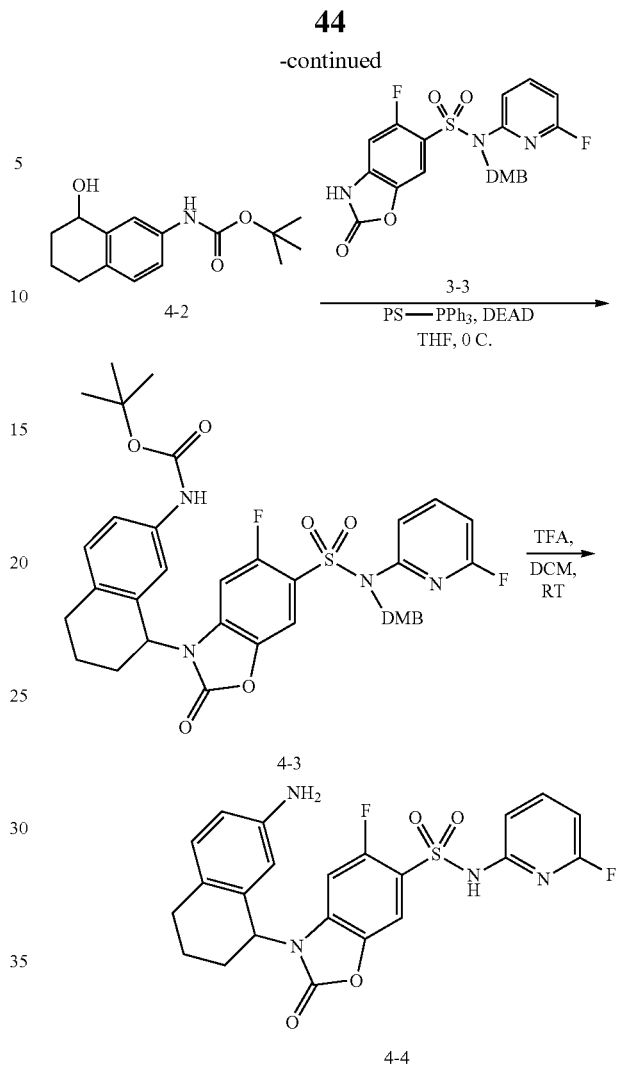

Preparation of tert-butyl (8-oxo-5,6,7,8-tetrahydronaphthalen-2-yl)carbamate (4-1)

To a solution of 7-amino-3,4-dihydronaphthalen-1(2H)-one (500 mg, 3.10 mmol) in Me-THF (15 mL) was added Di-t-butyl dicarbonate (812 mg, 3.72 mmol) and warmed to 60° C. for 16 hours. Reaction is concentrated in vacuo and the resulting residue is purified by normal phase chromatography (10-30% EtOAc in hexane) to yield the compound of Formula 4-1 as a solid.

Preparation of tert-butyl (8-hydroxy-5,6,7,8-tetrahydronaphthalen-2-yl)carbamate (4-2)

To a solution of the compound of Formula 4-1 (740 mg, 2.83 mmol) in THF (5 mL)/MeOH (5 mL) was added sodium borohydride (107 mg, 2.83 mmol) while cooled at 0° C. The solution was stirred for 1 hour and concentrated to ¼ volume in vacuo. The residue was diluted with EtOAc (40 mL) and washed with sat'd sodium bicarbonate (2×10 mL) and brine (10 mL). Organics were dried over sodium sulfate, filtered, and concentrated in vacuo to yield the compound of Formula 4-2 as a solid.

Preparation of 3-(7-Amino-1,2,3,4-tetrahydronaphthalen-1-yl)-5-fluoro-N-(6-fluoropyridin-2-yl)-2-oxo-2,3-dihydro-1,3-benzoxazole-6-sulfonamide (4-4)

Sulfonamide 4-4 was prepared from alcohol 4-2 and benzoxazolinone 3-3 by a sequence analogous to that illustrated in Scheme 3. HRMS [M+H]: calculated; 473.1, observed; 473.0.

The compound illustrated in Table 1 was prepared from benzoxazolinone 3-3 and the appropriate alcohol in accordance with the synthetic sequence depicted in Scheme 4:

TABLE 1

| Ex-No. | Structure | Name | Exact Mass [M + H]+ |
|---|---|---|---|
| 4-5 | 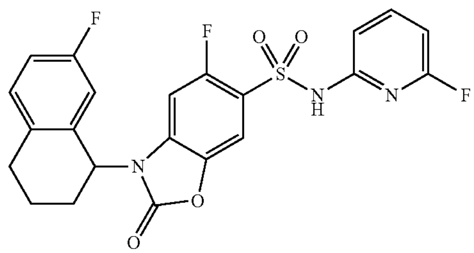 [SMILES: O=c1oc2cc(S(=O)(=O)Nc3cccc(F)n3)c(F)cc2n1C1CCCc2ccc(F)cc21] | 5-fluoro-N-(6-fluoropyridin-2-yl)-3-(7-fluoro-1,2,3,4-tetrahydronaphthalen-1-yl)-2-oxo-2,3-dihydro-1,3-benzoxazole-6-sulfonamide | Calc'd 476.1, found 475.9 |

Example 4

Preparation of 5-fluoro-3-((4-fluoro-1,2,3,4-tetrahydroisoquinolin-8-yl)methyl)-N-(6-fluoropyridin-2-yl)-2-oxo-2,3-dihydrobenzo[d]oxazole-6-sulfonamide hydrochloride (Compound 5-9)

Scheme 5 illustrates first preparation of a suitably functionalized "alcohol precursor" (Compound 5-7) and its use in preparation of compounds of the invention by reaction with Compound 3-3 (prepared in Example 2 above) using a reaction sequence analogous to that shown in Examples 1 and 2.

Scheme 5

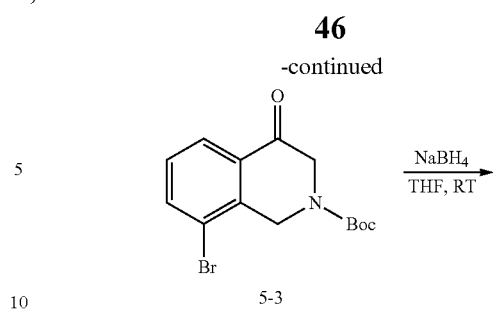

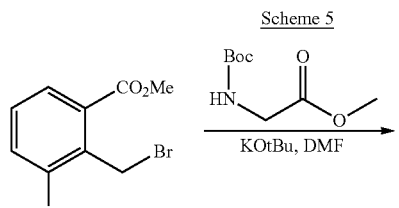

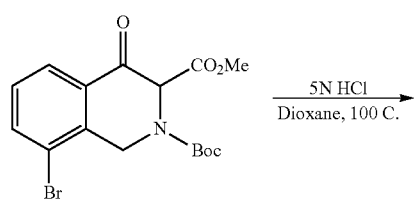

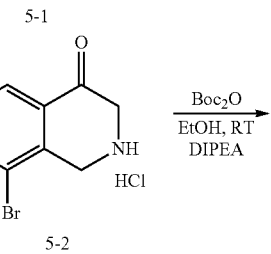

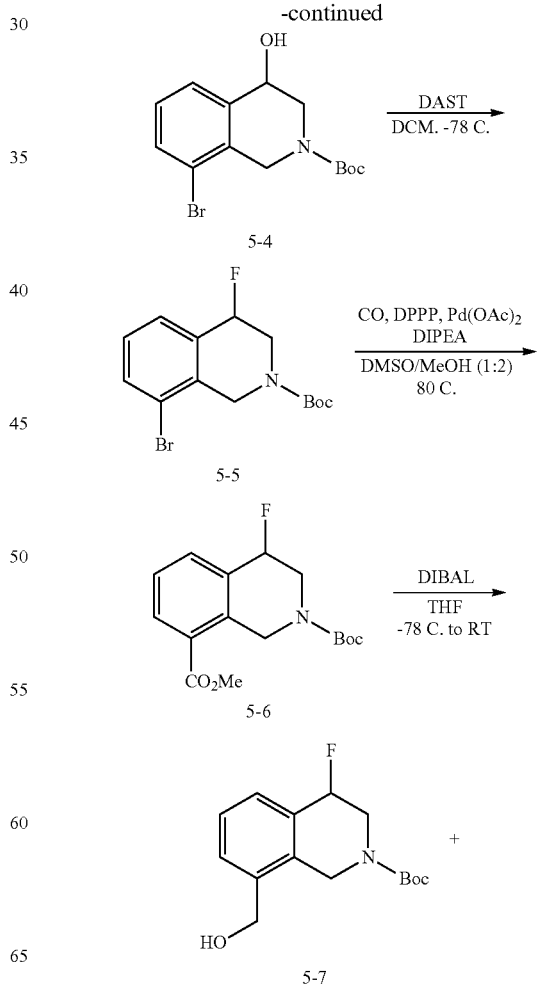

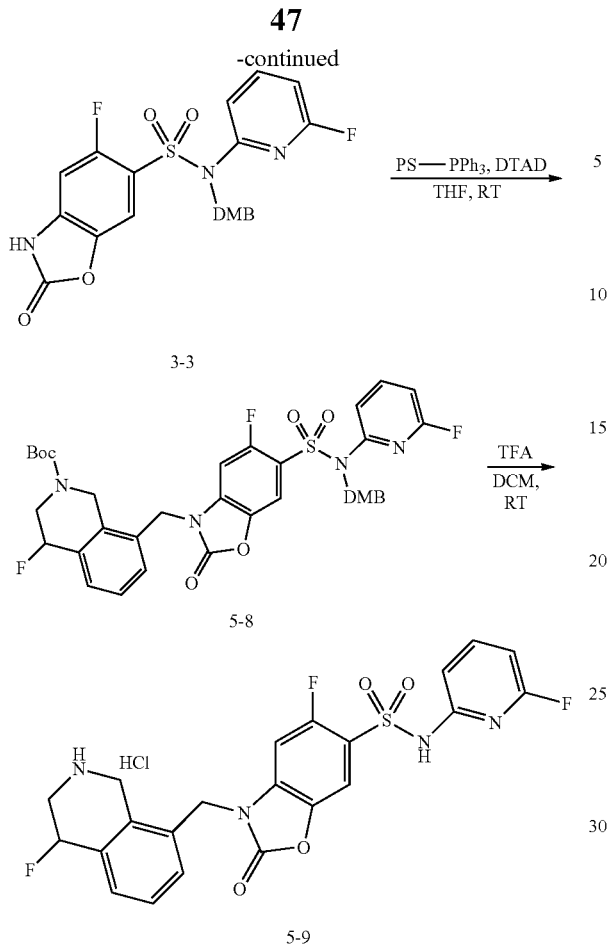

Preparation of 2-tert-Butyl 3-methyl 8-bromo-4-oxo-3,4-dihydroisoquinoline-2,3(1H)-dicarboxylate (5-1)

To a flask containing methyl 2-((tert-butoxycarbonyl)amino)acetate (4.18 g, 22.09 mmol) in anhydrous DMF (50 mL) was added KOtBu (3.99 g, 35.6 mmol) then after 1 min at room temperature added methyl 3-bromo-2-(bromomethyl)benzoate (4.97 g, 16.14 mmol) as a solid in 1 portion. The reaction mixture was then capped (not under $N_2$) & stirred at room temperature for 3 hours. Followed by LC/MS. The reaction mixture was quenched/diluted with sat'd $NaHCO_3$, then suspended in EtOAc, washed with saturated $NaHCO_3$, then water, then brine; organics dried over $Na_2SO_4$, filtered & concentrated. Purification by silica gel chromatography (0-20% EtOAc/Hex; 220 g ISCO); desired fractions concentrated to yield 2-tert-butyl 3-methyl 8-bromo-4-oxo-3,4-dihydroisoquinoline-2,3(1H)-dicarboxylate (5-1).

Preparation of 8-Bromo-2,3-dihydroisoquinolin-4(1H)-one hydrochloride (5-2)

To a flask containing 2-tert-butyl 3-methyl 8-bromo-4-oxo-3,4-dihydroisoquinoline-2,3(1H)-dicarboxylate (5-1) (3.44 g, 8.95 mmol) (mixed with impurities) was added was added Dioxane (20 mL), then 5N HCl in water (20 mL, 100 mmol). The reaction mixture was then heated to 90° C. in the hood overnight. Followed by LC/MS. The next morning another 20 mL of 5N HCl was added and the reaction mixture was heated to 110° C. for 3 hours, then was concentrated. The resulting residue was triturated with DCM (hot, then cooled to room temperature) & filtered to yield 8-bromo-2,3-dihydroisoquinolin-4(1H)-one hydrochloride (5-2). HRMS [M+H]: calculated; 225.9862, observed; 225.9860.

Preparation of tert-Butyl 8-bromo-4-oxo-3,4-dihydroisoquinoline-2(1H)-carboxylate (5-3)

To a flask containing 8-bromo-2,3-dihydroisoquinolin-4(1H)-one hydrochloride (5-2) (1.29 g, 4.92 mmol) was added Ethanol (20 mL), then $Boc_2O$, then DIPEA (2 mL, 11.5 mmol). The reaction mixture was then capped (not under $N_2$) & stirred at room temperature. Followed by LC/MS. After 45 minutes the reaction mixture was suspended in EtOAc, washed with saturated $NaHCO_3$, then water, then brine; organics dried over $Na_2SO_4$, filtered & concentrated. Purification by silica gel chromatography (0-20%, then isocratic at 10% when $1^{st}$ peak elutes; EtOAc/Hex; 120 g ISCO); desired fractions concentrated to yield tert-butyl 8-bromo-4-oxo-3,4-dihydroisoquinoline-2(1H)-carboxylate (5-3).

Preparation of tert-Butyl 8-bromo-4-hydroxy-3,4-dihydroisoquinoline-2(1H)-carboxylate (5-4)

To a flask containing tert-butyl 8-bromo-4-oxo-3,4-dihydroisoquinoline-2(1H)-carboxylate (5-3) (644 mg, 1.974 mmol) was added anhydrous THF (5 mL), followed by $NaBH_4$ (399 mg, 10.55 mmol). The reaction mixture was then capped (not under $N_2$) & stirred at room temperature. Followed by LC/MS. After 10 minutes the reaction mixture was quenched with saturated $NaHCO_3$, then suspended in EtOAc, washed with saturated $NaHCO_3$, then water, then brine; organics dried over $Na_2SO_4$, filtered & concentrated. Purification by silica gel chromatography (0-50% EtOAc/Hex; 40 g ISCO); desired fractions concentrated to yield tert-butyl 8-bromo-4-hydroxy-3,4-dihydroisoquinoline-2(1H)-carboxylate (5-4). HRMS [M+H]: calculated; 328.0543, observed; 328.0537.

Preparation of tert-Butyl 8-bromo-4-fluoro-3,4-dihydroisoquinoline-2(1H)-carboxylate (5-5)

To a flask containing tert-butyl 8-bromo-4-hydroxy-3,4-dihydroisoquinoline-2(1H)-carboxylate (5-4) (622 mg, 1.89 mmol) was added anydrous DCM (10 mL). The reaction mixture was then capped & cooled to −78° C. (dry ice/acetone bath) while stirring under $N_2$. Then added DAST (1.4 mL, 10.6 mmol) at −78° C. The reaction mixture was then stirred at −78° C. Followed by LC/MS. After 5 minutes at −78° C. the reaction was quenched by dropwise addition of a saturated solution of $NaHCO_3$ in water at −78° C. (with a vent needle), then permitted to warm to room temperature, then the reaction mixture was suspended in EtOAc, washed with saturated $NaHCO_3$, then water, then brine; organics dried over $Na_2SO_4$, filtered & concentrated to yield. Purification by silica gel chromatography (0-15% EtOAc/Hex; 40 g ISCO); desired fractions concentrated to yield tert-butyl 8-bromo-4-fluoro-3,4-dihydroisoquinoline-2(1H)-carboxylate (5-5).

Preparation of 2-tert-Butyl 8-methyl 4-fluoro-3,4-dihydroisoquinoline-2,8(1H)-dicarboxylate (5-6)

To a flask containing tert-butyl 8-bromo-4-fluoro-3,4-dihydroisoquinoline-2(1H)-carboxylate (5-5) (316 mg, 0.957 mmol) was added triethylamine (0.6 mL, 4.30 mmol), followed by degassed anhydrous MeOH (6 mL) & DMSO (3 mL). This mixture was then degassed by bubbling $N_2$ through with a vent needle while stirring for 5 minutes. Then added $PdOAc_2$ (57 mg, 0.254 mmol) & DPPP (83 mg, 0.201 mmol) as solids in 1 portion. A balloon containing carbon monoxide (536 mg, 19.14 mmol) was then attached and the reaction was purged 3× (vacuum/CO), then the reaction mixture (clear tan, became darker with heat) was heated to 80° C. while stirring in a hot oil bath in the hood under an atmosphere of CO. Followed by LC/MS. After 22 hours, the reaction mixture was suspended in EtOAc, washed with saturated $NaHCO_3$, then water, then brine; organics dried over $Na_2SO_4$, filtered & concentrated. Purification by silica gel chromatography (0-40% EtOAc/Hex; 40 g ISCO); desired fractions concentrated to yield 2-tert-butyl 8-methyl 4-fluoro-3,4-dihydroisoquinoline-2,8(1H)-dicarboxylate (5-6). HRMS [M+H]: calculated; 310.1449, observed; 310.1439.

Preparation of tert-Butyl 4-fluoro-8-(hydroxymethyl)-3,4-dihydroisoquinoline-2(1H)-carboxylate (Compound 5-7)

To a flask containing 2-tert-butyl 8-methyl 4-fluoro-3,4-dihydroisoquinoline-2,8(1H)-dicarboxylate (5-6) (214 mg, 0.692 mmol), was added anhydrous THF (3.5 mL) then cooled to −78° C. (dry ice/acetone bath) while stirring under an atmosphere of $N_2$. Then added DIBAL-H (2.4 mL, 2.400 mmol) dropwise. The reaction mixture was then stirred at −78° C. for 20 minutes, then warmed to room temperature. Followed by LC/MS. After 10 minutes at room temperature quenched by dropwise addition of saturated solution of Rochelle's Salt (Na+/K+ Tartrate) in water, then suspended in EtOAc, washed with saturated $NaHCO_3$, then water, then brine; organics dried over $Na_2SO_4$, filtered & concentrated. Purification by silica gel chromatography (0-40%; isocratic @30% EtOAc/Hex; 24 g ISCO); desired fractions concentrated to yield tert-butyl 4-fluoro-8-(hydroxymethyl)-3,4-dihydroisoquinoline-2(1H)-carboxylate (5-7). HRMS [M+H]; calculated; 282.1500, observed; 282.1491.

Preparation of tert-Butyl 8-((6-(N-(2,4-dimethoxybenzyl)-N-(6-fluoropyridin-2-yl)sulfamoyl)-5-fluoro-2-oxobenzo[d]oxazol-3(2H)-yl)methyl)-4-fluoro-3,4-dihydroisoquinoline-2(1H)-carboxylate (5-8)

To a flask containing N-(2,4-dimethoxybenzyl)-5-fluoro-N-(6-fluoropyridin-2-yl)-2-oxo-2,3-dihydrobenzo[d]oxazole-6-sulfonamide (3-3) (130 mg, 0.272 mmol), resin bound (PS resin) triphenylphosphine (247 mg, 0.543 mmol), tert-butyl 4-fluoro-8-(hydroxymethyl)-3,4-dihydroisoquinoline-2(1H)-carboxylate (5-7) (85 mg, 0.302 mmol) & di-tert-butyl azodicarboxylate (137 mg, 0.595 mmol) was added THF (3 mL). The reaction mixture was then capped (not under $N_2$) & stirred at room temperature. Followed by LC/MS. After 10 minutes the reaction mixture was filtered (to remove resin), then the filtrate was concentrated. Purification by silica gel chromatography (0-50% EtOAc/Hex; 40 g ISCO); desired fractions were concentrated to yield tert-butyl 8-((6-(N-(2,4-dimethoxybenzyl)-N-(6-fluoropyridin-2-yl)sulfamoyl)-5-fluoro-2-oxobenzo[d]oxazol-3(2H)-yl)methyl)-4-fluoro-3,4-dihydroisoquinoline-2(1H)-carboxylate (5-8).

Preparation of (+/−)-5-Fluoro-3-((4-fluoro-1,2,3,4-tetrahydroisoquinolin-8-yl)methyl)-N-(6-fluoropyridin-2-yl)-2-oxo-2,3-dihydrobenzo[d]oxazole-6-sulfonamide hydrochloride (5-9)

To a flask containing tert-butyl 8-((6-(N-(2,4-dimethoxybenzyl)-N-(6-fluoropyridin-2-yl)sulfamoyl)-5-fluoro-2-oxobenzo[d]oxazol-3(2H)-yl)methyl)-4-fluoro-3,4-dihydroisoquinoline-2(1H)-carboxylate (5-8) (101 mg, 0.136 mmol) in DCM (3 mL) was added TFA (0.5 mL, 6.49 mmol). The reaction mixture was then stirred at room temperature open to the atmosphere. Followed by LC/MS. After 20 minutes the reaction mixture was diluted/quenched with DMSO, then MeOH, then filtered (syringe filter), the filtrate was then concentrated (to remove DCM), then diluted with MeOH/DMSO & purified (without workup) by reverse phase chromatography (5-75% MeCN/water; 0.1% TFA in AQ; 20 min gradient; Waters 30×150 mm Sunfire 5 micron C18 column); desired fractions concentrated, then dissolved in MeOH/DCM & added saturated HCl in EtOAc (~4N) & concentrated to yield 5-fluoro-3-((4-fluoro-1,2,3,4-tetrahydroisoquinolin-8-yl)methyl)-N-(6-fluoropyridin-2-yl)-2-oxo-2,3-dihydrobenzo[d]oxazole-6-sulfonamide hydrochloride (5-9). HRMS [M+H]: calculated: 491.0995, observed; 491.0978. $^1$H NMR (400 MHz, $CD_3$ OD): δ 7.80 (d, J=5.5 Hz, 1H); 7.60 (d, J=7.5 Hz, 1H); 7.57-7.47 (m, 3H); 7.12 (d, J=4.6 Hz, 1H); 7.07 (d, J=9.2 Hz, 1H); 6.76 (d, J=4.6 Hz, 1H); 5.80 (d, J=48.5 Hz, 1H); 5.19-5.05 (m, 2H); 4.69 (d, J=16.1 Hz, 1H); 4.43 (dd, J=16.1, 5.5 Hz, 1H); 4.02-3.91 (m, 1H); 3.71-3.57 (m, 1H).

The compounds illustrated in Table 2 were prepared from benzoxazolinone 3-3 and the appropriate chiral alcohol in accordance with the synthetic sequence depicted in Scheme 5:

TABLE 2

| Ex No. | Structure | Name | Exact Mass [M + H]+ |
| --- | --- | --- | --- |
| 5-10 | 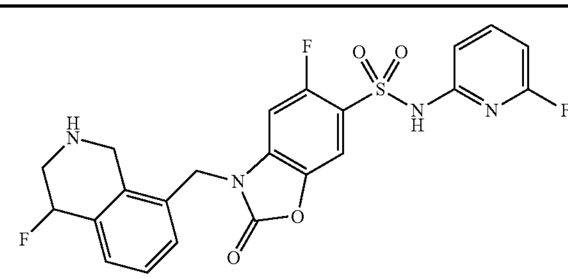 | (R or S)-5-fluoro-N-(6-fluoropyridin-2-yl)-3-[(4-fluoro-1,2,3,4-tetrahydroisoquinolin-8-yl)methyl]-2-oxo-2,3-dihydro-1,3-benzoxazole-6-sulfonamide (enantiomer 1) | Calc'd 491.0995, found 491.0988 |

TABLE 2-continued

| Ex No. | Structure | Name | Exact Mass [M + H]+ |
|---|---|---|---|
| 5-11 | 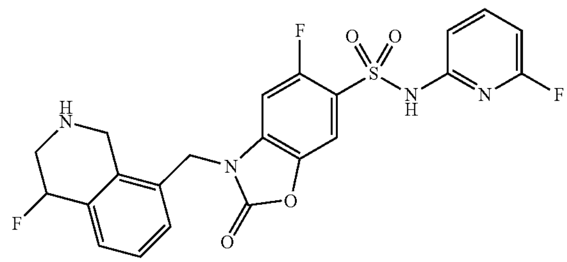 [SMILES: O=c1oc2cc(S(=O)(=O)Nc3cccc(F)n3)c(F)cc2n1Cc1cccc2c1CNCC2F] | (S or R)-5-fluoro-N-(6-fluoropyridin-2-yl)-3-[(4-fluoro-1,2,3,4-tetrahydroisoquinolin-8-yl)methyl]-2-oxo-2,3-dihydro-1,3-benzoxazole-6-sulfonamide (enantiomer 2) | Calc'd 491.0995, found 491.0988 |

Example 5

Preparation of 3-((4,4-Difluoro-1,2,3,4-tetrahydroisoquinolin-8-yl)methyl)-5-fluoro-N-(6-fluoropyridin-2-yl)-2-oxo-2,3-dihydrobenzo[d]oxazole-6-sulfonamide hydrochloride (6-5)

Scheme 6 illustrates first preparation of a suitably functionalized "alcohol precursor" (Compound 6-3) and its use in preparation of compounds of the invention by reaction schemes illustrated in Examples 1 and 2, above, with Compound 3-3 prepared in accordance with Example 2, above.

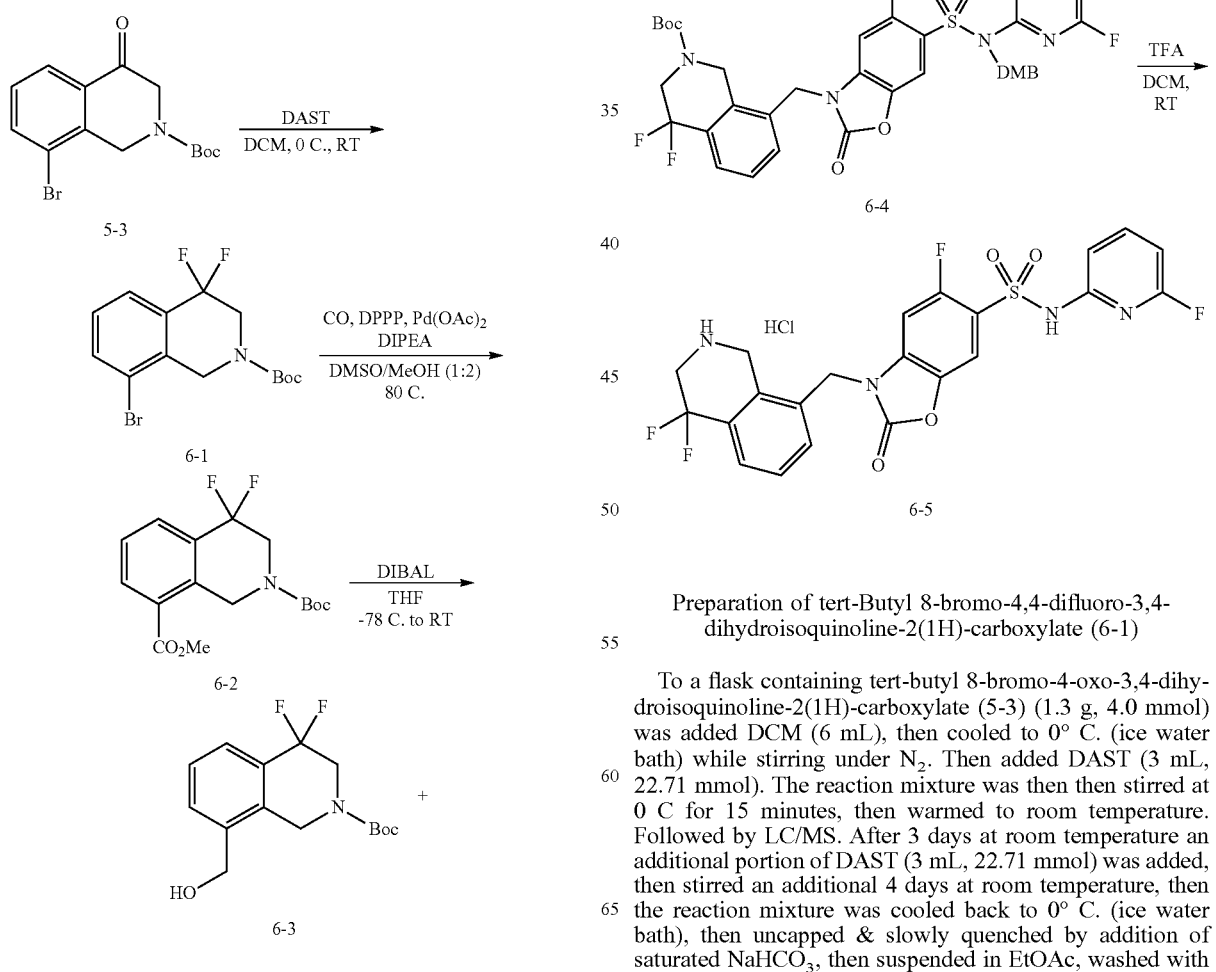

Preparation of tert-Butyl 8-bromo-4,4-difluoro-3,4-dihydroisoquinoline-2(1H)-carboxylate (6-1)

To a flask containing tert-butyl 8-bromo-4-oxo-3,4-dihydroisoquinoline-2(1H)-carboxylate (5-3) (1.3 g, 4.0 mmol) was added DCM (6 mL), then cooled to 0° C. (ice water bath) while stirring under $N_2$. Then added DAST (3 mL, 22.71 mmol). The reaction mixture was then then stirred at 0 C for 15 minutes, then warmed to room temperature. Followed by LC/MS. After 3 days at room temperature an additional portion of DAST (3 mL, 22.71 mmol) was added, then stirred an additional 4 days at room temperature, then the reaction mixture was cooled back to 0° C. (ice water bath), then uncapped & slowly quenched by addition of saturated $NaHCO_3$, then suspended in EtOAc, washed with saturated NaHCO₃, then water, then brine; organics dried over Na₂SO₄, filtered & concentrated. Purification by silica gel chromatography (0-15% EtOAc/Hex; 120 g ISCO) desired fractions concentrated to yield tert-butyl 8-bromo-4,4-difluoro-3,4-dihydroisoquinoline-2(1H)-carboxylate (6-1).

Preparation of 3-((4,4-Difluoro-1,2,3,4-tetrahydroisoquinolin-8-yl)methyl)-5-fluoro-N-(6-fluoropyridin-2-yl)-2-oxo-2,3-dihydrobenzo[d]oxazole-6-sulfonamide hydrochloride (6-5)

To a flask containing tert-butyl 8-((6-(N-(2,4-dimethoxybenzyl)-N-(6-fluoropyridin-2-yl)sulfamoyl)-5-fluoro-2-oxobenzo[d]oxazol-3(2H)-yl)methyl)-4,4-difluoro-3,4-dihydroisoquinoline-2(1H)-carboxylate (6-4) (55 mg, 0.072 mmol, prepared from the appropriate starting materials by a sequence analogous to that illustrated in Scheme 5) in DCM (3 mL) was added TFA (500 μl, 6.49 mmol). The reaction mixture was then stirred at room temperature open to the atmosphere. Followed by LC/MS. After 20 minutes the reaction mixture was diluted/quenched with DMSO, then MeOH, then filtered (syringe filter), the filtrate was then concentrated (to remove DCM), then diluted with MeOH/DMSO & purified (without workup) by reverse phase chromatography (5-75% MeCN/water; 0.1% TFA in AQ; 20 min gradient; Waters 30×150 mm Sunfire 5 micron C18 column); desired fractions concentrated (GENEVAC), then dissolved in MeOH/DCM & added saturated HCl in EtOAc (~4N) & concentrated to yield 3-((4,4-difluoro-1,2,3,4-tetrahydroisoquinolin-8-yl)methyl)-5-fluoro-N-(6-fluoropyridin-2-yl)-2-oxo-2,3-dihydrobenzo[d]oxazole-6-sulfonamide hydrochloride (6-5). HRMS [M+H]: calculated; 509.0901, observed; 509.0895. ¹H NMR (400 MHz, CD₃ OD): δ 7.93 (d, J=5.6 Hz, 1H); 7.81 (d, J=7.8 Hz, 1H); 7.75 (q, J=8.1 Hz, 1H); 7.66 (d, J=7.7 Hz, 1H); 7.59 (t, J=7.8 Hz, 1H); 7.14 (d, J=9.4 Hz, 1H); 6.94 (dd, J=7.9, 2.0 Hz, 1H); 6.59 (dd, J=8.0, 2.5 Hz, 1H); 5.12 (br s, 2H); 4.66 (br s, 2H); 4.00 (t, J=11.4 Hz, 2H).

Example 6

Preparation of phenyl-substituted compounds of the invention (R)-5-Fluoro-N-(6-fluoropyridin-2-yl)-3-(1-(2-iodophenyl)ethyl)-2-oxo-2,3-dihydrobenzo[d]oxazole-6-sulfonamide (Compound 7-3) and (R)-5-Fluoro-N-(6-fluoropyridin-2-yl)-2-oxo-3-(1-(2-(1,2,3,6-tetrahydropyridin-4-yl)phenyl)ethyl)-2,3-dihydrobenzo[d]oxazole-6-sulfonamide (Compound 7-5), and others Scheme 7 illustrates preparation of a compound of the invention using an "alcohol precursor" which contains a reactive substituent in addition to the alcohol moiety, thereby providing compound 7-3 which is suitable for preparing additional compounds of the invention (Compound 7-5) and analogs thereof.

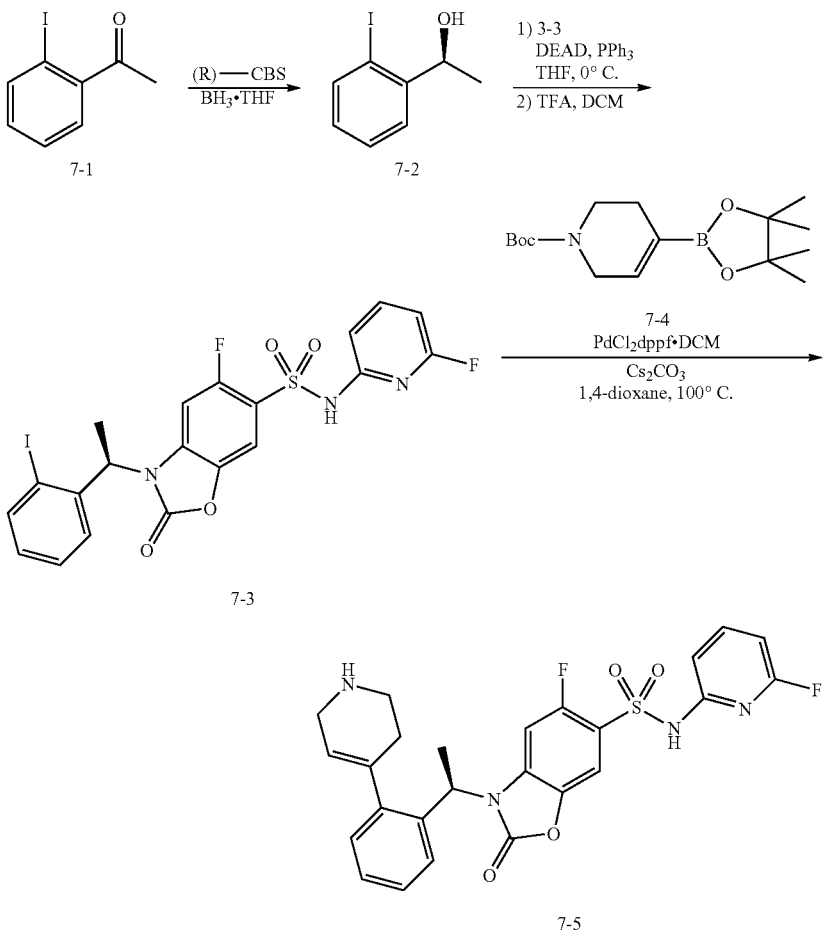

Preparation of (S)-1-(2-Iodophenyl)ethanol (7-2)

A solution of (R)—CBS (20.32 mL, 20.32 mmol) and commercial 7-1 (5 g, 20.32 mmol) in THF (102 mL) was treated with BH$_3$.THF (20.32 mL, 20.32 mmol, 1M in THF), diluted with an additional 50 mL of THF, delivered via syringe pump at 75 mL/hr. Quenched with 2N HCl (50 mL), extracted into EtOAc (150 mL), and dried over Sodium sulfate before concentrating in vacuo. Material was taken up in dichloromethane and filtered. Filtrate was purified by normal phase chromatography (0-30% EtOAc in hexane). Isolated material chirally separated (ChiralPak AD-H) to yield 7-2 as a white solid.

Preparation of (R)-5-Fluoro-N-(6-fluoropyridin-2-yl)-3-(1-(2-iodophenyl)ethyl)-2-oxo-2,3-dihydrobenzo[d]oxazole-6-sulfonamide (7-3)

A solution of 3-3 (3.5 g, 7.33 mmol) and triphenylphosphine (3.85 g, 14.66 mmol) in THF (73.3 mL) was treated with DEAD (2.321 mL, 14.66 mmol). After cooling to 0° C. in an ice bath, 7-2 (2.000 g, 8.06 mmol) was added. After stirring for 1 hour at 0° C., the solvent was removed under reduced pressure. Purified by normal phase chromatography (0-60% EtOAc in hexane). Isolated material was dissolved in 50 mL of DCM and treated with 10 mL of TFA. Stirred for 30 minutes at RT. Purified by reverse phase chromatography (30-100% MeCN in water with 0.1% TFA, C18 column) to yield 7-3 as a white solid.

Preparation of (R)-5-Fluoro-N-(6-fluoropyridin-2-yl)-2-oxo-3-(1-(2-(1,2,3,6-tetrahydropyridin-4-1)phenyl)ethyl)-2,3-dihydrobenzo[d]oxazole-6-sulfonamide (7-5)

A solution of Compound 7-3 (50 mg, 0.09 mmol), commercial tert-butyl 4-(4,4,5,5-tetramethyl-1,3,2-dioxaborolan-2-yl)-5,6-dihydropyridine-1(2H)-carboxylate (47 mg, 0.15 mmol), (2-dicyclohexyl-phosphino-2',4',6'-triisopropyl-1,1'-biphenyl)[2-(2-aminoethyl)phenyl]palladium (II) chloride (6.6 mg, 9 μmmol), and Cs$_2$CO$_3$ (0.27 mL, 1M in water, 0.27 mmol) in 1,4-Dioxane (0.8 mL) was degassed with nitrogen and heated overnight at 75° C. Purified by reverse phase chromatography (5-70% MeCN in water w/0.1% TFA, C18 column) to yield 7-5 as a white solid (TFA salt). $^1$H NMR δ (ppm)(DMSO-d$_6$): 11.75 (1H, s), 8.86 (2H, s), 7.91-7.80 (2H, m), 7.75 (1H, d, J=7.76 Hz), 7.45-7.34 (2H, m), 7.06 (1H, d, J=7.43 Hz), 6.99 (1H, d, J=9.94 Hz), 6.89 (1H, d, J=7.90 Hz), 6.75-6.71 (1H, m), 5.72-5.65 (1H, m), 5.38 (1H, s), 3.29 (2H, s), 3.17 (2H, s), 2.60-2.49 (1H, m), 2.12-2.00 (1H, m), 1.82 (3H, d, J=7.08 Hz). HRMS C25H22F2N4O4S [M+H] calc: 513.1403, obs: 513.1391.

The compounds illustrated in Table 3 were prepared from benzoxazolinone 7-3 and the appropriate boronate in accordance with the synthetic sequence depicted in Scheme 7:

TABLE 3

| Ex No. | Structure | Name | Exact Mass [M + H]+ |
|---|---|---|---|
| 7-6 | 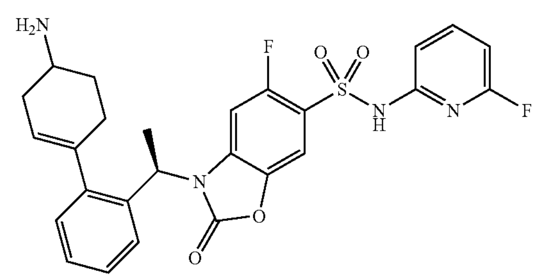 [SMILES: C[C@H](c1ccccc1C1=CCC(N)CC1)n1c(=O)oc2cc(S(=O)(=O)Nc3cccc(F)n3)c(F)cc21] | 3-{(1R)-1-[2-(4-aminocyclohex-1-en-1-yl)phenyl]ethyl}-5-fluoro-N-(6-fluoropyridin-2-yl)-2-oxo-2,3-dihydro-1,3-benzoxazole-6-sulfonamide | Calc'd 527.1559, found 527.1552 |
| 7-7 | 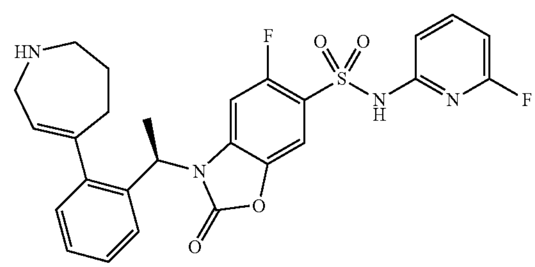 [SMILES: C[C@H](c1ccccc1C1=CCNCCC1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[2-(2,5,6,7-tetrahydro-1H-azepin-4-yl)phenyl]ethyl}-2,3-dihydro-1,3-benzoxazole-6-sulfonamide | Calc'd 527.1559, found 527.1551 |
| 7-8 | 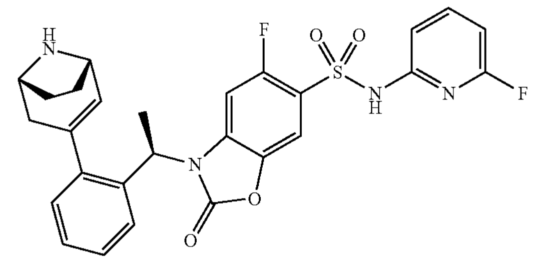 [SMILES: C[C@H](c1ccccc1C1=C[C@@H]2CC[C@H](C1)N2)n1c(=O)oc2cc(S(=O)(=O)Nc3cccc(F)n3)c(F)cc21] | 3-[(1R)-1-{2-[(1S,5R)-8-azabicyclo[3.2.1]oct-2-en-3-yl]phenyl}ethyl]-5-fluoro-N-(6-fluoropyridin-2-yl)-2-oxo-2,3-dihydro-1,3-benzoxazole-6-sulfonamide | Calc'd 539.1559, found 539.1551 |

TABLE 3-continued

| Ex No. | Structure | Name | Exact Mass [M + H]+ |
|---|---|---|---|
| 7-9 | 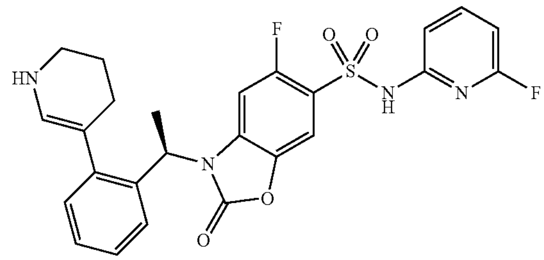 [SMILES: C[C@H](c1ccccc1C1=CNCCC1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[2-(1,2,5,6-tetrahydropyridin-3-yl)phenyl]ethyl}-2,3-dihydro-1,3-benzoxazole-6-sulfonamide | Calc'd 513.1403, found 513.1393 |
| 7-10 | 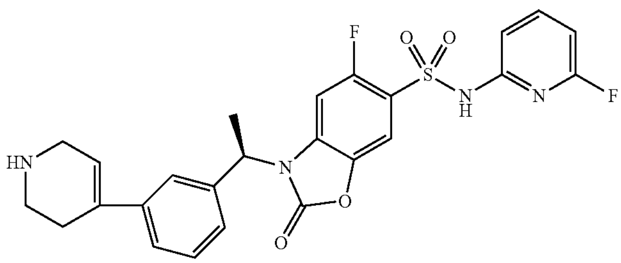 [SMILES: C[C@H](c1cccc(C2=CCNCC2)c1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[3-(1,2,3,6-tetrahydropyridin-4-yl)phenyl]ethyl}-2,3-dihydro-1,3-benzoxazole-6-sulfonamide | Calc'd 512.1, found 513.2 |
| 7-11 | 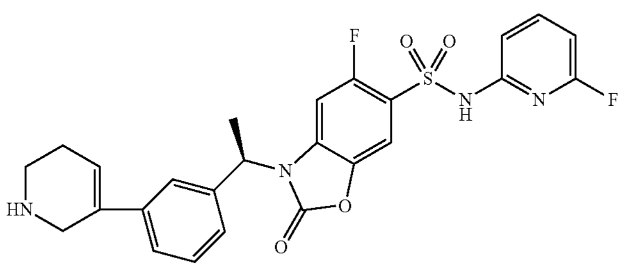 [SMILES: C[C@H](c1cccc(C2=CCCNC2)c1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[3-(1,2,5,6-tetrahydropyridin-3-yl)phenyl]ethyl}-2,3-dihydro-1,3-benzoxazole-6-sulfonamide | Calc'd 512.1, found 513.1 |
| 7-12 | 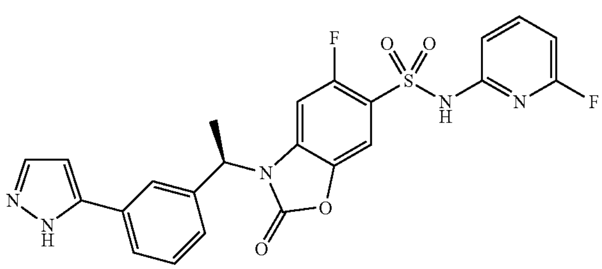 [SMILES: C[C@H](c1cccc(-c2ccn[nH]2)c1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[3-(1H-pyrazol-5-yl)phenyl]ethyl}-2,3-dihydro-1,3-benzoxazole-6-sulfonamide | Calc'd 497.1 found 498.2 |

Example 7

Preparation of (R)-3-(1-(2-(3-Aminoprop-1-yn-1-yl)phenyl)ethyl)-5-fluoro-N-(6-fluoropyridin-2-yl)-2-oxo-2,3-dihydrobenzo[d]oxazole-6-sulfonamide (Compound 8-1)

Scheme 8 illustrates the preparation of additional compounds of the invention by derivatizing Compound 7-3, prepared in Example 6, above, using reactions which are analogous to those described in Example 6.

Scheme 8

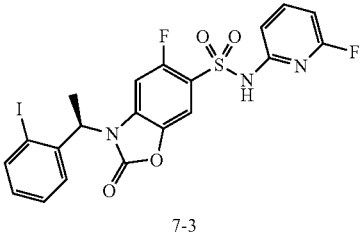

1) Boc-propargylamine
   CuI, tetrakis, TEA
   MeCN, 60° C.
2) TFA, DCM, RT

-continued

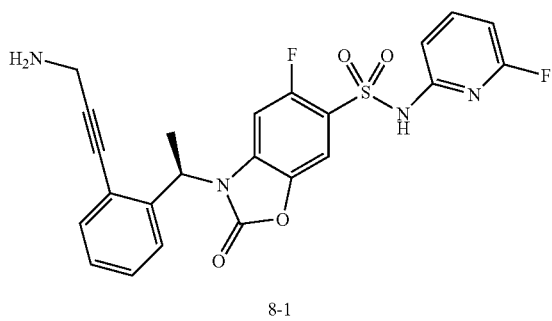

8-1

Accordingly, Compound 7-3 prepared in accordance with Example 6 (100 mg, 0.179 mmol), commercial tert-butyl prop-2-yn-1-ylcarbamate (33.4 mg, 0.215 mmol), Copper (I) iodide (10.25 mg, 0.054 mmol), Tetrakis (20.73 mg, 0.018 mmol) and triethylamine (1.25 mL, 8.97 mmol) were dissolved in degassed MeCN (1.8 mL) and the solution was heated to 60° C. for 1 hour. After cooling to RT, the solvent and TEA were removed in vacuo. Residue was taken up in 2 mL of dichloromethane and treated with 0.3 mL of TFA. Stirred for 1 hour at RT. Purified by reverse phase chromatography (5-70% MeCN in water w/0.1% TFA, C18 column) to yield 8-1 as the TFA salt. $^1$H NMR δ (ppm)(DMSO-$d_6$): 11.76 (1H, s), 8.29 (3H, s), 7.92-7.87 (1H, m), 7.89-7.81 (1H, m), 7.75 (1H, d, J=7.92 Hz), 7.54 (1H, t, J=7.63 Hz), 7.47 (1H, d, J=7.51 Hz), 7.45-7.39 (1H, m), 7.06 (1H, d, J=9.85 Hz), 6.93-6.88 (1H, m), 6.76-6.72 (1H, m), 5.80-5.73 (1H, m), 3.99-3.84 (2H, m), 1.86 (3H, d, J=7.17 Hz). HRMS C23H18F2N4O4S [M+H] calc: 485.1090, obs: 485.1074.

The following compounds were prepared from 7-3 by the synthetic sequence illustrated in Scheme 8:

TABLE 4

| Exp No. | Structure | Name | Exact Mass [M + H]+ |
|---|---|---|---|
| 8-2 | 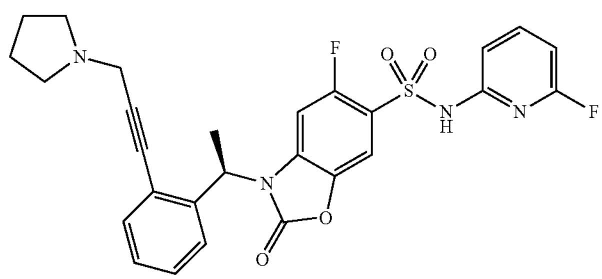 [SMILES: C[C@H](c1ccccc1C#CCN1CCCC1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[2-(3-pyrrolidin-1-ylprop-1-yn-1-yl)phenyl]ethyl}-2,3-dihydro-1,3-benzoxazole-6-sulfonamide | Calc'd 539.1559, found 539.1539 |
| 8-3 | 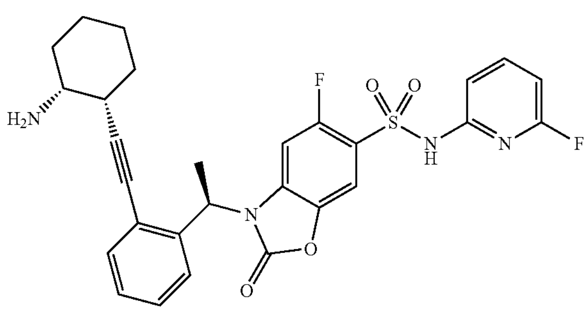 [SMILES: C[C@H](c1ccccc1C#C[C@H]1CCCC[C@H]1N)n1c(=O)oc2cc(S(=O)(=O)Nc3cccc(F)n3)c(F)cc21] | 3-[(1R)-1-(2-{[(1R,2R)-2-aminocyclohexyl]ethynyl}phenyl)ethyl]-5-fluoro-N-(6-fluoropyridin-2-yl)-2-oxo-2,3-dihydro-1,3-benzoxazole-6-sulfonamide | Calc'd 553.1716, found 553.1698 |
| 8-4 | 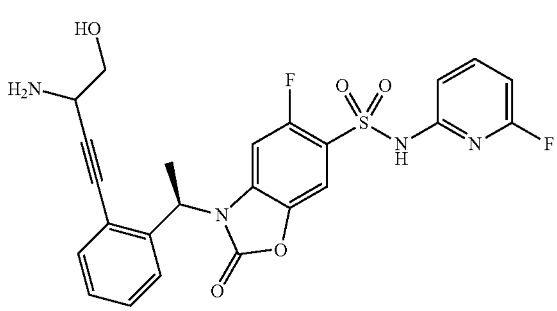 [SMILES: C[C@H](c1ccccc1C#CC(N)CO)n1c(=O)oc2cc(S(=O)(=O)Nc3cccc(F)n3)c(F)cc21] | 3-{(1R)-1-[2-(3-amino-4-hydroxybut-1-yn-1-yl)phenyl]ethyl}-5-fluoro-N-(6-fluoropyridin-2-yl)-2-oxo-2,3-dihydro-1,3-benzoxazole-6-sulfonamide | Calc'd 515.1195, found 515.1180 |

TABLE 4-continued

| Exp No. | Structure | Name | Exact Mass [M + H]+ |
|---|---|---|---|
| 8-5 | 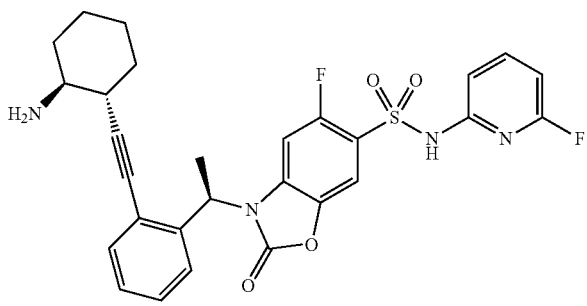 [SMILES: C[C@H](c1ccccc1C#C[C@H]1CCCC[C@@H]1N)n1c(=O)oc2cc(S(=O)(=O)Nc3cccc(F)n3)c(F)cc21] | 3-[(1R)-1-(2-{[(1R,2S and 1S, 2R)-2-aminocyclohexyl]ethynyl}phenyl)ethyl]-5-fluoro-N-(6-fluoropyridin-2-yl)-2-oxo-2,3-dihydro-1,3-benzoxazole-6-sulfonamide | Calc'd 553.172, found 553.1710 |
| 8-6 | 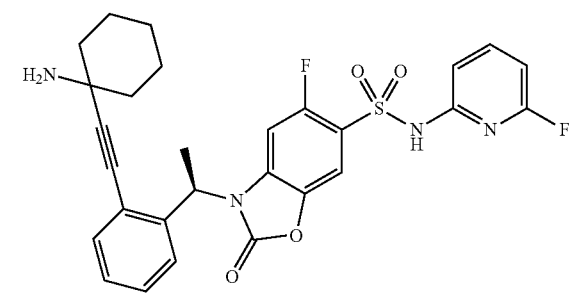 [SMILES: C[C@H](c1ccccc1C#CC1(N)CCCCC1)n1c(=O)oc2cc(S(=O)(=O)Nc3cccc(F)n3)c(F)cc21] | 3-[(1R)-1-{2-[(1-aminocyclohexyl)ethynyl]phenyl}ethyl]-5-fluoro-N-(6-fluoropyridin-2-yl)-2-oxo-2,3-dihydro-1,3-benzoxazole-6-sulfonamide | Calc'd 553.1716, found 553.1714 |
| 8-7 | 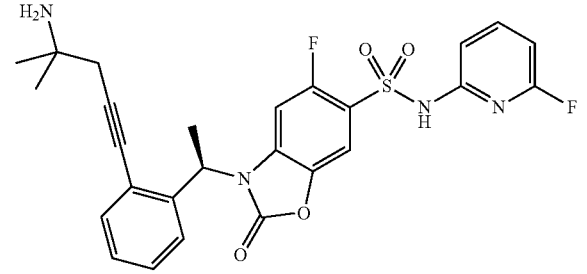 [SMILES: C[C@H](c1ccccc1C#CCC(C)(C)N)n1c(=O)oc2cc(S(=O)(=O)Nc3cccc(F)n3)c(F)cc21] | 3-{(1R)-1-[2-(4-amino-4-methylpent-1-yn-1-yl)phenyl]ethyl}-5-fluoro-N-(6-fluoropyridin-2-yl)-2-oxo-2,3-dihydro-1,3-benzoxazole-6-sulfonamide | Calc'd 527.1559, found 527.1552 |
| 8-8 | 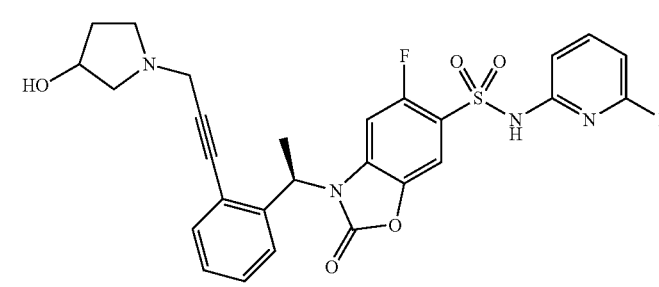 | 5-fluoro-N-(6-fluoropyridin-2-yl)-3-[(1R)-1-{2-[3-(3-hydroxypyrrolidin-1-yl)prop-1-yn-1-yl]phenyl}ethyl]-2-oxo-2,3-dihydro-1,3-benzoxazole-6-sulfonamide | Calc'd 555.1508, found 555.1489 |
| 8-9 | 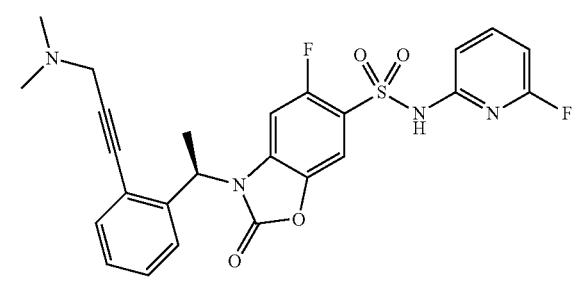 [SMILES: C[C@H](c1ccccc1C#CCN(C)C)n1c(=O)oc2cc(S(=O)(=O)Nc3cccc(F)n3)c(F)cc21] | 3-[(1R)-1-{2-[3-(dimethylamino)prop-1-yn-1-yl]phenyl}ethyl]-5-fluoro-N-(6-fluoropyridin-2-yl)-2-oxo-2,3-dihydro-1,3-benzoxazole-6-sulfonamide | Calc'd 513.5, found 513.2 |

TABLE 4-continued

| Exp No. | Structure | Name | Exact Mass [M + H]+ |
|---|---|---|---|
| 8-10 | 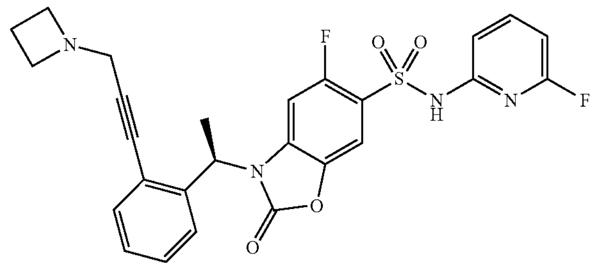 [SMILES: C[C@H](c1ccccc1C#CCN1CCC1)n1c(=O)oc2cc(S(=O)(=O)Nc3cccc(F)n3)c(F)cc21] | 3-{(1R)-1-[2-(3-azetidin-1-ylprop-1-yn-1-yl)phenyl]ethyl}-5-fluoro-N-(6-fluoropyridin-2-yl)-2-oxo-2,3-dihydro-1,3-benzoxazole-6-sulfonamide | Calc'd 525.1403, found 525.1383 |

Example 8

Preparation of (R)-3-(1-(2-(aminomethyl)phenyl)ethyl)-5-fluoro-N-(6-fluoropyridin-2-yl)-2-oxo-2,3-dihydrobenzo[d]oxazole-6-sulfonamide (Compound 9-1)

Scheme 9 illustrates preparation of additional compounds of the invention by derivative reaction of Compound 7-3 prepared in accordance with the procedure of Example 6.

Scheme 9

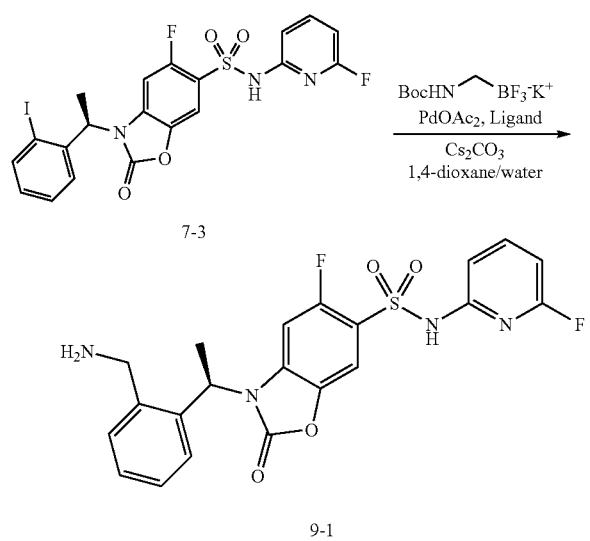

Accordingly, compound 7-3 (prepared in accordance with Example 6, 52 mg, 0.093 mmol), commercial Potassium N-Boc-amino-methyltrifluoroborate (22.12 mg, 0.093 mmol), $Cs_2CO_3$ (91 mg, 0.280 mmol), palladium (II) acetate (2.095 mg, 9.33 µmol), and butyldi-1-adamantylphosphine (6.69 mg, 0.019 mmol) were dissolved in degassed water (156 µl) and 1,4-dioxane (778 µl) was heated to 85° C. overnight. Organic layer was decanted and concentrated in vacuo. Residue was taken up in 2 mL of DCM and was treated at 0° C. with 0.2 mL of TFA, then allowed to warm to RT over 1 hour. Purified by reverse phase chromatography (5-75% MeCN in water w/0.1% TFA, C18 column) to yield 9-1 as the TFA salt. $^1H$ NMR δ (ppm)(DMSO-$d_6$): 11.76 (1H, s), 8.20 (3H, s), 7.93 (1H, d, J=7.23 Hz), 7.89-7.80 (2H, m), 7.48-7.45 (3H, m), 7.29 (1H, d, J=10.03 Hz), 6.93-6.88 (1H, m), 6.74-6.71 (1H, m), 5.82 (1H, q, J=7.00 Hz), 4.20-4.13 (1H, m), 4.09-4.02 (1H, m), 1.83 (3H, d, J=7.00 Hz). HRMS C21H18F2N4O4S [M+H] calc: 461.1090, obs: 461.1075

The following compounds were prepared from 7-3 by the synthetic sequence illustrated in Scheme 9:

TABLE 5

| Exp. No. | Structure | Name | Exact Mass [M + H]+ |
|---|---|---|---|
| 9-2 | 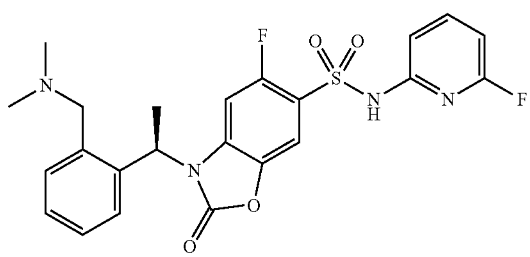 [SMILES: C[C@H](c1ccccc1CN(C)C)n1c(=O)oc2cc(S(=O)(=O)Nc3cccc(F)n3)c(F)cc21] | 3-[(1R)-1-{2-[(dimethylamino)methyl]phenyl}ethyl]-5-fluoro-N-(6-fluoropyridin-2-yl)-2-oxo-2,3-dihydro-1,3-benzoxazole-6-sulfonamide | Calc'd 489.1403, found 489.1395 |

TABLE 5-continued

| Exp. No. | Structure | Name | Exact Mass [M + H]+ |
|---|---|---|---|
| 9-3 | 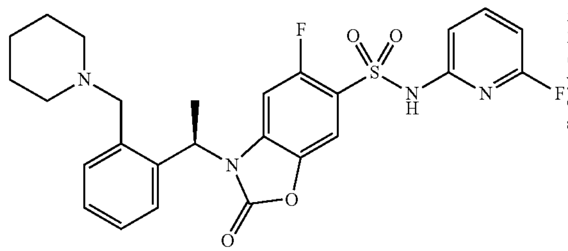 [SMILES: C[C@H](c1ccccc1CN1CCCCC1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[2-(piperidin-1-ylmethyl)phenyl]ethyl}-2,3-dihydro-1,3-benzoxazole-6-sulfonamide | Calc'd 529.1716, found 529.1693 |

Example 9

Preparation of (R)-3-(1-(2-(azetidin-3-yl)phenyl)ethyl)-5-fluoro-N-(6-fluoropyridin-2-yl)-2-oxo-2,3-dihydrobenzo[d]oxazole-6-sulfonamide (Compound 10-3)

Scheme 10 illustrates first preparation of a suitably azetidine-functionalized "alcohol precursor" (Compound 10-2) and its use in preparation of Compound 10-3 by reaction with "core" precursor Compound 3-3 prepared in Example 2, above.

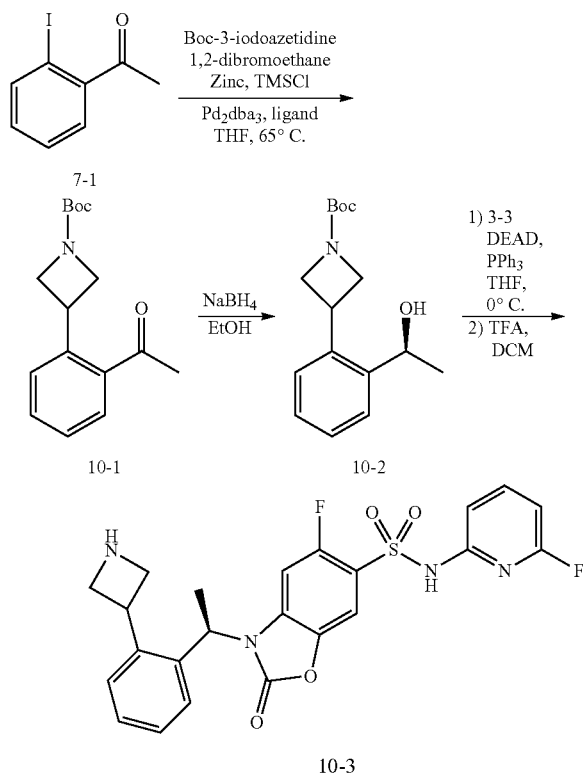

Scheme 10

Preparation of tert-Butyl 3-(2-acetylphenyl)azetidine-1-carboxylate (10-1)

To a flask containing a suspension of Zinc metal (1.594 g, 24.39 mmol) in 10 mL of THF was added 1,2-dibromoethane (0.210 mL, 2.439 mmol) then heated to 65° C. in a preheated oil bath. After heating for 10 minutes, the reaction was allowed to cool to room temperature. TMS—Cl (0.312 mL, 2.439 mmol) was then added and the resulting mixture was stirred at room temperature for 30 minutes. tert-Butyl 3-iodoazetidine-1-carboxylate (6.56 g, 23.17 mmol) in 6.5 mL of THF was then added and the reaction was stirred at room temperature for 45 minutes. A solution of tri(2-furyl)phosphine (1.132 g, 4.88 mmol) and Pd$_2$dba$_3$ (1.117 g, 1.219 mmol) in 5 mL of THF was added followed by a solution of 7-1 (3 g, 12.19 mmol) in 3 mL of THF. Reaction was heated to 65° C. for 18 hours. The reaction was then cooled to room temperature, quenched with saturated sodium bicarbonate solution and extracted into EtOAc (3×150 mL). Combined organic layers were washed with brine, dried over sodium sulfate, then filtered and concentrated. The resulting residue was purified by silica gel chromatography (0-40% EtOAc in hexane) to yield 10-1.

Preparation of (S)-tert-Butyl 3-(2-(1-hydroxyethyl)phenyl)azetidine-1-carboxylate (10-2)

A solution of 10-1 (1.7 g, 6.17 mmol) in Ethanol (61.7 mL) was cooled to 0° C. in an ice bath. The reaction was then treated with sodium borohydride (0.374 g, 9.88 mmol) and the reaction was slowly allowed to reach room temperature. After 45 minutes, the reaction was quenched with 25 mL of concentrated aqueous NH$_4$Cl solution at 0° C. Extracted with EtOAc (3×75 mL). Combined organic layers were washed with brine, dried over sodium sulfate, filtered and concentrated in vacuo. The resulting residue was purified by silica gel chromatography (0-60% EtOAc in hexane). Separated enantiomers using chiral column chromatography (chiral IC column). Concentration of chirally separated fractions yielded 10-2.

Preparation of (R)-3-(1-(2-(Azetidin-3-yl)phenyl)ethyl)-5-fluoro-N-(6-fluoropyridin-2-yl)-2-oxo-2,3-dihydrobenzo[d]oxazole-6-sulfonamide (10-3)

A solution of 3-3 (100 mg, 0.209 mmol) and DEAD (66.3 µl, 0.419 mmol) in THF (2 mL) was treated with triphenylphosphine (110 mg, 0.419 mmol, PS-supported resin) followed by 10-2 (58 mg, 0.21 mmol). After stirring for overnight at RT, the reaction was filtered and concentrated in vacuo. Residue was dissolved in 1 mL of DCM and treated with 0.25 mL of TFA. After stirring at RT for 30 minutes, the solvent and TFA were removed in vacuo. Purified by reverse phase chromatography (5-95% MeCN in water w/0.1% TFA, C18 column) to yield 10-3 as the TFA salt. $^1$H NMR δ (ppm)(DMSO-d$_6$): 11.76 (1H, s), 8.88 (1H, s), 8.53 (1H, s), 7.89 (1H, d, J=5.73 Hz), 7.87-7.80 (1H, m), 7.75 (1H, d, J=7.76 Hz), 7.63 (1H, d, J=7.74 Hz), 7.53-7.47 (1H, m), 7.47-7.41 (1H, m), 7.04 (1H, d, J=10.03 Hz), 6.92-6.87 (1H, m), 6.75-6.71 (1H, m), 5.59-5.52 (1H, m), 4.33-4.26 (2H, m), 4.15-4.09 (1H, m), 4.00-3.87 (2H, m), 1.79 (3H, d, J=6.98 Hz). HRMS C23H20F2N4O4S [M+H] calc: 487.1246, obs: 487.1245.

Example 10

Preparation of (R)-5-fluoro-N-(6-fluoropyridin-2-yl)-3-(1-(2-(1-methylsulfonyl)azetidin-3-yl)phenyl)ethyl)-2-oxo-2,3-dihydrobenzo[d]oxazole-6-sulfonamide (Compound 11-1)

Scheme 11 illustrates first preparation of further derivatives from compound 10-3 prepared in Example 9, above.

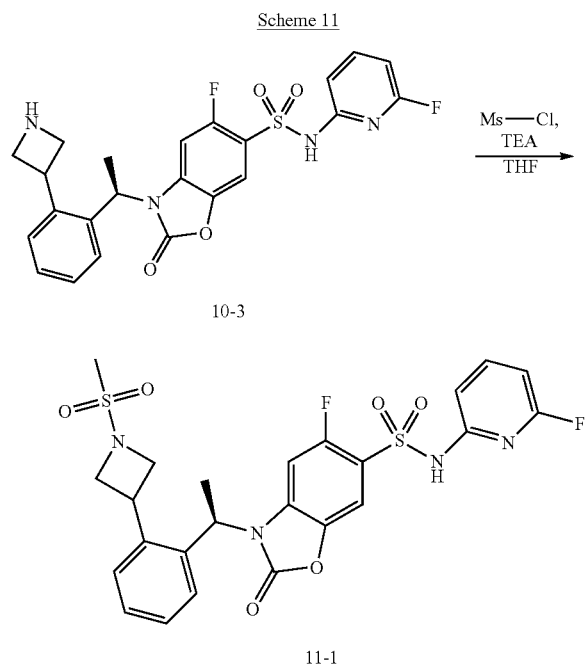

A solution of 10-3 (28 mg, 0.023 mmol) and TEA (9.75 μl, 0.07 mmol) in THF (1 mL) was treated with methanesulfonyl chloride (0.023 mmol, 1.8 μl). Reaction was stirred at RT for 30 minutes. Purified by reverse phase chromatography (10-85% MeCN in water with 0.1% TFA, C18 column) to yield 11-1 as a solid. $^1$H NMR δ (ppm)(DMSO-d$_6$): 11.74 (1H, s), 7.89 (1H, d, J=5.71 Hz), 7.88-7.80 (1H, m), 7.71 (1H, d, J=7.78 Hz), 7.63 (1H, d, J=7.74 Hz), 7.46 (1H, t, J=7.52 Hz), 7.40 (1H, t, J=7.56 Hz), 7.02 (1H, d, J=10.00 Hz), 6.91-6.86 (1H, m), 6.74-6.70 (1H, m), 5.65-5.58 (1H, m), 4.28-4.21 (1H, m), 4.09-4.02 (1H, m), 4.02-3.95 (1H, m), 3.81 (1H, t, J=8.04 Hz), 3.72 (1H, t, J=7.43 Hz), 3.03 (3H, s), 1.80 (3H, d, J=7.00 Hz). HRMS C24H22F2N4O6S2 [M+H] calc: 565.1022, obs: 565.1011.

Example 11

Preparation of (R)-5-Fluoro-N-(6-fluoropyridin-2-yl)-3-(1-(2-(3-hydroxyazetidin-3-yl)phenyl)ethyl)-2-oxo-2,3-dihydrobenzo[d]oxazole-6-sulfonamide (12-4) and (R)-5-Fluoro-3-(1-(2-(3-fluoroazetidin-3-yl)phenyl)ethyl)-N-(6-fluoropyridin-2-yl)-2-oxo-2,3-dihydrobenzo[d]oxazole-6-sulfonamide (Compound 12-6)

Scheme 12 illustrates preparation of phenyl-azetidine-substituted compounds of the invention (Compounds 12-4 and 12-6) from the corresponding iodophenyl-substituted intermediate (Compound 12-1).

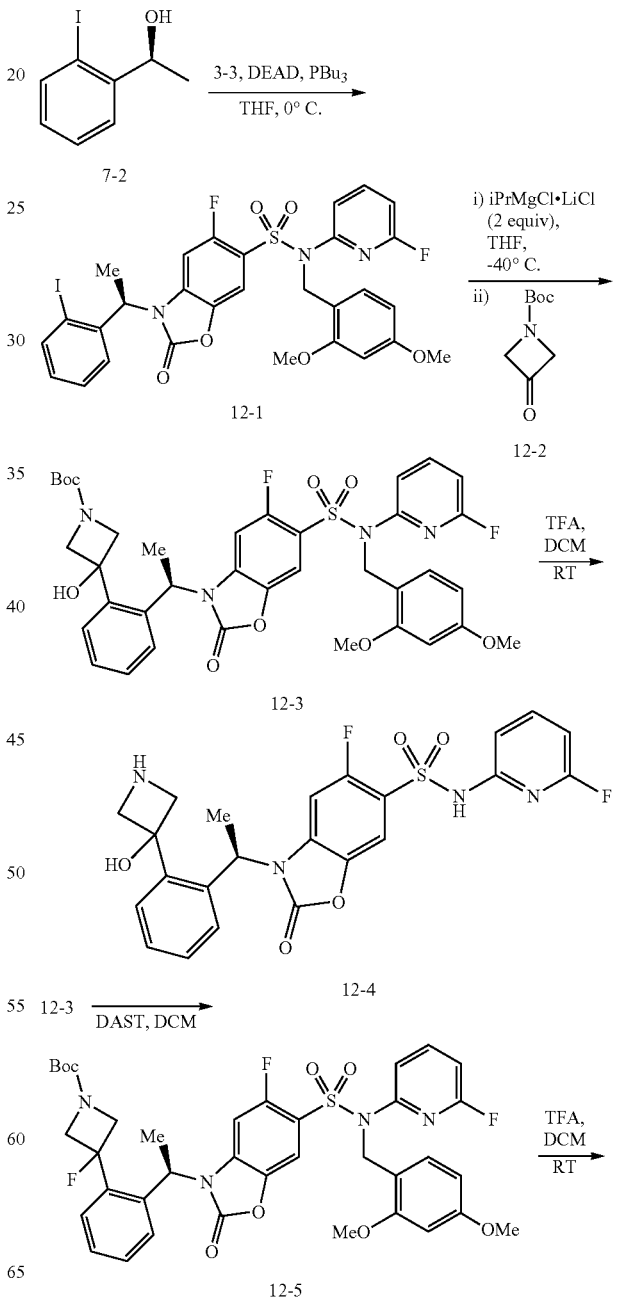

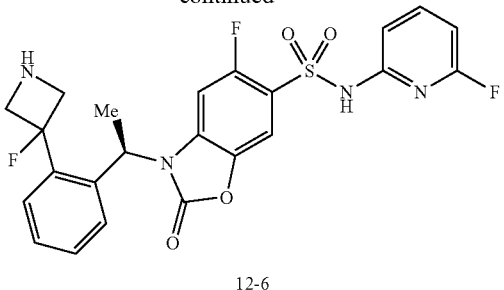

12-6

Preparation of (R)—N-(2,4-Dimethoxybenzyl)-5-fluoro-N-(6-fluoropyridin-2-yl)-3-(1-(2-iodophenyl)ethyl)-2-oxo-2,3-dihydrobenzo[d]oxazole-6-sulfonamide (12-1)

N-(2,4-dimethoxybenzyl)-5-fluoro-N-(6-fluoropyridin-2-yl)-2-oxo-2,3-dihydrobenzo[d]oxazole-6-sulfonamide (3-3, 2 g, 4.19 mmol) was added to THF (20.95 mL) to give a pale yellow solution. Added tri-N-butylphosphine (2.07 mL, 8.38 mmol) and DEAD (1.326 mL, 8.38 mmol) and cooled to 0° C. Was a clear orange solution. Added (S)-1-(2-iodophenyl)ethanol (7-2, 1.04 g, 4.19 mmol). After 6.5 h at 0° C., concentrated in vacuo and purified by normal-phase HPLC (80 g ISCO column, 0-50% EtOAc:Hex) to give 12-1 as a white solid.

Preparation of (R)-tert-Butyl 3-(2-(1-(6-(N-(2,4-dimethoxybenzyl)-N-(6-fluoropyridin-2-yl)sulfamoyl)-5-fluoro-2-oxobenzo[d]oxazol-3(2H)-yl)ethyl)phenyl)-3-hydroxyazetidine-1-carboxylate (12-3)

In an oven-dried RB flask, added (R)—N-(2,4-dimethoxybenzyl)-5-fluoro-N-(6-fluoropyridin-2-yl)-3-(1-(2-iodophenyl)ethyl)-2-oxo-2,3-dihydrobenzo[d]oxazole-6-sulfonamide (12-1, 400 mg, 0.565 mmol) to THF (2120 μl) and cooled to −40° C. Was a suspension. Added isopropylmagnesium chloride-lithium chloride complex (1305 μl, 1.696 mmol) dropwise, stirred at −40° C. for 20 min—became a bright orange solution. Following this duration, added tert-butyl 3-oxoazetidine-1-carboxylate (12-2, 290 mg, 1.696 mmol) in THF (707 μl) dropwise via syringe. Solution turned from orange to pale yellow in color. After 60 min at −40° C., partitioned between 10 mL saturated NH₄Cl+15 mL EtOAc, separated layers. Back-extracted aqueous with 2×10 mL EtOAc. Dried combined organics over Na₂SO₄, filtered, concentrated to give a pale yellow oil. Dissolved in 2 mL DMSO, purified by reverse-phase HPLC (C18 column, 10-90% 0.1% TFA/CH₃CN:0.1% TFA/water) to give 12-3 as a pale yellow solid Preparation of (R)-5-Fluoro-N-(6-fluoropyridin-2-yl)-3-(1-(2-(3-hydroxyazetidin-3-yl)phenyl)ethyl)-2-oxo-2,3-dihydrobenzo[d]oxazole-6-sulfonamide (12-4)

In a 1 dram vial, added (R)-tert-butyl 3-(2-(1-(6-(N-(2,4-dimethoxybenzyl)-N-(6-fluoropyridin-2-yl)sulfamoyl)-5-fluoro-2-oxobenzo[d]oxazol-3(2H)-yl)ethyl)phenyl)-3-hydroxyazetidine-1-carboxylate (12-3, 3 mg, 3.99 μmol) to DCM (26.6 μl) and TFA (13.28 μl). After 10 min, UPLC showed complete consumption SM to desired product. Concentrated in vacuo, added 2 mL MeOH, filtered through Celite and rinsed with MeOH. Concentrated filtrate in vacuo, dissolved in 2 mL DMSO and purified by reverse-phase HPLC (C18 column, 5-50% 0.1% TFA/CH₃CN:0.1% TFA/water) to give 12-4 as a white solid. ¹H NMR δ (ppm) (DMSO-d₆): 9.44 (1H, s), 8.74 (1H, s), 7.89-7.81 (2H, m), 7.77 (1H, d, J=7.75 Hz), 7.44 (2H, dt, J=25.57, 7.50 Hz), 7.33-7.28 (2H, m), 6.91 (1H, d, J=7.96 Hz), 6.75-6.71 (1H, m), 5.39 (1H, q, J=6.99 Hz), 4.63 (2H, t, J=8.22 Hz), 4.24 (1H, s), 4.02 (1H, s), 1.86 (3H, d, J=6.96 Hz). HRMS C23H21F2N4O5S [M+H] calc: 503.1195, obs: 503.1187.

Preparation of (R)-tert-Butyl 3-(2-(1-(6-(N-(2,4-dimethoxybenzyl)-N-(6-fluoropyridin-2-yl)sulfamoyl)-5-fluoro-2-oxobenzo[d]oxazol-3(2H)-yl)ethyl)phenyl)-3-fluoroazetidine-1-carboxylate (12-5)

In an oven-dried 2 dram vial under N₂, added (R)-tert-butyl 3-(2-(1-(6-(N-(2,4-dimethoxybenzyl)-N-(6-fluoropyridin-2-yl)sulfamoyl)-5-fluoro-2-oxobenzo[d]oxazol-3(2H)-yl)ethyl)phenyl)-3-hydroxyazetidine-1-carboxylate (12-3, 185.8 mg, 0.247 mmol) to DCM (1234 μl) and cooled to −78° C. Added DAST (65.2 μl, 0.494 mmol) dropwise. After 32 min at −78° C., removed from bath and allowed to slowly warm to RT. Twenty minutes after bath removal, LCMS showed consumption of SM to desired product. Cooled reaction contents to 0° C., slowly quenched with 3 mL water. Diluted with 5 mL DCM, separated layers, back-extracted aqueous with 1×5 mL DCM. Washed combined organics with 1×5 mL water, 1×5 mL brine. Dried combined organics over Na₂SO₄, filtered, concentrated to give a white solid. Carried crude product forward to subsequent step.

Preparation of (R)-5-Fluoro-3-(1-(2-(3-fluoroazetidin-3-yl)phenyl)ethyl)-N-(6-fluoropyridin-2-yl)-2-oxo-2,3-dihydrobenzo[d]oxazole-6-sulfonamide (12-6)

In a 1 dram vial, added crude (R)-tert-butyl 3-(2-(1-(6-(N-(2,4-dimethoxybenzyl)-N-(6-fluoropyridin-2-yl)sulfamoyl)-5-fluoro-2-oxobenzo[d]oxazol-3(2H)-yl)ethyl)phenyl)-3-fluoroazetidine-1-carboxylate (12-5) to DCM (1776 μl) and TFA (444 μl). After 15 min, UPLC showed complete consumption of SM to desired product. Diluted with 3 mL MeOH, filtered through Celite and purified by reverse-phase HPLC (C18 column, 5-60% 0.1% TFA/CH₃CN:0.1% TFA/water) to give 12-6 as a white solid. ¹H NMR δ (ppm) (DMSO-d₆): 11.79 (1H, s), 9.80 (1H, s), 9.16 (1H, s), 7.94-7.78 (3H, m), 7.59 (1H, d, J=7.93 Hz), 7.53-7.48 (2H, m), 7.25 (1H, d, J=10.18 Hz), 6.92 (1H, d, J=7.96 Hz), 6.76-6.72 (1H, m), 5.37 (1H, d, J=7.61 Hz), 5.00 (1H, dd, J=26.07, 12.13 Hz), 4.88 (1H, dd, J=25.92, 12.17 Hz), 4.69-4.48 (2H, m), 1.86 (3H, d, J=6.96 Hz). HRMS C23H20F3N4O4S [M+H] calc: 505.1152, obs: 505.1132.

Example 12

Preparation of (S or R)-3-((7-Amino-5,6,7,8-tetrahydronaphthalen-1-yl)methyl)-5-fluoro-N-(6-fluoropyridin-2-yl)-2-oxo-2,3-dihydrobenzo[d]oxazole-6-sulfonamide hydrochloride (Compound 13-4)

Scheme 13 illustrates first preparation of a suitably functionalized "alcohol precursor" (Compound 13-2) and its use in preparation of Compound 13-4 by reaction with Compound 3-3 prepared in Example 2, Scheme 3, in using a reaction sequence analogous to that shown in Example 2.

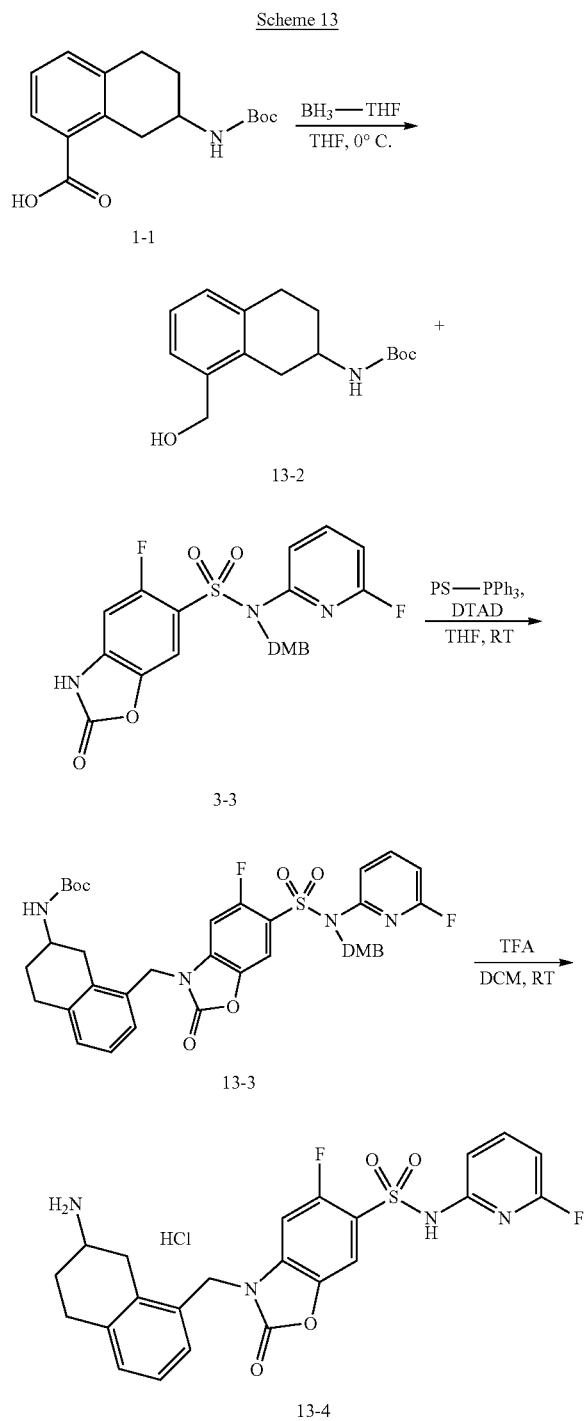

Scheme 13

Preparation of tert-butyl (8-(hydroxymethyl)-1,2,3,4-tetrahydronaphthalen-2-yl)carbamate (13-2)

To a flask was added 7-((tert-butoxycarbonyl)amino)-5,6,7,8-tetrahydronaphthalene-1-carboxylic acid (1-1) (2.02 g, 6.93 mmol), then anhydrous THF (20 mL). The reaction mixture was cooled to 0° C. (ice water bath) while stirring under an atmosphere of nitrogen. Then a 1M solution of borane THF complex (30 mL, 30.0 mmol) was added dropwise while stirring. The reaction mixture was stirred at 0° C. for 1.5 hours. Followed by LC/MS. The reaction mixture was then uncapped (always at 0° C.), then quenched by dropwise addition of saturated $NH_4Cl$ (lots of bubbling/gas evolution). The reaction mixture was warmed to room temperature, then suspended in EtOAc, separated, the organics were then washed with saturated $NaHCO_3$, then water, then brine; dried over $Na_2SO_4$, filtered & concentrated. The resulting residue was purified by silica gel chromatography (0-50% EtOAc/Hex; 80 g ISCO); desired fractions concentrated to yield racemic tert-butyl (8-(hydroxymethyl)-1,2,3,4-tetrahydronaphthalen-2-yl)carbamate (13-2). This material was then resolved by chiral chromatography to give the corresponding (R)- and (S)-enantiomers of tert-butyl (8-(hydroxymethyl)-1,2,3,4-tetrahydronaphthalen-2-yl)carbamate.

Preparation of (S or R)-3-((7-Amino-5,6,7,8-tetrahydronaphthalen-1-yl)methyl)-5-fluoro-N-(6-fluoropyridin-2-yl)-2-oxo-2,3-dihydrobenzo[d]oxazole-6-sulfonamide hydrochloride (13-4)

To a flask containing tert-butyl (8-((6-(N-(2,4-dimethoxybenzyl)-N-(6-fluoropyridin-2-yl)sulfamoyl)-5-fluoro-2-oxobenzo[d]oxazol-3(2H)-yl)methyl)-1,2,3,4-tetrahydronaphthalen-2-yl)carbamate (13-3) (77 mg, 0.105 mmol) (prepared from 3-3 and 13-2 by a sequence analogous to that illustrated in Scheme 3) in DCM (3 mL) was added TFA (500 µl, 6.49 mmol). The reaction mixture was then stirred at room temperature open to the atmosphere. Followed by LC/MS. After 20 minutes the reaction mixture was diluted/quenched with DMSO, then filtered (syringe filter), the filtrate was then concentrated (to remove DCM), then diluted with MeOH/DMSO & purified (without workup) by reverse phase chromatography (5-75% MeCN/water; 0.1% TFA in AQ; 20 min gradient; Waters 30×150 mm Sunfire 5 micron C18 column); desired fractions concentrated, then dissolved in MeOH/DCM & added a saturated solution of HCl in EtOAc (~4N) & concentrated to yield 3-((7-amino-5,6,7,8-tetrahydronaphthalen-1-yl)methyl)-5-fluoro-N-(6-fluoropyridin-2-yl)-2-oxo-2,3-dihydrobenzo[d]oxazole-6-sulfonamide hydrochloride (13-4). HRMS [M+H]: calculated; 487.1246, observed; 487.1239. $^1$H NMR (499 MHz, DMSO): δ 11.77 (s, 1H); 8.30 (br s, 3H); 7.94 (d, J=5.5 Hz, 1H); 7.86 (q, J=8.1 Hz, 1H); 7.34 (d, J=9.7 Hz, 1H); 7.11 (d, J=5.8 Hz, 2H); 6.94 (d, J=8.5 Hz, 2H); 6.74 (d, J=8.1 Hz, 1H); 4.96 (s, 2H); 3.49 (br s, 1H); 3.16-3.12 (m, 1H); 2.88 (s, 2H); 2.75-2.66 (m, 1H); 2.16-2.09 (m, 1H); 1.80-1.70 (m, 1H).

The following compounds were prepared from 2-3 or 3-3 and alcohol 13-2 (R and S-enantionmers) analogously to the synthetic sequence depicted in Scheme 13:

TABLE 6

| Ex No. | Structure | Name | Exact Mass [M + H]+ |
|---|---|---|---|
| 13-5 | 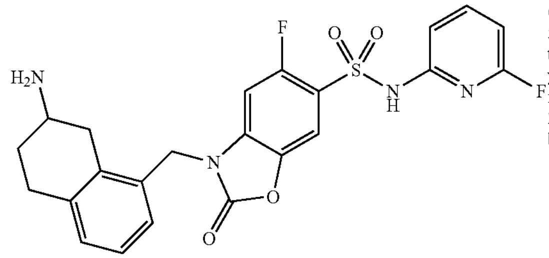 | (R or S)-3-[(7-amino-5,6,7,8-tetrahydronaphthalen-1-yl)methyl]-5-fluoro-N-(6-fluoropyridin-2-yl)-2-oxo-2,3-dihydro-1,3-benzoxazole-6-sulfonamide | Calc'd 487.1246, found 487.1244 |
| 13-6 | 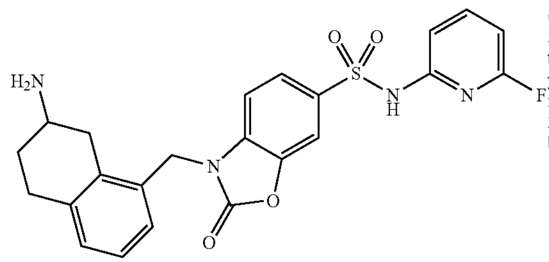 | (S or R)-3-[(7-amino-5,6,7,8-tetrahydronaphthalen-1-yl)methyl]-N-(6-fluoropyridin-2-yl)-2-oxo-2,3-dihydro-1,3-benzoxazole-6-sulfonamide | Calc'd 469.1340, found 469.1328 |

Example 13

Preparation of 3-[(1R)-1-(2-bromo-3-methylphenyl)ethyl]-5-fluoro-N-(6-fluoropyridin-2-yl)-2-oxo-2,3-dihydro-1,3-benzoxazole-6-sulfonamide (Compound 14-4)

Scheme 14 illustrates first preparation of a suitably functionalized "alcohol precursor" (Compound 14-2) and its use in preparation of Compound 14-4 by reaction with "core" precursor N-(2,4-dimethoxybenzyl)-5-fluoro-N-(6-fluoropyridin-2-yl)-2-oxo-2,3-dihydrobenzo[d]oxazole-6-sulfonamide (Compound 3-3, prepared in accordance with the reaction shown in Example 2, Scheme 3).

Scheme 14

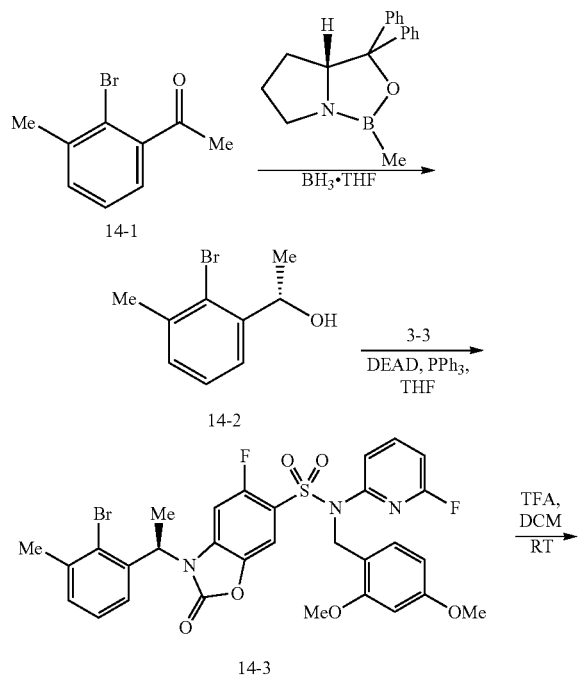

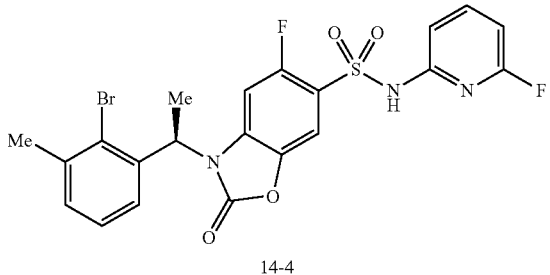

Preparation of (S)-1-(2-Bromo-3-methylphenyl)ethanol (14-2)

A solution of (R)-CBS (7.6 mL, 7.6 mmol, 1M in toluene) and 1-(2-bromo-3-methylphenyl)ethanone (1.61 g, 7.56 mmol) in THF (20 mL) was treated with the Borane (1M in THF, 7.56 mL, 7.56 mmol) in THF (30 mL) via syringe pump at 40 mL/hour. After the addition, the mixture was stirred at rt for 1 hour and HCl (1N) was added to quench the reaction. The mixture was extracted with EA and the organics were washed with water, brine and dried over $Na_2SO_4$. After filtration and concentration, the residue was purified with column (silica gel, EA/Hexane 0~30%) gave the desired product (S)-1-(2-bromo-3-methylphenyl)ethanol (14-2).

Preparation of 3-[(1R)-1-(2-Bromo-3-methylphenyl)ethyl]-N-(2,4-dimethoxybenzyl)-5-fluoro-N-(6-fluoropyridin-2-yl)-2-oxo-2,3-dihydro-1,3-benzoxazole-6-sulfonamide (14-3)

Into a flask was placed N-(2,4-dimethoxybenzyl)-5-fluoro-N-(6-fluoropyridin-2-yl)-2-oxo-2,3-dihydro-1,3-benzoxazole-6-sulfonamide (Compound 3-3, 477 mg, 1.0 mmol) dissolved in THF (10 mL) and triphenylphosphine (524 mg, 2.0 mmol) was added followed by DEAD (316 uL, 2.0 mmol). The mixture was cooled to 0° C. and (S)-1-(2-bromo-3-methylphenyl)ethanol (Compound 14-2, 236 mg, 1.1 mmol) was added. The resulting mixture was allowed to warm to room temperature slowly and stirred overnight. The solvent was removed by concentration and the residue was purified with column (silica gel, EA/Hexane 0~30%) gave the desired product 3-[(1R)-1-(2-bromo-3-methylphenyl)ethyl]-N-(2,4-dimethoxybenzyl)-5-fluoro-N-(6-fluoropyridin-2-yl)-2-oxo-2,3-dihydro-1,3-benzoxazole-6-sulfonamide (14-3).

Preparation of 3-[(1R)-1-(2-Bromo-3-methylphenyl)ethyl]-5-fluoro-N-(6-fluoropyridin-2-yl)-2-oxo-2,3-dihydro-1,3-benzoxazole-6-sulfonamide (14-4)

3-[(1R)-1-(2-bromo-3-methylphenyl)ethyl]-N-(2,4-dimethoxybenzyl)-5-fluoro-N-(6-fluoropyridin-2-yl)-2-oxo-2,3-dihydro-1,3-benzoxazole-6-sulfonamide (14-3, 665 mg) was dissolved in DCM (5 mL) and treated with TFA (1 mL) at room temperature. After stirring for 1 hour at RT, the solvent and TFA was removed in vacuo. Purified by reverse phase chromatography (30-90% MeCN in water with 0.1% TFA, C18 column) to yield 3-[(1R)-1-(2-bromo-3-methylphenyl)ethyl]-5-fluoro-N-(6-fluoropyridin-2-yl)-2-oxo-2,3-dihydro-1,3-benzoxazole-6-sulfonamide (14-4) as a white solid. $^1$H NMR δ (ppm)(DMSO-d): 7.90-7.81 (2H, m), 7.59 (1H, t, J=4.81 Hz), 7.39 (2H, d, J=4.79 Hz), 7.06 (1H, d, J=9.98 Hz), 6.91 (1H, d, J=7.96 Hz), 6.74 (1H, dd, J=7.99, 2.33 Hz), 5.67 (1H, q, J=7.02 Hz), 2.34 (3H, s), 1.81 (3H, d, J=7.06 Hz). HRMS C21H16BrF2N3O4S [M+H] calc 524.0084, obs 524.0086.

Example 14

Preparation of (R)-5-Fluoro-N-(5-fluoropyridin-2-yl)-2-oxo-3-(1-(1,2,3,4-tetrahydroisoquinolin-8-yl)ethyl)-2,3-dihydrobenzo[d]oxazole-6-sulfonamide hydrochloride (Compound 15-5)

Scheme 15 illustrates first preparation of a suitably functionalized "Het" precursor (Compound 15-2), which was prepared by a reaction analogous to that shown in Scheme 2 of Example 1, above. The "Het" precursor is then employed in the preparation of "core" precursor Compound 15-3 (analog of Compound 3-3 shown in Scheme 3) by reaction with Compound 3-2 prepared in accordance with the reaction shown in Scheme 3 of Example 2. Compound 15-3 is then reacted with "alcohol precursor" Compound 1-5 (prepared in accordance with Scheme 1 of Example 1) to provide right protected Compound-15-4.

Scheme 15

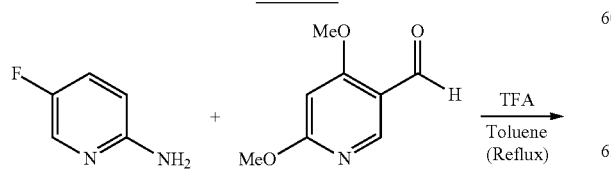

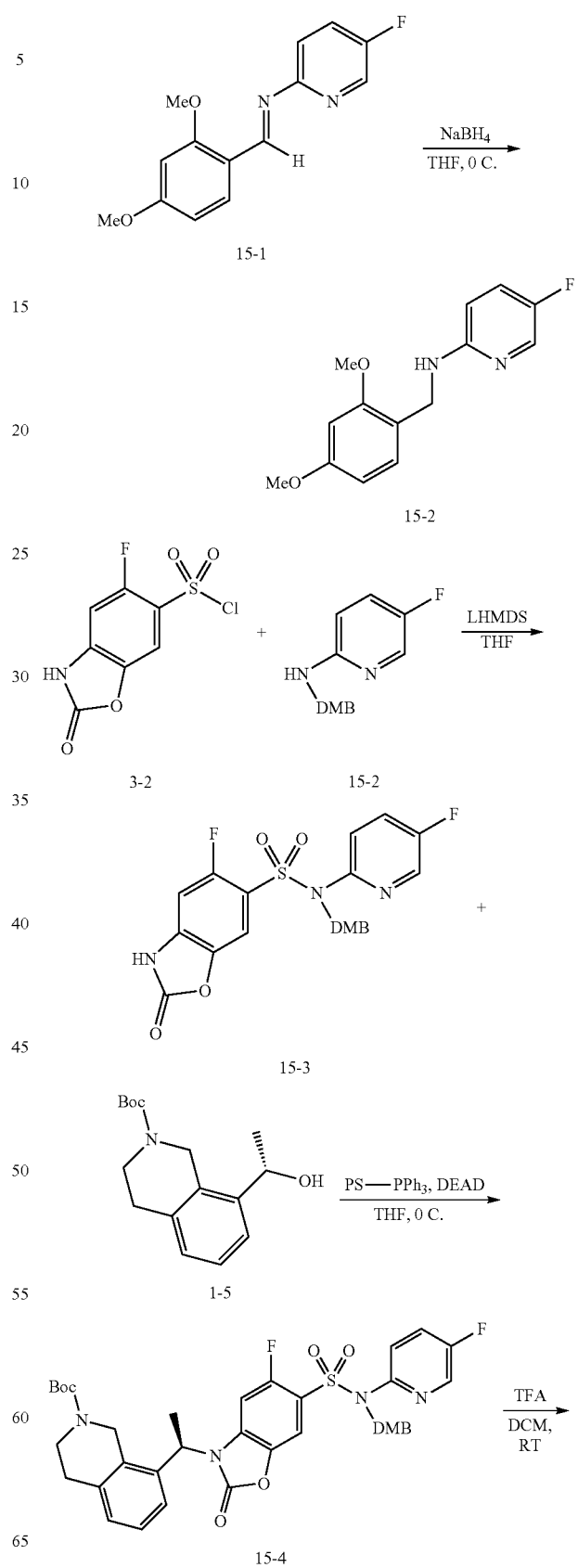

77
-continued

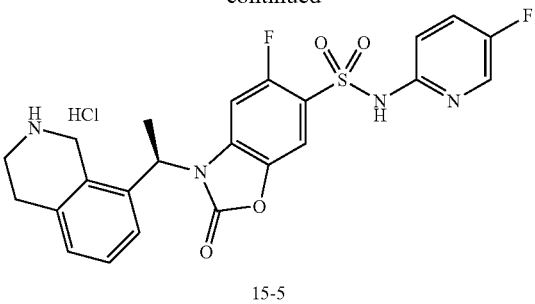

15-5

Deprotection of Compound 15-4 to provide (R)-5-Fluoro-N-(5-fluoropyridin-2-yl)-2-oxo-3-(1-(1,2,3,4-tetrahydroisoquinolin-8-yl)ethyl)-2,3-dihydrobenzo[d]oxazole-6-sulfonamide hydrochloride (15-5)

To a flask containing (R)-tert-butyl 8-(1-(6-(N-(2,4-dimethoxybenzyl)-N-(5-fluoropyridin-2-yl)sulfamoyl)-5-fluoro-2-oxobenzo[d]oxazol-3(2H)-yl)ethyl)-3,4-dihydroisoquinoline-2(1H)-carboxylate (15-4) (65 mg, 0.088 mmol) (prepared from the appropriate starting materials by a sequence analgous to that illustrated in Scheme 2) in DCM (5 mL) was added TFA (0.5 mL, 6.49 mmol). The reaction mixture was then stirred at room temperature open to the atmosphere. Followed by LC/MS. After 20 minutes the reaction mixture was diluted/quenched with DMSO, then filtered (syringe filter), the filtrate was then concentrated (to remove DCM), then diluted with MeOH/DMSO & filtered again (syringe filter)m & the filtrate was then purified (without workup) by reverse phase chromatography (5-75% MeCN/water; 0.1% TFA in AQ; 20 min gradient; Waters 30×150 mm Sunfire 5 micron C18 column); desired fractions concentrated, then dissolved in MeOH/DCM & added a saturated solution of HCl in EtOAc (~4N) & concentrated to yield (R)-5-fluoro-N-(5-fluoropyridin-2-yl)-2-oxo-3-(1-(1,2,3,4-tetrahydroisoquinolin-8-yl)ethyl)-2,3-dihydrobenzo[d]oxazole-6-sulfonamide hydrochloride (15-5). HRMS [M+H]: calculated; 487.1246, observed; 487.1241. $^1$H NMR (400 MHz, CD$_3$OD): δ 7.99 (d, J=3.0 Hz, 1H); 7.82 (d, J=5.7 Hz, 1H); 7.76 (d, J=7.8 Hz, 1H); 7.52-7.44 (m, 2H); 7.32 (d, J=7.7 Hz, 1H); 7.13 (dd, J=9.0, 3.7 Hz, 1H); 6.84 (d, J=9.8 Hz, 1H); 5.69 (q, J=7.0 Hz, 1H); 4.47 (d, J=15.7 Hz, 1H); 4.14 (d, J=15.7 Hz, 1H); 3.51-3.42 (m, 1H); 3.39-3.31 (m, 1H); 3.17-3.03 (m, 2H); 1.88 (d, J=7.0 Hz, 3H).

The compound presented in Table 7 was prepared from 15-3 and alcohol 10-2 analogously to the synthetic sequence illustrated in Scheme 10:

78
Example 15
Preparation of N-(4-Chloropyridin-2-yl)-5-fluoro-2-oxo-3-[(1R)-1-(1,2,3,4-tetrahydroisoquinolin-8-yl)ethyl]-2,3-dihydro-1,3-benzoxazole-6-sulfonamide (Compound 16-8)

Scheme 16 illustrates first preparation of a sulfide-substituted "core" precursor (Compound 16-5) which is reacted with an "alcohol precursor" (Compound 1-5) to provide sulfide intermediated Compound 16-6 which is then converted to the corresponding sulfonylchloride and the sulfonyl chloride product reacted with commercially available 2-amino-4-chloro-pyridine to yield Compound 16-8, a compound of the invention.

Scheme 16

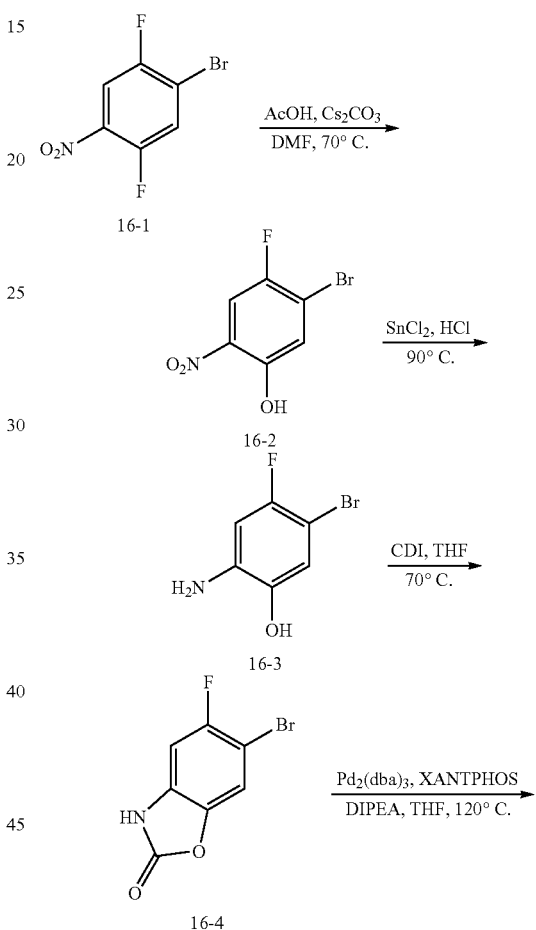

TABLE 7

| Exp. No. | Structure | Name | Exact Mass [M + H]+ |
|---|---|---|---|
| 15-6 | ![structure] | 3-[(1R)-1-(2-azetidin-3-ylphenyl)ethyl]-5-fluoro-N-(5-fluoropyridin-2-yl)-2-oxo-2,3-dihydro-1,3-benzoxazole-6-sulfonamide | Calc'd 487.1246, found 487.1239 |

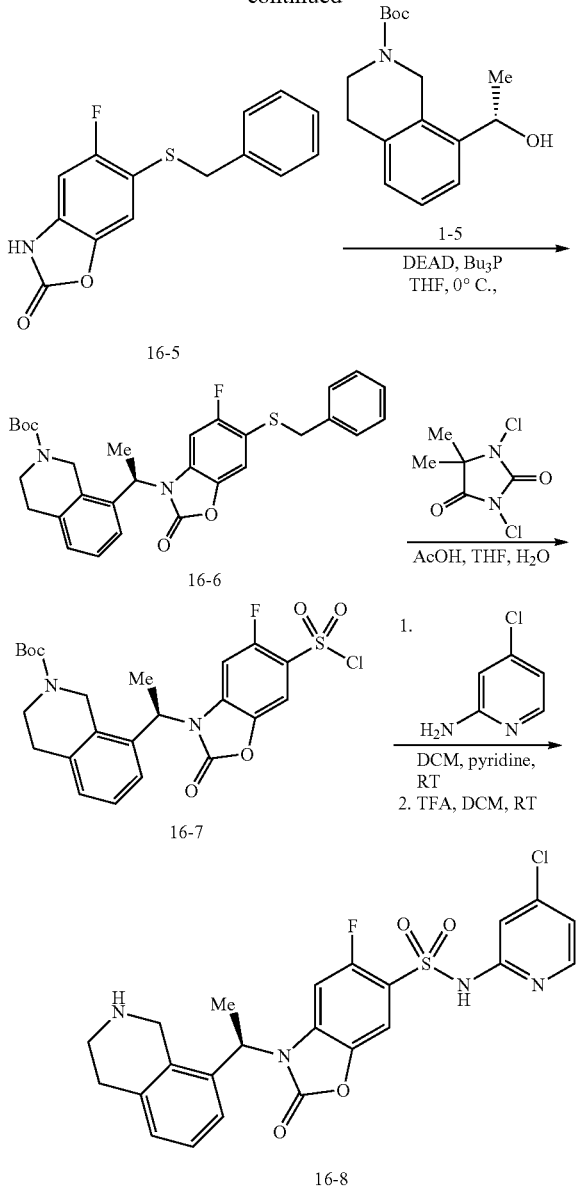

Preparation of 5-Bromo-4-fluoro-2-nitrophenol (16-2)

In a 100 mL sealed tube, added commercially-available 1-bromo-2,5-difluoro-4-nitrobenzene (16-1, 10 g, 42.0 mmol) to DMF (210 mL) followed by cesium carbonate (68.5 g, 210 mmol) and acetic acid (12.03 mL, 210 mmol). Placed in 70° C. bath. After 3.5 h, cooled to RT, diluted with 1000 mL EtOAc+500 mL water. Separated layers, used NaCl (s) to saturate aqueous layer, back-extracted with 3×150 mL EtOAc. Washed combined organics with 2×200 mL saturated $NH_4Cl$, 4×300 mL brine. Dried over $Na_2SO_4$, filtered, concentrated to give a yellow/orange solid. Carried crude material forward without further purification.

Preparation of 2-Amino-5-bromo-4-fluorophenol (16-3)

In a 200 mL sealed tube, added crude 16-2 to hydrochloric acid, 37% (53.9 mL) to give a suspension. Added tin(II) chloride dihydrate (13.19 mL, 158 mmol)—remained a suspension. Heated to 90° C.—all dissolved to give a clear, pale yellow solution. After 1.5 h at 90° C., cooled to RT, added dropwise to 400 mL saturated $Na_2CO_3$ at 0° C. with vigorous stirring. Added an additional 85 mL of 5 N NaOH to bring pH to 10-11. Warmed to RT, stirred for 10 min, and partitioned between 800 mL EtOAc and 150 mL brine. Separated layers, back-extracted aqueous with 3×200 mL EtOAc. Dried combined organics over $Na_2SO_4$, filtered and concentrated to give a white solid. $^1$H NMR/UPLC consistent with clean P1. Carried crude material forward without further purification.

Preparation of 6-Bromo-5-fluorobenzo[d]oxazol-2(3H)-one (16-4)

In a 500 mL sealed tube, added crude 16-3 to THF (293 mL). Added CDI (15.21 g, 94 mmol) in one portion and placed in 70° C. oil bath. After 18 h, concentrated to give a tan solid. Dissolved in ~200 mL EtOAc, washed with 1×150 mL water, 2×150 mL saturated $NH_4Cl$. Dried organics over $Na_2SO_4$, filtered and concentrated to give a tan solid. Carried crude material forward without further purification.

Preparation of 6-(Benzylthio)-5-fluorobenzo[d]oxazol-2(3H)-one (16-5)

Crude 16-4, XANTPHOS (1.357 g, 2.345 mmol), and Pd2(dba)3 (2.147 g, 2.345 mmol) were added to an oven-dried sealed tube followed by anhydrous dioxane (78 mL), DIPEA (8.19 mL, 46.9 mmol) and benzyl mercaptan (2.91 mL, 24.62 mmol). The resulting reaction mixture was placed in a 120° C. bath. After 2 h, LCMS showed consumption of SM to desired product. Filtered reaction contents through Celite, washed with dioxane and concentrated to give a dark orange oil. Triturated with DCM/$Et_2O$ to give an orange solid. Suspended in $Et_2O$, filtered through Buchner funnel and washed with $Et_2O$ to give 16-5 as a tan solid.

Preparation of (R)-tert-Butyl 8-(1-(6-benzylthio)-5-fluoro-2-oxobenzo[d]oxazol-3(2H)-yl)ethyl)-3,4-dihydroisoquinoline-2(1H)-carboxylate (16-6)

Added 6-(benzylthio)-5-fluorobenzo[d]oxazol-2(3H)-one (16-5, 1.5 g, 5.45 mmol) to THF (27.2 mL). Added tri-N-butylphosphine (2.69 mL, 10.90 mmol) and DEAD (1.725 mL, 10.90 mmol) and cooled to 0° C. Was a clear orange solution. Added 1-5 (1.511 g, 5.45 mmol). Solution remained clear, orange. After 2 h at 0° C., concentrated to give an orange oil. Purified by normal-phase HPLC (80 g ISCO column, 0-15% EtOAc:Hexanes) to give 16-6 as a thick, yellow oil

Preparation of (R)-tert-Butyl 8-(1-(6-(chlorosulfonyl)-5-fluoro-2-oxobenzo[d]oxazol-3(2H)-yl)ethyl)-3,4-dihydroisoquinoline-2(1H)-carboxylate (16-7)

Added (R)-tert-butyl 8-(1-(6-(benzylthio)-5-fluoro-2-oxobenzo[d]oxazol-3(2H)-yl)ethyl)-3,4-dihydroisoquinoline-2(1H)-carboxylate (16-6. 1.0 g, 1.870 mmol) to THF (17.46 mL). Added acetic acid (2.494 mL) and water (4.99 mL) and cooled to 0° C. Added 1,3 dichloro-5,5 hydantoin (1.106 g, 5.61 mmol). Reaction became homogenous immediately after addition. LCMS showed complete consumption of SM to desired product plus minor byproducts. Added reaction contents to a mixture of 60 mL saturated NaHCO₃+ 40 mL EtOAc. Separated layers, back-extracted aqueous with 2×15 mL EtOAc. Dried combined organics over Na₂SO₄, filtered and concentrated to give a white solid. Suspended in 10 mL DCM, filtered through Buchner funnel and washed with DCM. Purified by normal-phase HPLC (80 g ISCO column, 0-30% EtOAc:Hex) to give 16-7 as a white solid. Either used immediately or purged with N₂ and stored in −20° C. freezer.

Preparation of N-(4-Chloropyridin-2-yl)-5-fluoro-2-oxo-3-[(1R)-1-(1,2,3,4-tetrahydroisoquinolin-8-yl)ethyl]-2,3-dihydro-1,3-benzoxazole-6-sulfonamide (16-8)

Into a solution of R)-tert-Butyl 8-(1-(6-(chlorosulfonyl)-5-fluoro-2-oxobenzo[d]oxazol-3(2H)-yl)ethyl)-3,4-dihydroisoquinoline-2(1H)-carboxylate (16-7, 25 mg, 0.061 mmol) in DCM (600 ul) was added 2-amino-4-chloropyridine (9 mg, 0.070 mmol) followed by pyridine (14.76 ul, 0.183 mmol). The reaction was stirred for 12 h at RT and concentrated in vacuo. The crude material was subsequently dissolved in 2 mL DCM and 2 mL TFA and allowed to mature for 30 min. Following this duration, the mixture was concentrated in vacuo and purified by reverse-phase HPLC (2 cm×5 cm C18 column, acetonitrile-water gradient, 0.05% TFA added) to yield N-(4-chloropyridin-2-yl)-5-fluoro-2-oxo-3-[(1R)-1-(1,2,3,4-tetrahydroisoquinolin-8-yl)ethyl]-2,3-dihydro-1,3-benzoxazole-6-sulfonamide TFA salt (16-8) as a white solid. ¹H NMR (499 MHz, DMSO): δ 8.95 (br s, 1H); 8.00 (s, 1H); 7.85 (s, 1H); 7.72 (d, J=7.8 Hz, 1H); 7.40 (t, J=7.7 Hz, 1H); 7.26 (d, J=7.8 Hz, 1H); 7.17 (d, J=9.8 Hz, 1H); 7.01 (s, 1H); 5.61 (d, J=7.4 Hz, 1H); 4.39 (d, J=15.6 Hz, 1H); 4.10 (d, J=15.5 Hz, 1H); 3.33-3.36 (m, 2H); 3.00 (br s, 3H); 1.80 (d, J=6.9 Hz, 3H). LRMS C23H20ClFN4O4S [M+H] calc 503.1, obs 503.0.

Example 16

Preparation of Preparation of 3-(7-amino-1,2,3,4-tetrahydronaphthalen-1-yl)-5-fluoro-N-(6-fluoropyridin-2-yl)-2-oxo-2,3-dihydro-1,3-benzoxazole-6-sulfonamide (Compound 4-4)

Scheme 17 illustrates preparation of compound 17-4 using an alcohol precursor, Compound 1-5 prepared in Example 1, and intermediate 17-3 in a reaction sequence analogous to that shown in Example 3.

Scheme 17

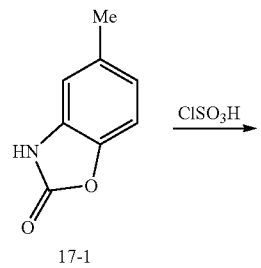

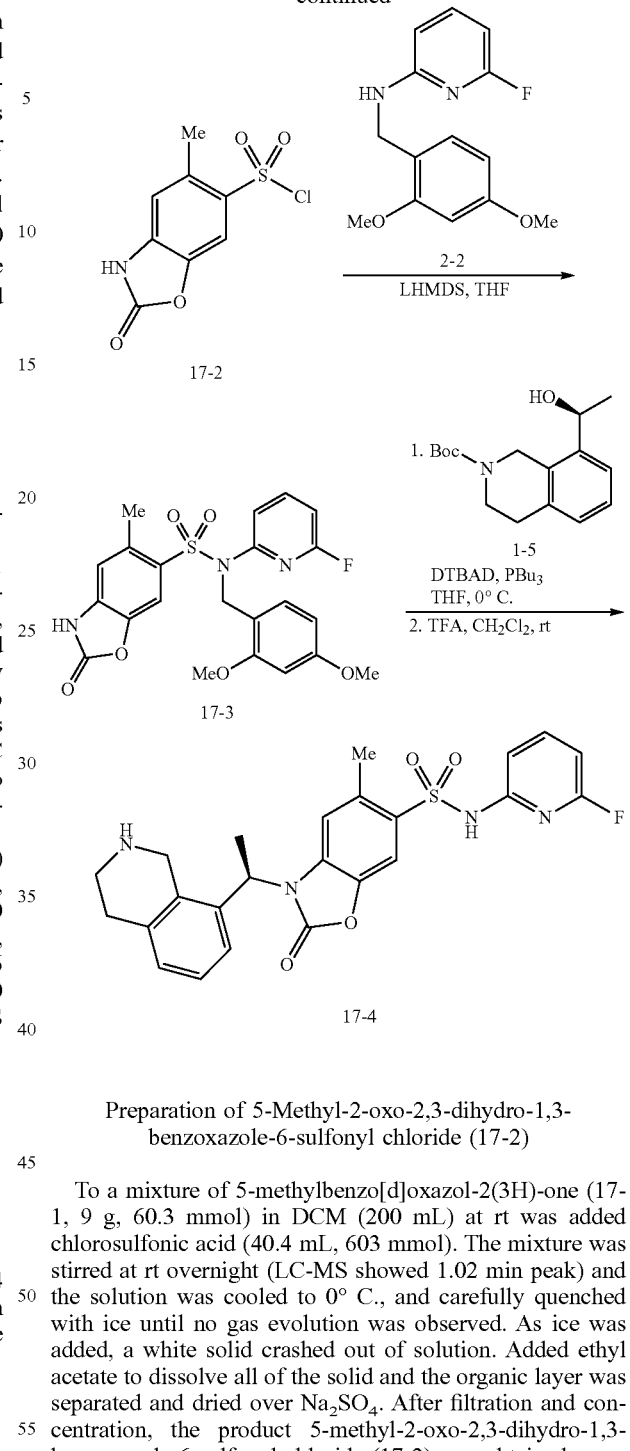

Preparation of 5-Methyl-2-oxo-2,3-dihydro-1,3-benzoxazole-6-sulfonyl chloride (17-2)

To a mixture of 5-methylbenzo[d]oxazol-2(3H)-one (17-1, 9 g, 60.3 mmol) in DCM (200 mL) at rt was added chlorosulfonic acid (40.4 mL, 603 mmol). The mixture was stirred at rt overnight (LC-MS showed 1.02 min peak) and the solution was cooled to 0° C., and carefully quenched with ice until no gas evolution was observed. As ice was added, a white solid crashed out of solution. Added ethyl acetate to dissolve all of the solid and the organic layer was separated and dried over Na₂SO₄. After filtration and concentration, the product 5-methyl-2-oxo-2,3-dihydro-1,3-benzoxazole-6-sulfonyl chloride (17-2) was obtained.

Preparation of N-(2,4-Dimethoxybenzyl)-N-(6-fluoropyridin-2-yl)-5-methyl-2-oxo-2,3-dihydro-1,3-benzoxazole-6-sulfonamide (17-3)

N-(2,4-dimethoxybenzyl)-6-fluoropyridin-2-amine (2-2, 2.51 g, 9.57 mmol) was dissolved in dry THF (20 mL) and the solution was cooled to −78° C. LHMDS (15.31 mL, 1M in hexane) was added and the resulting mixture was stirred at −78° C. for 30 min before the 5-methyl-2-oxo-2,3-dihydro-1,3-benzoxazole-6-sulfonyl chloride (17-2, 1.58 g, 6.38 mmol) in THF (5 mL) was added. The reaction was allowed to warm to room temperature slowly and stirred overnight. The reaction was quenched with water and extracted with ethyl acetate. The organics were washed with NaHCO$_3$ (aq.), water, brine and dried over Na$_2$SO$_4$. After filtration and concentration, the crude was purified with column (silica gel, ethyl acetate/hexane 0~40%) gave the product N-(2,4-dimethoxybenzyl)-N-(6-fluoropyridin-2-yl)-5-methyl-2-oxo-2,3-dihydro-1,3-benzoxazole-6-sulfonamide (17-3).

Preparation of (R)—N-(6-Fluoropyridin-2-yl)-5-methyl-2-oxo-3-(1-(1,2,3,4-tetrahydroisoquinolin-8-yl)ethyl)-2,3-dihydrobenzo[d]oxazole-6-sulfonamide (17-4)

A solution of 17-3 (100 mg, 0.211 mmol) and (E)-di-tert-butyl diazene-1,2-dicarboxylate (97 mg, 0.422 mmol) in THF (2 mL) at 0° C. was treated with tributylphosphine (58.5 µl, 0.422 mmol). After stirring for 10 min, the reaction mixture was treated with (S)-tert-butyl 8-(1-hydroxyethyl)-3,4-dihydroisoquinoline-2(1H)-carboxylate (1-5, 117 mg, 0.422 mmol) in 2 mL of THF. After stirring at 0° C. for 2 h, the reaction was filtered and concentrated in vacuo. Residue was dissolved in 1 mL of DCM and treated with 0.25 mL of TFA. After stirring at RT for 30 minutes, the solvent and TFA were removed in vacuo. Purified by reverse phase chromatography (10-95% MeCN in water w/0.1% TFA, C18 column) to yield 17-4 as the TFA salt. $^1$H NMR δ (ppm) (CH$_3$OH-d$_4$): 7.99 (1H, s), 7.81-7.65 (2H, m), 7.46 (1H, t, J=7.77 Hz), 7.30 (1H, d, J=7.73 Hz), 6.90-6.82 (2H, m), 6.54 (1H, dd, J=8.01, 2.49 Hz), 5.68 (1H, q, J=6.99 Hz), 4.48 (1H, d, J=15.74 Hz), 4.12 (1H, d, J=15.74 Hz), 3.20-3.02 (2H, m), 2.56 (3H, s), 1.89 (3H, d, J=7.00 Hz). HRMS [M+H] C$_{24}$H$_{23}$FN$_4$O$_4$S calc'd 483.1497. found 483.1482.

The following compounds were prepared from 17-3 and alcohol 13-2 (R and S-enantionmers) analogously to the synthetic sequence depicted in Scheme 13:

TABLE 8

| Ex-No. | Structure | Name | Exact Mass [M + H]+ |
| --- | --- | --- | --- |
| 17-5 | 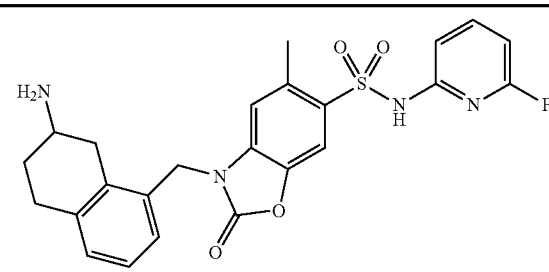 | (R or S)-3-[(7-amino-5,6,7,8-tetrahydronaphthalen-1-yl)methyl]-N-(6-fluoropyridin-2-yl)-5-methyl-2-oxo-2,3-dihydro-1,3-benzoxazole-6-sulfonamide | Calc'd 483.1497, found 483.1497 |
| 17-6 | 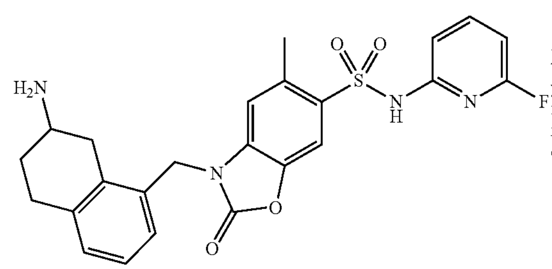 [SMILES: Cc1cc2c(cc1S(=O)(=O)Nc1cccc(F)n1)oc(=O)n2Cc1cccc2c1CC(N)CC2] | (S or R)-3-[(7-amino-5,6,7,8-tetrahydronaphthalen-1-yl)methyl]-N-(6-fluoropyridin-2-yl)-5-methyl-2-oxo-2,3-dihydro-1,3-benzoxazole-6-sulfonamide | Calc'd 483.1497, found 483.1497 |

The following compound was prepared from 17-3 analogously to the synthetic sequence depicted in Scheme 9:

TABLE 9

| Exp No. | Structure | Name | Exact Mass [M + H]+ |
| --- | --- | --- | --- |
| 17-7 | 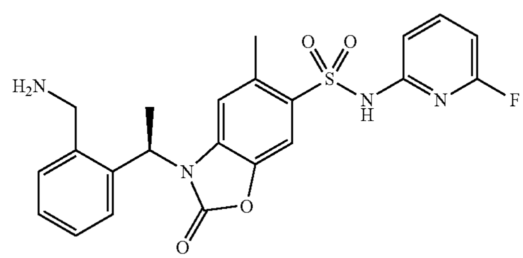 [SMILES: Cc1cc2c(cc1S(=O)(=O)Nc1cccc(F)n1)oc(=O)n2[C@H](C)c1ccccc1CN] | 3-{(1R)-1-[2-(aminomethyl)phenyl]ethyl}-N-(6-fluoropyridin-2-yl)-5-methyl-2-oxo-2,3-dihydro-1,3-benzoxazole-6-sulfonamide | Calc'd 457.1340, found 457.1321 |

The following compound was prepared from 17-3 analogously to the synthetic sequence depicted in Scheme 7:

TABLE 10

| Exp. No. | Structure | Name | Exact Mass [M + H]+ |
|---|---|---|---|
| 17-8 | 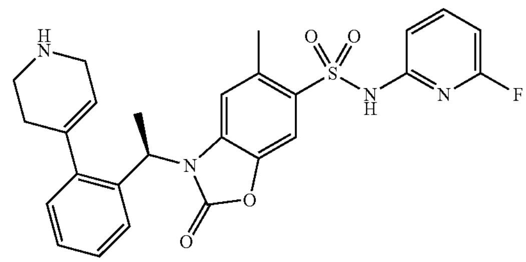 [SMILES: Cc1cc2c(cc1S(=O)(=O)Nc1cccc(F)n1)oc(=O)n2[C@H](C)c1ccccc1C1=CCNCC1] | N-(6-fluoropyridin-2-yl)-5-methyl-2-oxo-3-{(1R)-1-[2-(1,2,3,6-tetrahydropyridin-4-yl)phenyl]ethyl}-2,3-dihydro-1,3-benzoxazole-6-sulfonamide | Calc'd 509.1653, found 509.1652 |

Example 17

Preparation of (R)—N-(6-fluoropyridin-2-yl)-5-methyl-2-oxo-3-(1-(2-(piperidin-4-yl)phenyl)ethyl)-2,3-dihydrobenzo[d]oxazole-6-sulfonamide (Compound 18-3)

Scheme 18 illustrates first preparation of a suitably functionalized "alcohol precursor" (Compound 4-2) and its use in preparation of Compound 4-4 by a reaction sequence analogous to that shown in Examples 1 and 2.

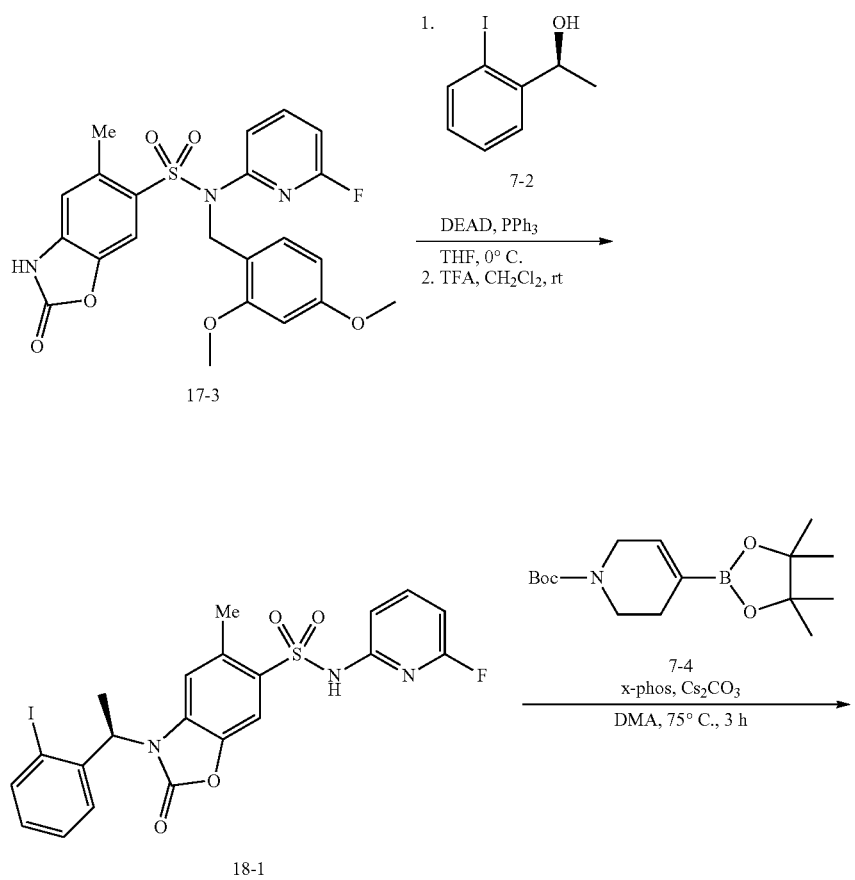

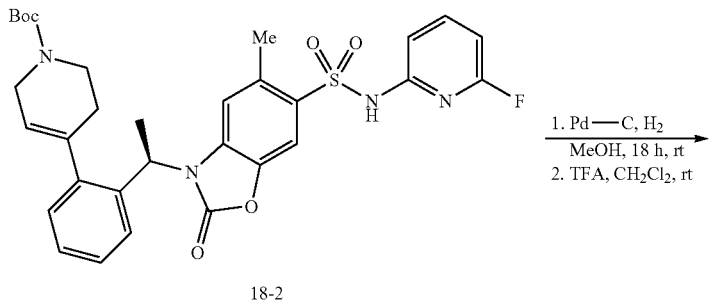

18-2

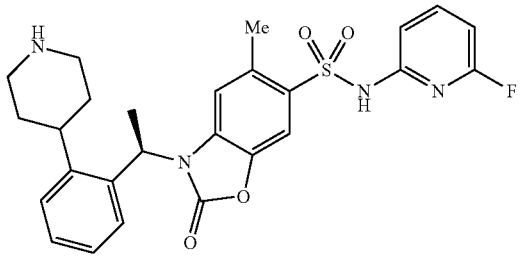

18-3

Preparation of (R)—N-(6-Fluoropyridin-2-yl)-3-(1-(2-iodophenyl)ethyl)-5-methyl-2-oxo-2,3-dihydrobenzo[d]oxazole-6-sulfonamide (18-1)

A solution of N-(2,4-dimethoxybenzyl)-N-(6-fluoropyridin-2-yl)-5-methyl-2-oxo-2,3-dihydrobenzo[d]oxazole-6-sulfonamide (16-3, 0.8 g, 1.690 mmol) and TRIPHENYLPHOSPHINE (0.886 g, 3.38 mmol) in THF (16.90 mL) was treated with DEAD (0.535 mL, 3.38 mmol). After cooling to 0° C. in an ice bath, (S)-1-(2-iodophenyl)ethanol (7-2, 0.461 g, 1.859 mmol) was added as a solid. After stirring for 2.5 hours at 0° C., the solvent was removed under reduced pressure. Crude residue was purified by silica gel column chromatography (0-40% EtOAc in hexane). Isolated material was taken up in 10 mL of DCM and treated with 2.5 mL of TFA at RT. After stirring for 30 minutes at RT, the solvent and TFA were removed in vacuo. Residue was taken up in DMSO, filtered and purified on the Gilson reverse phase prep HPLC (20-90% MeCN in water w/0.1% TFA)(C18 column) to yield 18-1.

Preparation of (R)-tert-Butyl 4-(2-(1-(6-(N-(6-fluoropyridin-2-yl)sulfamoyl)-5-methyl-2-oxobenzo[d]oxazol-3(2H)-yl)ethyl)phenyl)-5,6-dihydropyridine-1(2H)-carboxylate (18-2)

(R)—N-(6-Fluoropyridin-2-yl)-3-(1-(2-iodophenyl)ethyl)-5-methyl-2-oxo-2,3-dihydrobenzo[d]oxazole-6-sulfonamide (18-1, 100 mg, 0.181 mmol), tert-butyl 4-(4,4,5,5-tetramethyl-1,3,2-dioxaborolan-2-yl)-5,6-dihydropyridine-1(2H)-carboxylate (7-4, 95 mg, 0.307 mmol), (2-dicyclohexylphosphino-2',4',6'-triisopropyl-1,1'-biphenyl)[2-(2-aminoethyl)phenyl]palladium(ii) chloride (13.35 mg, 0.018 mmol), and cesium carbonate (177 mg, 0.542 mmol) were all added to a 5 mL microwave vial and degassed DMA (3347 µl) was added. The reaction mixture was stirred at 75° C. for 3 h and then allowed tho stir at rt overnight. Taken up in 10 mL of EtOAc, washed with water and brine. Aqueous layer was back extracted with 5 mL EtOAc three times. Combined organic layer was dried over sodium sulfate, filtered and concentrated in vacuo and purified on the Gilson reverse phase prep HPLC (5-70% MeCN in water w/0.1% TFA) (C18 column) to yield 18-2.

Preparation of (R)—N-(6-Fluoropyridin-2-yl)-5-methyl-2-oxo-3-(1-(2-(piperidin-4-yl)phenyl)ethyl)-2,3-dihydrobenzo[d]oxazole-6-sulfonamide (18-3)

A solution of 18-2 (93 mg, 0.153 mmol) and Pd-C (32.5 mg, 0.031 mmol) in 5 mL of MeOH was added to a 25 mL round bottom flask, which was connected to the vacuum line and then to a hydrogen balloon. The reaction mixture was stirred at rt overnight and then filtered and concentrated in vacuo. Residue was dissolved in 1 mL of DCM and treated with 0.25 mL of TFA. After stirring at RT for 30 minutes, the solvent and TFA were removed in vacuo. Purified by reverse phase chromatography (5-95% MeCN in water w/0.1% TFA, C18 column) to yield 18-3 as the TFA salt. $^1$H NMR δ (ppm)(CH$_3$OH-d$_4$): 7.98 (1H, s), 7.83-7.78 (1H, m), 7.69 (1H, q, J=8.08 Hz), 7.41-7.36 (2H, m), 7.33-7.29 (1H, m), 6.80 (1H, s), 6.52 (1H, dd, J=8.00, 2.50 Hz), 5.95 (1H, q, J=7.03 Hz), 3.52 (1H, d, J=12.79 Hz), 3.32-3.29 (1H, m), 3.17-3.05 (2H, m), 2.87 (1H, td, J=12.97, 3.04 Hz), 2.52 (3H, s), 1.97 (3H, s), 1.90 (3H, d, J=7.03 Hz), 1.77-1.68 (1H, m), 1.09 (1H, d, J=14.46 Hz). HRMS C$_{26}$H$_{27}$FN$_4$O$_4$S [M+H] calc: 511.1810, obs: 511.1809.

Table 11 lists compounds of the invention prepared from 3-3 and 17-3 using the procedures of Scheme 14 and Scheme 18.

TABLE 11

| Exp No. | Structure | Name | Mass [M + H]+ |
|---|---|---|---|
| 18-4 | 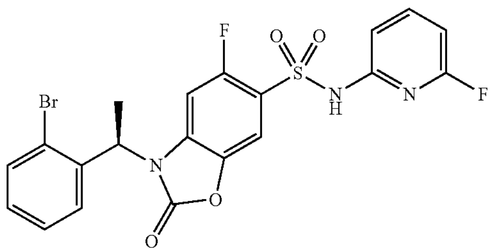 [SMILES: C[C@H](c1ccccc1Br)n1c(=O)oc2cc(S(=O)(=O)Nc3cccc(F)n3)c(F)cc21] | 3-[(1R)-1-(2-bromophenyl)ethyl]-5-fluoro-N-(6-fluoropyridin-2-yl)-2-oxo-2,3-dihydro-1,3-benzoxazole-6-sulfonamide | Calc'd 509.0 found 510.3 |
| 18-5 | 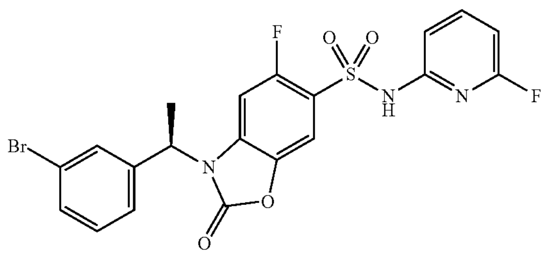 [SMILES: C[C@H](c1cccc(Br)c1)n1c(=O)oc2cc(S(=O)(=O)Nc3cccc(F)n3)c(F)cc21] | 3-[(1R)-1-(3-bromophenyl)ethyl]-5-fluoro-N-(6-fluoropyridin-2-yl)-2-oxo-2,3-dihydro-1,3-benzoxazole-6-sulfonamide | Calc'd 509.0 found 510.2 |
| 18-6 | 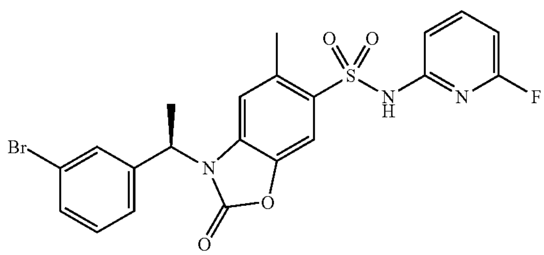 [SMILES: Cc1cc2c(cc1S(=O)(=O)Nc1cccc(F)n1)oc(=O)n2[C@H](C)c1cccc(Br)c1] | 3-[(1R)-1-(3-bromophenyl)ethyl]-N-(6-fluoropyridin-2-yl)-5-methyl-2-oxo-2,3-dihydro-1,3-benzoxazole-6-sulfonamide | Calc'd 505.0 found 506.1 |
| 18-7 | 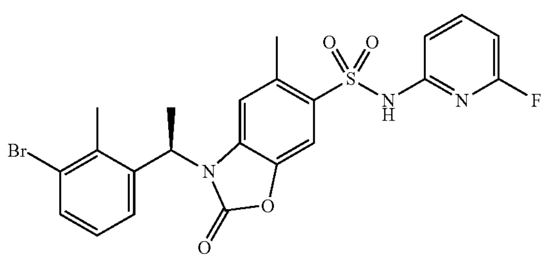 [SMILES: Cc1cc2c(cc1S(=O)(=O)Nc1cccc(F)n1)oc(=O)n2[C@H](C)c1cccc(Br)c1C] | 3-[(1R)-1-(3-bromo-2-methylphenyl)ethyl]-N-(6-fluoropyridin-2-yl)-5-methyl-2-oxo-2,3-dihydro-1,3-benzoxazole-6-sulfonamide | Calc'd 519.0 found 520.1 |
| 18-8 | 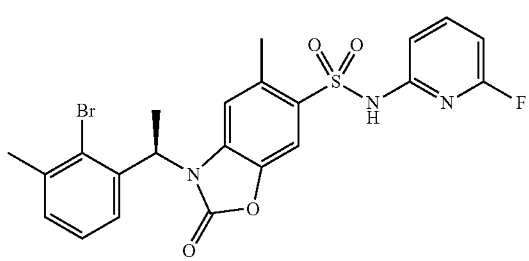 [SMILES: Cc1cc2c(cc1S(=O)(=O)Nc1cccc(F)n1)oc(=O)n2[C@H](C)c1cccc(C)c1Br] | 3-[(1R)-1-(2-bromo-3-methylphenyl)ethyl]-N-(6-fluoropyridin-2-yl)-5-methyl-2-oxo-2,3-dihydro-1,3-benzoxazole-6-sulfonamide | Calc'd 519.0 found 520.2 |
| 18-9 | 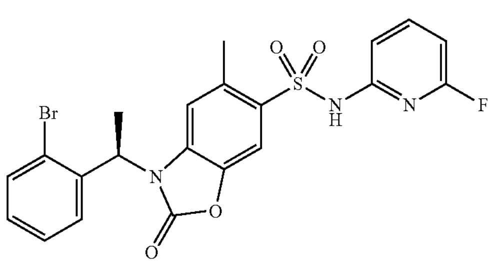 [SMILES: Cc1cc2c(cc1S(=O)(=O)Nc1cccc(F)n1)oc(=O)n2[C@H](C)c1ccccc1Br] | 3-[(1R)-1-(2-bromophenyl)ethyl]-N-(6-fluoropyridin-2-yl)-5-methyl-2-oxo-2,3-dihydro-1,3-benzoxazole-6-sulfonamide | Calc'd 505.0 found 506.1 |

TABLE 11-continued

| Exp No. | Structure | Name | Mass [M + H]+ |
|---|---|---|---|
| 18-10 | 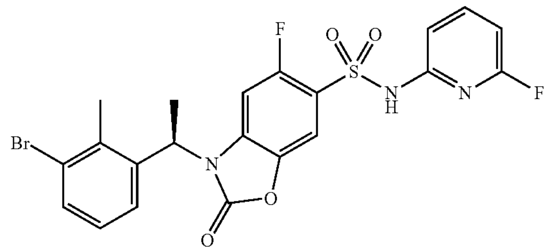 [SMILES: Cc1c(Br)cccc1[C@@H](C)n1c(=O)oc2cc(S(=O)(=O)Nc3cccc(F)n3)c(F)cc21] | 3-[(1R)-1-(3-bromo-2-methylphenyl)ethyl]-N-(6-fluoropyridin-2-yl)-5-fluoro-2-oxo-2,3-dihydro-1,3-benzoxazole-6-sulfonamide | Calc'd 523.0 found 524.2 |

Example 18

Preparation 3-{(1R)-1-[2-(aminomethyl)-3-methylphenyl]ethyl}-5-fluoro-N-(6-fluoropyridin-2-yl)-2-oxo-2,3-dihydro-1,3-benzoxazole-6-sulfonamide (Compound 19-1)

Scheme 18 illustrates preparation of additional compounds of the invention by derivative reaction of Compound 14-4 prepared in accordance with the procedure of Example 13.

was heated to 90° C. overnight, cooled to room temperature (rt) and diluted with EA, then washed with water brine and dried over Na$_2$SO$_4$. After filtration and concentration, the crude residue was taken up with DCM (5 mL), then TFA (1 mL) was added. The mixture was stirred at rt for 1 hour and concentrated. The concentrate was purified by reverse phase chromatography (5-75% MeCN in water w/0.1% TFA, C18 column) to yield 19-1 as the TFA salt. $^1$H NMR δ (ppm) (DMSO-d$_6$): 7.89 (1H, d, J=5.79 Hz), 7.71-7.77 (2H, m), 7.46 (1H, t, J=7.75 Hz), 7.37 (1H, d, J=7.65 Hz), 7.09 (1H, d, J=10.04 Hz), 6.92 (1H, dd, J=7.92, 1.98 Hz), 6.58 (1H, dd,

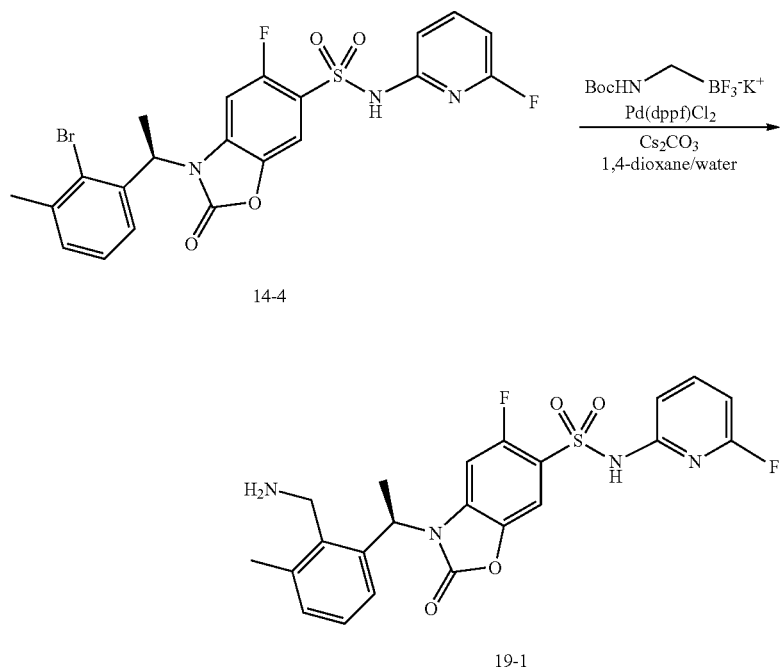

Scheme 18

Into a reaction vessel was placed, compound 14-4, prepared in accordance with Example 13, (52 mg, 0.1 mmol), commercial Potassium N-Boc-amino-methyltrifluoroborate (47 mg, 0.2 mmol), Cs$_2$CO$_3$ (97 mg, 0.3 mmol), Pd(dppf) Cl$_2$CH$_2$Cl$_2$ Adduct (8.1 mg, 9.93 μmol) dissolved in degassed water (0.5 ml) and 1,4-dioxane (5 ml). The mixture J=8.02, 2.48 Hz), 5.88-5.93 (1H, m), 4.24-4.33 (2H, m), 2.45 (3H, s), 1.93 (3H, d, J=7.08 Hz). HRMS C22H20F2N4O4S [M+H] calc: 475.1246, obs: 475.1242

The following compounds were prepared from 18-5, 18-6, 18-8, 18-9, or 18-10, by the synthetic sequence illustrated in Scheme 18:

TABLE 12

| Exp No. | Structure | Name | Mass [M + H]+ |
|---|---|---|---|
| 19-2 | 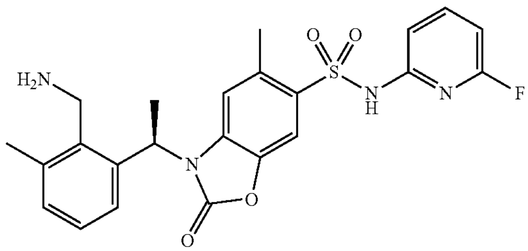 [SMILES: Cc1cc2c(cc1S(=O)(=O)Nc1cccc(F)n1)oc(=O)n2[C@H](C)c1cccc(C)c1CN] | 3-{(1R)-1-[2-(aminomethyl)-3-methylphenyl]ethyl}-N-(6-fluoropyridin-2-yl)-5-methyl-2-oxo-2,3-dihydro-1,3-benzoxazole-6-sulfonamide | Cacl'd 470.1 found 471.3 |
| 19-3 | 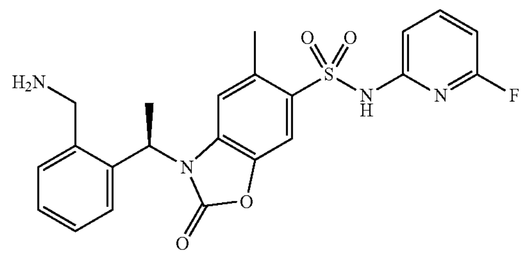 [SMILES: Cc1cc2c(cc1S(=O)(=O)Nc1cccc(F)n1)oc(=O)n2[C@H](C)c1ccccc1CN] | 3-{(1R)-1-[2-(aminomethyl)phenyl]ethyl}-N-(6-fluoropyridin-2-yl)-5-methyl-2-oxo-2,3-dihydro-1,3-benzoxazole-6-sulfonamide | Cacl'd 456.1 found 457.2 |
| 19-4 | 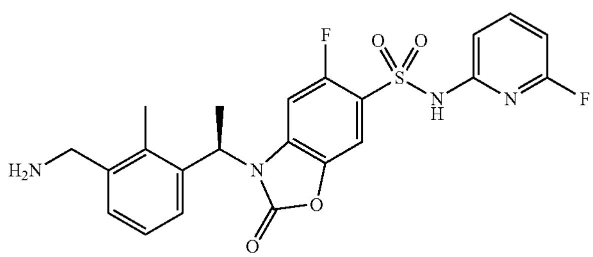 [SMILES: Cc1c(CN)cccc1[C@@H](C)n1c(=O)oc2cc(S(=O)(=O)Nc3cccc(F)n3)c(F)cc21] | 3-{(1R)-1-[3-(aminomethyl)-2-methylphenyl]ethyl}-5-fluoro-N-(6-fluoropyridin-2-yl)-2-oxo-2,3-dihydro-1,3-benzoxazole-6-sulfonamide | Cacl'd 474.1 found 475.3 |
| 19-5 | 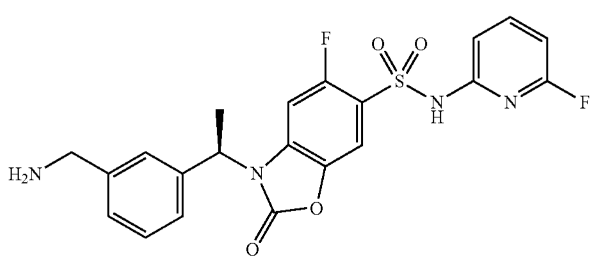 [SMILES: C[C@H](c1cccc(CN)c1)n1c(=O)oc2cc(S(=O)(=O)Nc3cccc(F)n3)c(F)cc21] | 3-{(1R)-1-[3-(aminomethyl)phenyl]ethyl}-5-fluoro-N-(6-fluoropyridin-2-yl)-2-oxo-2,3-dihydro-1,3-benzoxazole-6-sulfonamide | Cacl'd 460.1 found 461.3 |
| 19-6 | 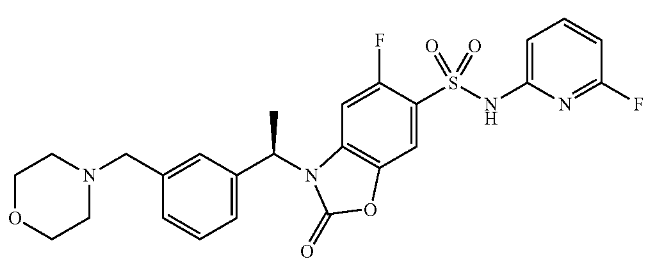 [SMILES: C[C@H](c1cccc(CN2CCOCC2)c1)n1c(=O)oc2cc(S(=O)(=O)Nc3cccc(F)n3)c(F)cc21] | 5-fluoro-N-(6-fluoropyridin-2-yl)-3-{(1R)-1-[3-(morpholin-4-ylmethyl)phenyl]ethyl}-2-oxo-2,3-dihydro-1,3-benzoxazole-6-sulfonamide | Cacl'd 530.1 found 531.4 |
| 19-7 | 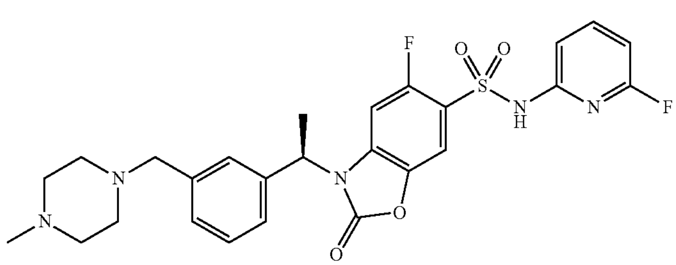 [SMILES: C[C@H](c1cccc(CN2CCN(C)CC2)c1)n1c(=O)oc2cc(S(=O)(=O)Nc3cccc(F)n3)c(F)cc21] | 5-fluoro-N-(6-fluoropyridin-2-yl)-3-[(1R)-1-{3-[(4-methylpiperazin-1-yl)methyl]phenyl}ethyl]-2-oxo-2,3-dihydro-1,3-benzoxazole-6-sulfonamide | Cacl'd 543.2 found 544.4 |

TABLE 12-continued

| Exp No. | Name | Mass [M + H]+ |
|---|---|---|
| 19-8 | 3-[(1R)-1-{3-[(dimethylamino)methyl]phenyl}ethyl]-5-fluoro-N-(6-fluoropyridin-2-yl)-2-oxo-2,3-dihydro-1,3-benzoxazole-6-sulfonamide | Cacl'd 488.1 found 489.3 |
| 19-9 | 5-fluoro-N-(6-fluoropyridin-2-yl)-3-[(1R)-1-{3-[(3-fluoropyrrolidin-1-yl)methyl]phenyl}ethyl]-2-oxo-2,3-dihydro-1,3-benzoxazole-6-sulfonamide | Cacl'd 532.1 found 533.2 |
| 19-10 | 3-[(1R)-1-{3-[(tert-butylamino)methyl]phenyl]ethyl}-5-fluoro-N-(6-fluoropyridin-2-yl)-2-oxo-2,3-dihydro-1,3-benzoxazole-6-sulfonamide | Cacl'd 516.2 found 517.4 |
| 19-11 | 3-{(1R)-1-[3-(2-aminoethyl)phenyl]ethyl}-5-fluoro-N-(6-fluoropyridin-2-yl)-2-oxo-2,3-dihydro-1,3-benzoxazole-6-sulfonamide | Cacl'd 474.1 found 475.4 |
| 19-12 | 3-{(1R)-1-[3-(2-aminoethyl)-2-methylphenyl]ethyl{-5-fluoro-N-(6-fluoropyridin-2-yl)-2-oxo-2,3-dihydro-1,3-benzoxazole-6-sulfonamide | Cacl'd 488.1 found 489.3 |

Example 19

Preparation 5-fluoro-N-(6-fluoropyridin-2-yl)-2-oxo-3-{(1R)-1-[2-(pyrrolidin-2-yl)phenyl]ethyl}-2,3-dihydro-1,3-benzoxazole-6-sulfonamide (Compound 20-1)

Scheme 19 illustrates preparation of additional compounds of the invention by derivative reaction of Compound 18-4 prepared in accordance with the procedure of Example 13 from appropriate precursors.

Scheme 19

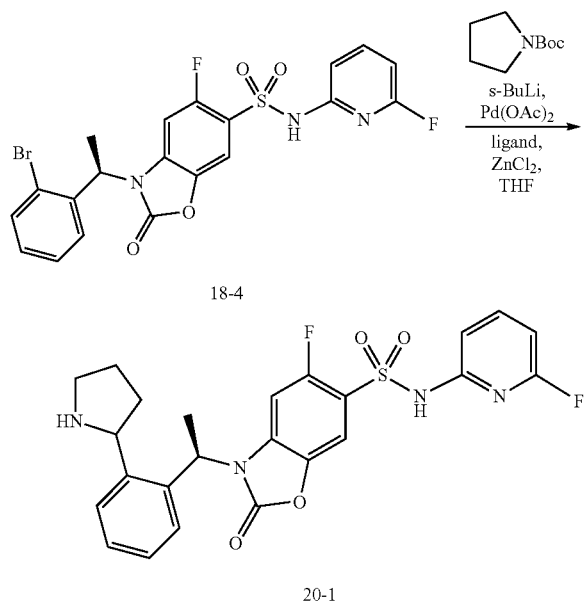

Into a stirred solution of N-Boc pyrrolidine (171 mg, 1.0 mmol) in dry THF (5 mL) at −30° C. under nitrogen was added dropwise sec-BuLi (927 uL, 1.3 mmol, 1.4M). The resulting mixture was stirred at −30° C. for 5 min. Then $ZnCl_2$ (0.6 mL, 1.0 M) was added dropwise. The resulted mixture was stirred at −30° C. for 30 min and allowed to warm to rt and stirred for another 30 min. To this stirred solution, bromo compound 18-4 (63 mg, 0.123 mmol) was added following by the addition of $PdOAc_2$ (2 mg, 0.009 mmol), Tri-tert-butylphosphonium tetrafluoroborate (3 mg, 0.011 mmol). The mixture was blowed with nitrogen for 2 min and sealed. The mixture was stirred at rt overnight. Diluted with water and extracted with EA. The organics were dried over Na2SO4 and filtered, concentrated. The residue was dissolved in DCM (5 mL) and treated with TFA (1 mL). The mixture was stirred at rt for 1 hour and concentrated. reverse phase chromatography (5-75% MeCN in water w/0.1% TFA, C18 column) to yield 20-1 as the TFA salt. $^1$H NMR δ (ppm)(DMSO-$d_6$): 7.88-7.94 (1H, m), 7.69-7.82 (2H, m), 7.42-7.55 (3H, m), 6.87-6.94 (1H, m), 6.75 (1H, dd, J=15.49, 9.96 Hz), 6.55-6.62 (1H, m), 5.89-5.97 (1H, m), 3.70-3.77 (1H, m), 3.57-3.46 (1H, m), 3.11-3.17 (2H, m), 1.87-1.98 (4H, m), 1.93 (3H, d, J=7.08 Hz). HRMS C24H22F2N4O4S [M+H] calc: 501.1403, obs: 501.1390

The following compounds were prepared from 14-4, 18-5 by the synthetic sequence illustrated in Scheme 19:

TABLE 13

| Exp No. | Structure | Name | Exact Mass [M + H]+ |
|---|---|---|---|
| 20-2 | 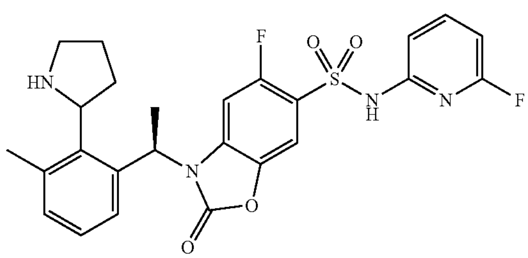 [SMILES: Cc1cccc([C@@H](C)n2c(=O)oc3cc(S(=O)(=O)Nc4cccc(F)n4)c(F)cc32)c1C1CCCN1] | 5-fluoro-N-(6-fluoropyridin-2-yl)-3-{(1R)-1-[3-methyl-2-(pyrrolidin-2-yl)phenyl]ethyl}-2-oxo-2,3-dihydro-1,3-benzoxazole-6-sulfonamide | Calc'd 515.1559, found 515.1554 |
| 20-3 | 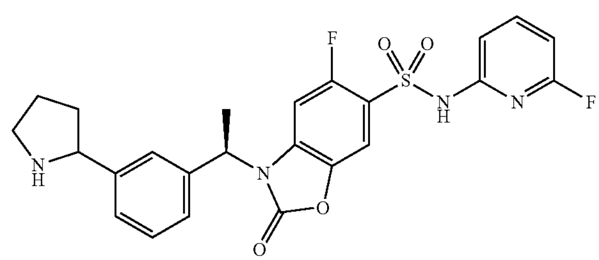 [SMILES: C[C@H](c1cccc(C2CCCN2)c1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[3-(pyrrolidin-2-yl)phenyl]ethyl}-2,3-dihydro-1,3-benzoxazole-6-sulfonamide | Calc'd 501.1403, found 501.1400 |

Example 20

Preparation 3-{(1R)-1-[3-(3-amino-3-methylbut-1-yn-1-yl)phenyl]ethyl}-5-fluoro-N-(6-fluoropyridin-2-yl)-2-oxo-2,3-dihydro-1,3-benzoxazole-6-sulfonamide (Compound 21-1)

Scheme 20 illustrates preparation of additional compounds of the invention by derivative reaction of Compound 18-5 prepared in accordance with the procedure of Example 13.

Scheme 20

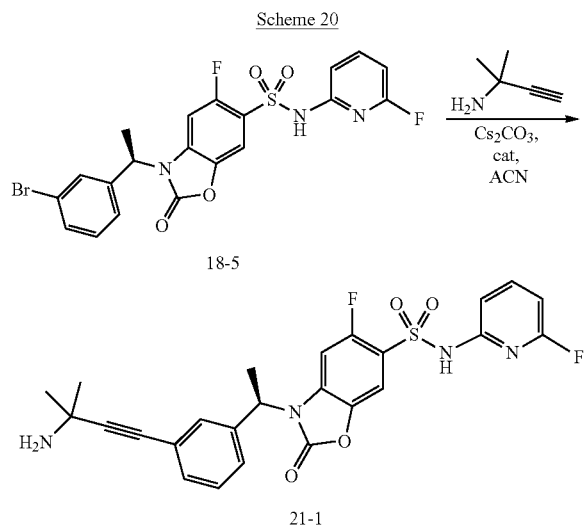

A solution of 18-5 (50 mg, 0.098 mmol), 2-methylbut-3-yn-2-amine (12.2 mg, 0.15 mmol), $Cs_2CO_3$ (96 mg, 0.294 mmol), and (2-Dicyclohexylphosphino-2',4',6'-triisopropyl-1,1'-buphenyl)[2-(2-aminoethyl)phenyl]Palladium(II) chloride (7.7 mg, 20 μmol) in degassed MeCN (1 mL) was heated to 85° C. for 18 hours under an atmosphere of nitrogen. Upon cooling to room temperature, the reaction was filtered and concentrated in vacuo. Residue was purified via reverse phase prep HPLC (5-70% MeCN in water w/0.1% TFA, C18 column) to yield 3-{(1R)-1-[3-(3-amino-3-methylbut-1-yn-1-yl)phenyl]ethyl}-5-fluoro-N-(6-fluoropyridin-2-yl)-2-oxo-2,3-dihydro-1,3-benzoxazole-6-sulfonamide 21-1 as the TFA salt. $^1$H NMR δ (ppm)(DMSO-$d_6$): 8.64 (1H, s), 7.83-7.90 (1H, m), 7.52-7.57 (1H, m), 7.40-7.45 (3H, m), 6.92 (1H, d, J=7.97 Hz), 6.74 (1H, dd, J=8.00, 2.33 Hz), 5.76 (1H, s), 5.60-5.88 (1H, m), 2.95 (1H, s), 1.85 (3H, d, J=7.15 Hz), 1.62 (6H, s).

The following compounds were prepared from 14-4, 18-5, 18-8 by the synthetic sequence illustrated in Scheme 20:

TABLE 14

| Exp. No. | Structure | Name | Mass [M + H]+ |
|---|---|---|---|
| 21-2 | 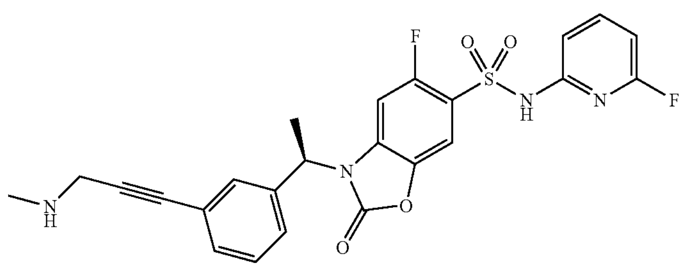 [SMILES: CNCC#Cc1cccc([C@@H](C)n2c(=O)oc3cc(S(=O)(=O)Nc4cccc(F)n4)c(F)cc32)c1] | 5-fluoro-N-(6-fluoropyridin-2-yl)-3-[(1R)-1-{3-[3-(methylamino)prop-1-yn-1-yl]phenyl}ethyl]-2-oxo-2,3-dihydro-1,3-benzoxazole-6-sulfonamide | Cacl'd 498.1 found 499.3 |
| 21-3 | 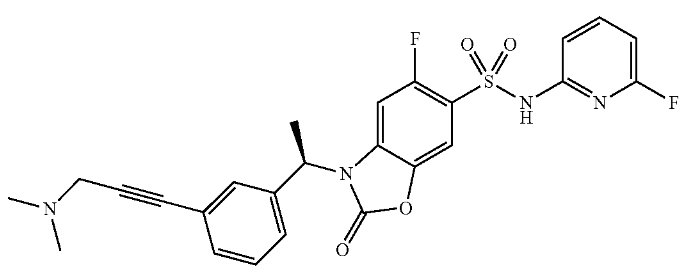 [SMILES: C[C@H](c1cccc(C#CCN(C)C)c1)n1c(=O)oc2cc(S(=O)(=O)Nc3cccc(F)n3)c(F)cc21] | 3-[(1R)-1-{3-[3-(dimethylamino)prop-1-yn-1-yl]phenyl}ethyl]-5-fluoro-N-(6-fluoropyridin-2-yl)-2-oxo-2,3-dihydro-1,3-benzoxazole-6-sulfonamide | Cacl'd 512.1 found 513.1 |
| 21-4 | 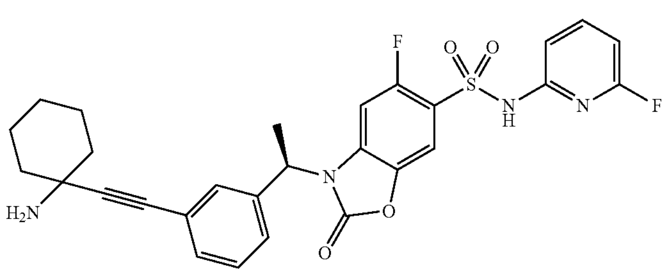 [SMILES: C[C@H](c1cccc(C#CC2(N)CCCCC2)c1)n1c(=O)oc2cc(S(=O)(=O)Nc3cccc(F)n3)c(F)cc21] | 3-[(1R)-1-{3-[(1-aminocyclohexyl)ethynyl]phenyl}ethyl]-5-fluoro-N-(6-fluoropyridin-2-yl)-2-oxo-2,3-dihydro-1,3-benzoxazole-6-sulfonamide | Cacl'd 552.2 found 553.1 |

TABLE 14-continued

| Exp. No. | Structure | Name | Mass [M + H]+ |
|---|---|---|---|
| 21-5 | 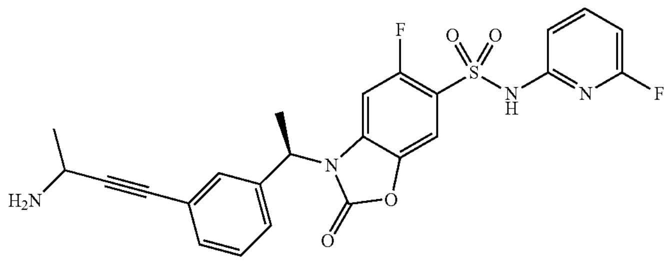 [SMILES: CC(N)C#Cc1cccc([C@@H](C)n2c(=O)oc3cc(S(=O)(=O)Nc4cccc(F)n4)c(F)cc32)c1] | 3-{(1R)-1-[3-(3-aminobut-1-yn-1-yl)phenyl]ethyl}-5-fluoro-N-(6-fluoropyridin-2-yl)-2-oxo-2,3-dihydro-1,3-benzoxazole-6-sulfonamide | Cacl'd 498.1 found 499.1 |
| 21-6 | 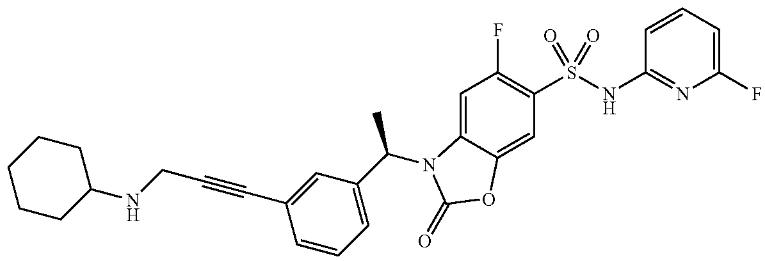 [SMILES: C[C@H](c1cccc(C#CCNC2CCCCC2)c1)n1c(=O)oc2cc(S(=O)(=O)Nc3cccc(F)n3)c(F)cc21] | 3-[(1R)-1-{3-[3-(cyclohexylamino)prop-1-yn-1-yl]phenyl}ethyl]-5-fluoro-N-(6-fluoropyridin-2-yl)-2-oxo-2,3-dihydro-1,3-benzoxazole-6-sulfonamide | Cacl'd 566.2 found 567.1 |
| 21-7 | 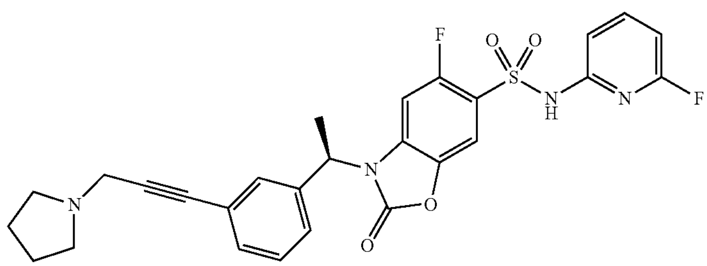 [SMILES: C[C@H](c1cccc(C#CCN2CCCC2)c1)n1c(=O)oc2cc(S(=O)(=O)Nc3cccc(F)n3)c(F)cc21] | 5-fluoro-N-(6-fluoropyridin-2-yl)-2-oxo-3-[(1R)-1-{3-[3-(pyrrolidin-1-yl)prop-1-yn-1-yl]phenyl}ethyl]-2,3-dihydro-1,3-benzoxazole-6-sulfonamide | Cacl'd 538.2 found 539.1 |
| 21-8 | 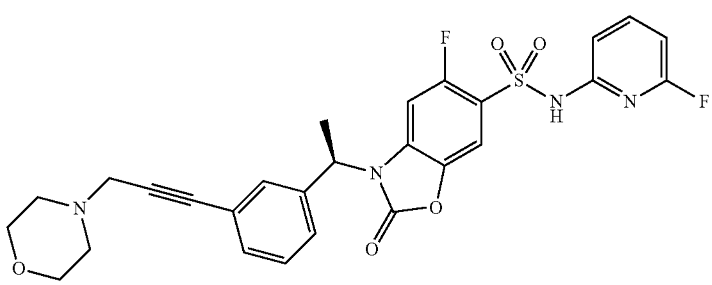 [SMILES: C[C@H](c1cccc(C#CCN2CCOCC2)c1)n1c(=O)oc2cc(S(=O)(=O)Nc3cccc(F)n3)c(F)cc21] | 5-fluoro-N-(6-fluoropyridin-2-yl)-3-[(1R)-1-{3-[3-(morpholin-4-yl)prop-1-yn-1-yl]phenyl}ethyl]-2-oxo-2,3-dihydro-1,3-benzoxazole-6-sulfonamide | Cacl'd 554.1 found 555.1 |
| 21-9 | 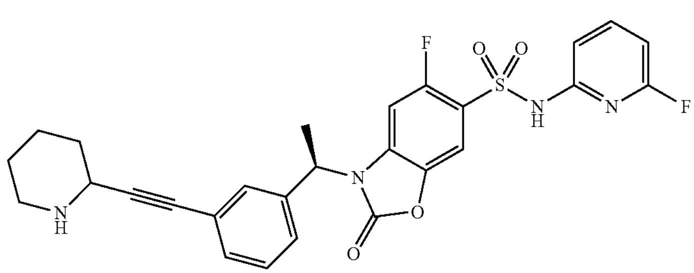 [SMILES: C[C@H](c1cccc(C#CC2CCCCN2)c1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[3-(piperidin-2-ylethynyl)phenyl]ethyl}-2,3-dihydro-1,3-benzoxazole-6-sulfonamide | Cacl'd 538.2 found 539.0 |

TABLE 14-continued

| Exp. No. | Structure | Name | Mass [M + H]+ |
|---|---|---|---|
| 21-10 | 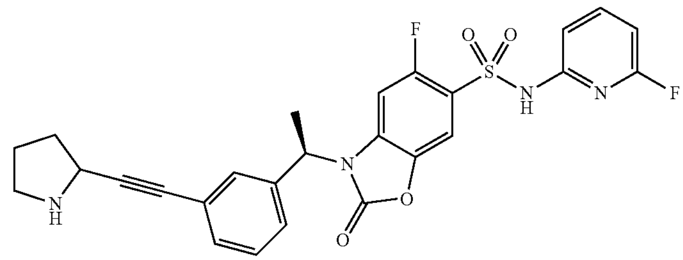 [SMILES: C[C@H](c1cccc(C#CC2CCCN2)c1)n1c(=O)oc2cc(S(=O)(=O)Nc3cccc(F)n3)c(F)cc21] | 5-fluoro-N-(6-fluoropyridin-2-yl)-2-oxo-3-{(1R)-1-[3-(pyrrolidin-2-ylethynyl)phenyl]ethyl}-2,3-dihydro-1,3-benzoxazole-6-sulfonamide | Cacl'd 524.1 found 525.1 |
| 21-11 | 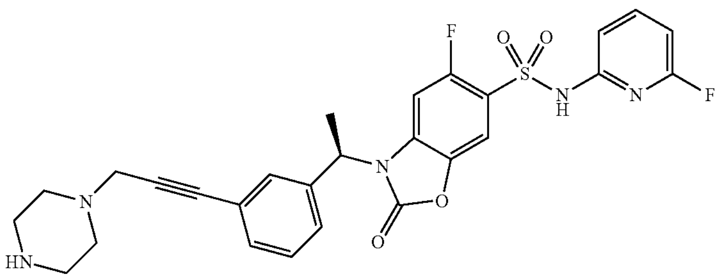 [SMILES: C[C@H](c1cccc(C#CCN2CCNCC2)c1)n1c(=O)oc2cc(S(=O)(=O)Nc3cccc(F)n3)c(F)cc21] | 5-fluoro-N-(6-fluoropyridin-2-yl)-2-oxo-3-[(1R)-1-{3-[3-(piperazin-1-yl)prop-1-yn-1-yl]phenyl}ethyl]-2,3-dihydro-1,3-benzoxazole-6-sulfonamide | Cacl'd 553.2 found 554.1 |
| 21-12 | 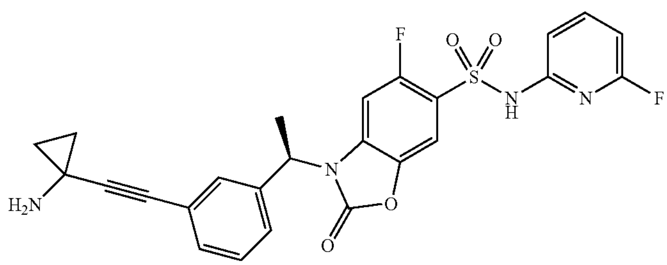 [SMILES: C[C@H](c1cccc(C#CC2(N)CC2)c1)n1c(=O)oc2cc(S(=O)(=O)Nc3cccc(F)n3)c(F)cc21] | 3-[(1R)-1-{3-[(1-aminocyclopropyl)ethynyl]phenyl}ethyl]-5-fluoro-N-(6-fluoropyridin-2-yl)-2-oxo-2,3-dihydro-1,3-benzoxazole-6-sulfonamide | Cacl'd 510.1 found 511.4 |
| 21-13 | 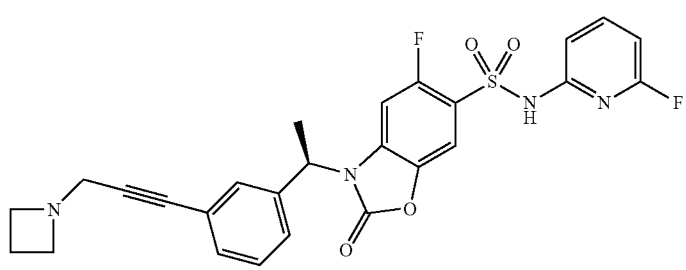 [SMILES: C[C@H](c1cccc(C#CCN2CCC2)c1)n1c(=O)oc2cc(S(=O)(=O)Nc3cccc(F)n3)c(F)cc21] | 3-[(1R)-1-{3-[3-(azetidin-1-yl)prop-1-yn-1-yl]phenyl}ethyl]-5-fluoro-N-(6-fluoropyridin-2-yl)-2-oxo-2,3-dihydro-1,3-benzoxazole-6-sulfonamide | Cacl'd 524.1 found 525.3 |
| 21-14 | 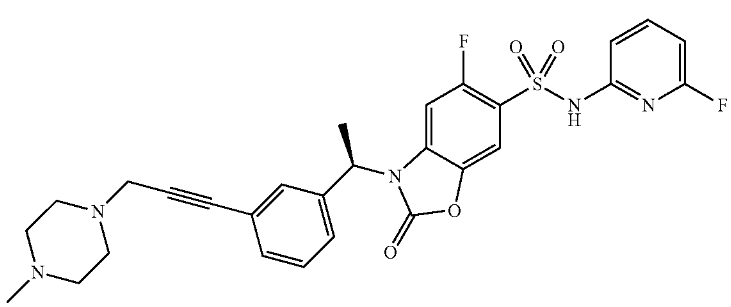 [SMILES: C[C@H](c1cccc(C#CCN2CCN(C)CC2)c1)n1c(=O)oc2cc(S(=O)(=O)Nc3cccc(F)n3)c(F)cc21] | 5-fluoro-N-(6-fluoropyridin-2-yl)-3-[(1R)-1-{3-[3-(4-methylpiperazin-1-yl)prop-1-yn-1-yl]phenyl}ethyl]-2-oxo-2,3-dihydro-1,3-benzoxazole-6-sulfonamide | Cacl'd 567.2 found 568.1 |

TABLE 14-continued

| Exp. No. | Structure | Name | Mass [M + H]+ |
|---|---|---|---|
| 21-15 | 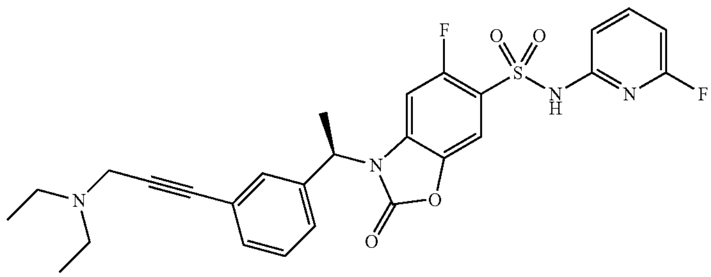 [SMILES: CCN(CC)CC#Cc1cccc([C@@H](C)n2c(=O)oc3cc(S(=O)(=O)Nc4cccc(F)n4)c(F)cc32)c1] | 3-[(1R)-1-{3-[3-(diethylamino)prop-1-yn-1-yl]phenyl}ethyl]-5-fluoro-N-(6-fluoropyridin-2-yl)-2-oxo-2,3-dihydro-1,3-benzoxazole-6-sulfonamide | Cacl'd 540.2 found 541.1 |
| 21-16 | 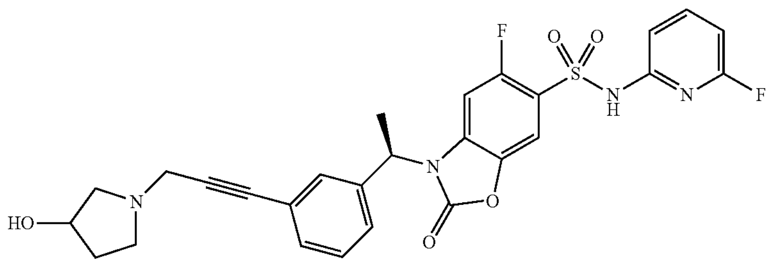 [SMILES: C[C@H](c1cccc(C#CCN2CCC(O)C2)c1)n1c(=O)oc2cc(S(=O)(=O)Nc3cccc(F)n3)c(F)cc21] | 5-fluoro-N-(6-fluoropyridin-2-yl)-3-[(1R)-1-{3-[3-(3-hydroxypyrrolidin-1-yl)prop-1-yn-1-yl]phenyl}ethyl]-2-oxo-2,3-dihydro-1,3-benzoxazole-6-sulfonamide | Cacl'd 554.2 found 555.1 |
| 21-17 | 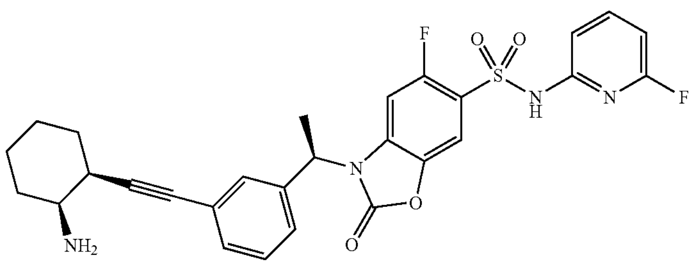 [SMILES: C[C@H](c1cccc(C#C[C@@H]2CCCC[C@@H]2N)c1)n1c(=O)oc2cc(S(=O)(=O)Nc3cccc(F)n3)c(F)cc21] | 3-[(1R)-1-(3-{[(1S,2S)-2-aminocyclohexyl]ethynyl}phenyl)ethyl]-5-fluoro-N-(6-fluoropyridin-2-yl)-2-oxo-2,3-dihydro-1,3-benzoxazole-6-sulfonamide | Cacl'd 552.2 found 553.1 |
| 21-18 | 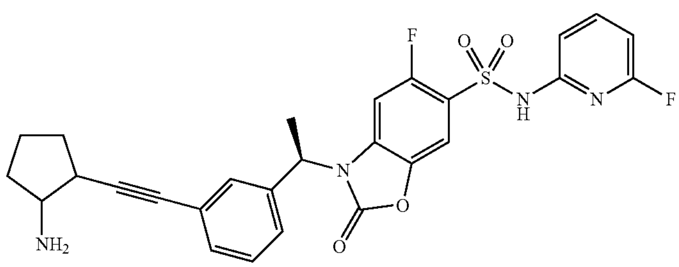 [SMILES: C[C@H](c1cccc(C#CC2CCCC2N)c1)n1c(=O)oc2cc(S(=O)(=O)Nc3cccc(F)n3)c(F)cc21] | 3-[(1R)-1-{3-[(2-aminocyclopentyl)ethynyl]phenyl}ethyl]-5-fluoro-N-(6-fluoropyridin-2-yl)-2-oxo-2,3-dihydro-1,3-benzoxazole-6-sulfonamide | Cacl'd 538.2 found 539.1 |
| 21-19 | 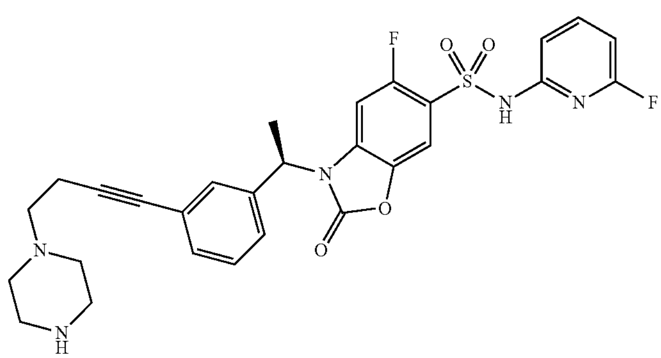 [SMILES: C[C@H](c1cccc(C#CCCN2CCNCC2)c1)n1c(=O)oc2cc(S(=O)(=O)Nc3cccc(F)n3)c(F)cc21] | 5-fluoro-N-(6-fluoropyridin-2-yl)-2-oxo-3-[(1R)-1-{3-[4-(piperazin-1-yl)but-1-yn-1-yl]phenyl}ethyl]-2,3-dihydro-1,3-benzoxazole-6-sulfonamide | Cacl'd 567.2 found 568.1 |

TABLE 14-continued

| Exp. No. | Structure | Name | Mass [M + H]+ |
|---|---|---|---|
| 21-20 | 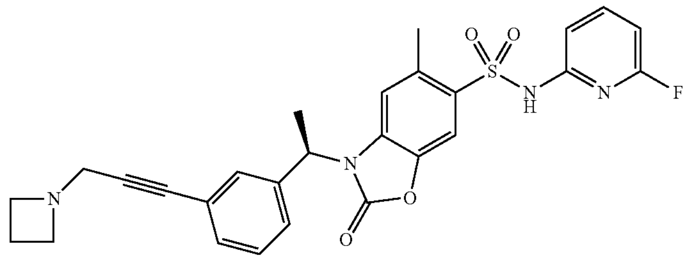 [SMILES: Cc1cc2c(cc1S(=O)(=O)Nc1cccc(F)n1)oc(=O)n2[C@H](C)c1cccc(C#CCN2CCC2)c1] | 3-[(1R)-1-{3-[3-(azetidin-1-yl)prop-1-yn-1-yl]phenyl}ethyl]-N-(6-fluoropyridin-2-yl)-5-methyl-2-oxo-2,3-dihydro-1,3-benzoxazole-6-sulfonamide | Cacl'd 520.2 found 521.2 |
| 21-21 | 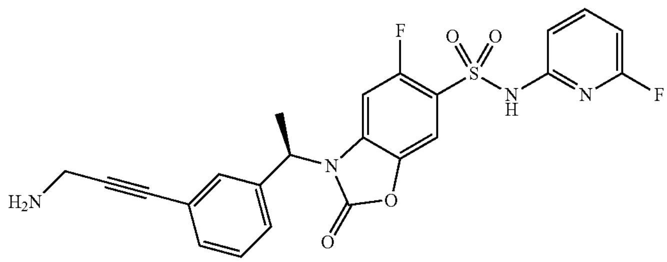 [SMILES: C[C@H](c1cccc(C#CCN)c1)n1c(=O)oc2cc(S(=O)(=O)Nc3cccc(F)n3)c(F)cc21] | 3-{(1R)-1-[3-(3-aminoprop-1-yn-1-yl)phenyl]ethyl}-5-fluoro-N-(6-fluoropyridin-2-yl)-2-oxo-2,3-dihydro-1,3-benzoxazole-6-sulfonamide | Cacl'd 484.1 found 485.2 |
| 21-22 | 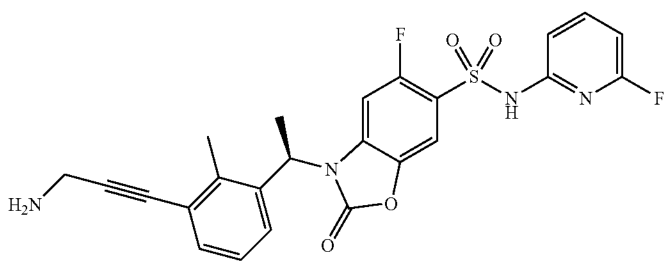 [SMILES: Cc1c(C#CCN)cccc1[C@@H](C)n1c(=O)oc2cc(S(=O)(=O)Nc3cccc(F)n3)c(F)cc21] | 3-{(1R)-1-[3-(3-aminoprop-1-yn-1-yl)-2-methylphenyl]ethyl}-5-fluoro-N-(6-fluoropyridin-2-yl)-2-oxo-2,3-dihydro-1,3-benzoxazole-6-sulfonamide | Cacl'd 498.1 found 499.1 |
| 21-23 | 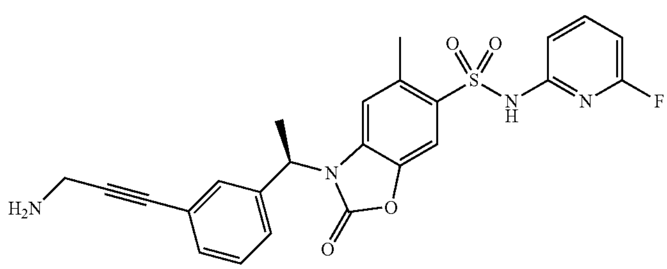 [SMILES: Cc1cc2c(cc1S(=O)(=O)Nc1cccc(F)n1)oc(=O)n2[C@H](C)c1cccc(C#CCN)c1] | 3-{(1R)-1-[3-(3-aminoprop-1-yn-1-yl)phenyl]ethyl}-N-(6-fluoropyridin-2-yl)-5-methyl-2-oxo-2,3-dihydro-1,3-benzoxazole-6-sulfonamide | Cacl'd 480.1 found 481.2 |
| 21-24 | 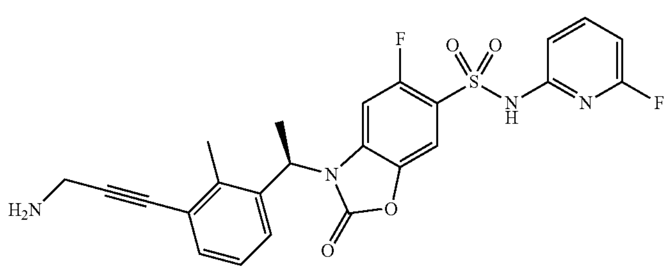 [SMILES: Cc1c(C#CCN)cccc1[C@@H](C)n1c(=O)oc2cc(S(=O)(=O)Nc3cccc(F)n3)c(F)cc21] | 3-{(1R)-1-[3-(3-aminoprop-1-yn-1-yl)-2-methylphenyl]ethyl}-N-(6-fluoropyridin-2-yl)-5-methyl-2-oxo-2,3-dihydro-1,3-benzoxazole-6-sulfonamide | Cacl'd 494.1 found 495.2 |

TABLE 14-continued

| Exp. No. | Structure | Name | Mass [M + H]+ |
|---|---|---|---|
| 21-25 | 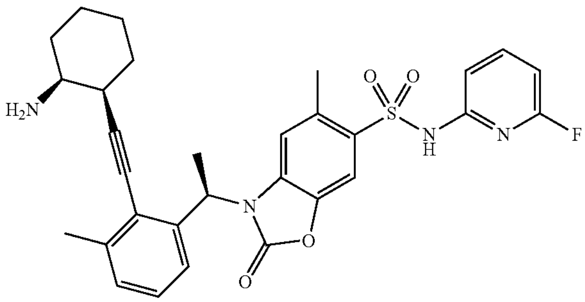 [SMILES: Cc1cc2c(cc1S(=O)(=O)Nc1cccc(F)n1)oc(=O)n2[C@H](C)c1cccc(C)c1C#C[C@@H]1CCCC[C@@H]1N] | 3-[(1R)-1-(2-{[(1S,2S)-2-aminocyclohexyl]-ethynyl}-3-methylphenyl)ethyl]-N-(6-fluoropyridin-2-yl)-5-methyl-2-oxo-2,3-dihydro-1,3-benzoxazole-6-sulfonamide | Cacl'd 562.2 found 563.2 |
| 21-26 | 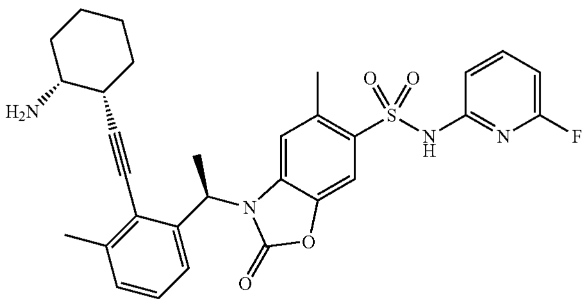 [SMILES: Cc1cc2c(cc1S(=O)(=O)Nc1cccc(F)n1)oc(=O)n2[C@H](C)c1cccc(C)c1C#C[C@H]1CCCC[C@H]1N] | 3-[(1R)-1-(2-{[(1R,2R)-2-aminocyclohexyl]-ethynyl}-3-methylphenyl)ethyl]-N-(6-fluoropyridin-2-yl)-5-methyl-2-oxo-2,3-dihydro-1,3-benzoxazole-6-sulfonamide | Cacl'd 562.2 found 563.1 |
| 21-27 | 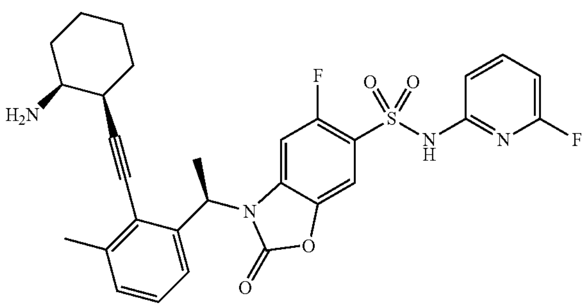 [SMILES: Cc1cccc([C@@H](C)n2c(=O)oc3cc(S(=O)(=O)Nc4cccc(F)n4)c(F)cc32)c1C#C[C@@H]1CCCC[C@@H]1N] | 3-[(1R)-1-(2-{[(1S,2S)-2-aminocyclohexyl]-ethynyl}-3-methylphenyl)ethyl]-5-fluoro-N-(6-fluoropyridin-2-yl)-2-oxo-2,3-dihydro-1,3-benzoxazole-6-sulfonamide | Cacl'd 566.2 found 567.2 |

Example 21

Preparation 3-{(1R)-1-[3-(3-aminopropyl)phenyl]ethyl}-5-fluoro-N-(6-fluoropyridin-2-yl)-2-oxo-2,3-dihydro-1,3-benzoxazole-6-sulfonamide (Compound 22-1)

Scheme 21 illustrates preparation of additional compounds of the invention by derivative reaction of Compound 21-23 prepared in accordance with the procedure of Example 20.

Scheme 21

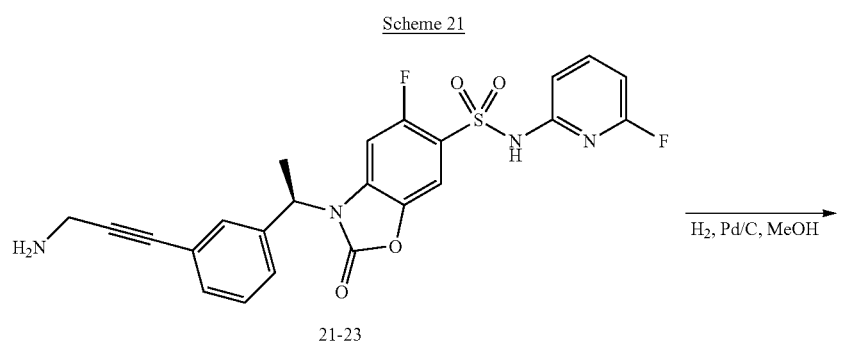

21-23

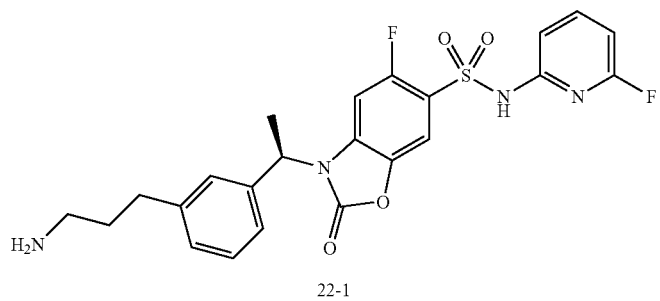

22-1

Methanol (10 mL) was added slowly under nitrogen to a 100 mL round-bottom flask charged with a magnetic stir-bar, Palladium on Carbon (72.8 mg, 0.068 mmol), and 21-23 (40 mg, 0.068 mmol). The vessel was evacuated, and backfilled with hydrogen (balloon), repeated 3×. The reaction was stirred at room temp for 3 h. Filtered through a plug of celite, washed with ethanol, concentrated, took up in DCM, added 1 mL of TFA. Purified on reverse phase gilson (5-70% MeCN in water w/0.1% TFA, C18 column) to yield 22-1 as the TFA salt. $^1$H NMR δ (ppm)(DMSO-$d_6$): 7.82-7.89 (2H, m), 7.69 (1H, s), 7.32-7.36 (2H, m), 7.29 (1H, s), 7.17 (1H, s), 6.92 (1H, d, J=7.97 Hz), 6.74 (1H, d, J=8.04 Hz), 5.56 (1H, d, J=7.81 Hz), 2.75-2.80 (2H, m), 2.62 (2H, t, J=7.85 Hz), 1.85 (3H, d, J=7.20 Hz), 1.79 (2H, t, J=8.89 Hz). LC-MS[M+1]: 489.3

The following compounds were prepared from 21-13, 21-21, 21-22 by the synthetic sequence illustrated in Scheme 21:

TABLE 15

| Exp. No. | Structure | Name | Mass [M + H]+ |
|---|---|---|---|
| 22-2 | 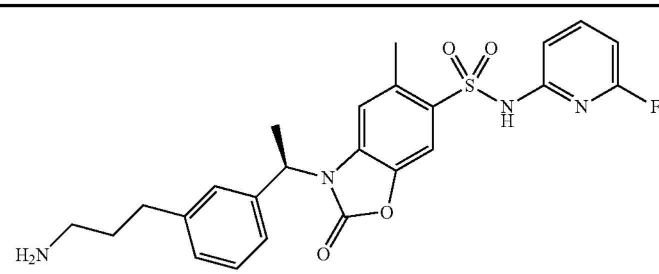 | 3-{(1R)-1-[3-(3-amino-propyl)phenyl]ethyl}-N-(6-fluoropyridin-2-yl)-5-methyl-2-oxo-2,3-dihydro-1,3-benzoxazole-6-sulfonamide | Cacl'd 484.2 found 485.2 |
| 22-3 | 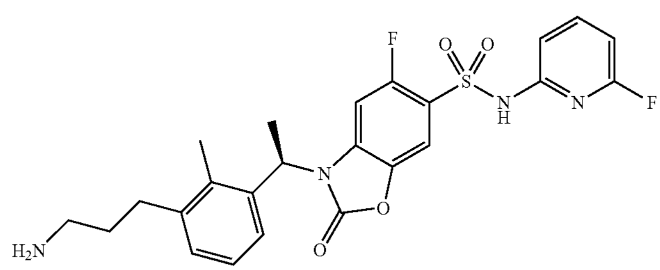 [SMILES: Cc1c(CCCN)cccc1[C@@H](C)n1c(=O)oc2cc(S(=O)(=O)Nc3cccc(F)n3)c(F)cc21] | 3-{(1R)-1-[3-(3-amino-propyl)-2-methylphenyl]ethyl}-5-fluoro-N-(6-fluoropyridin-2-yl)-2-oxo-2,3-dihydro-1,3-benzoxazole-6-sulfonamide | Cacl'd 502.2 found 503.2 |
| 22-4 | 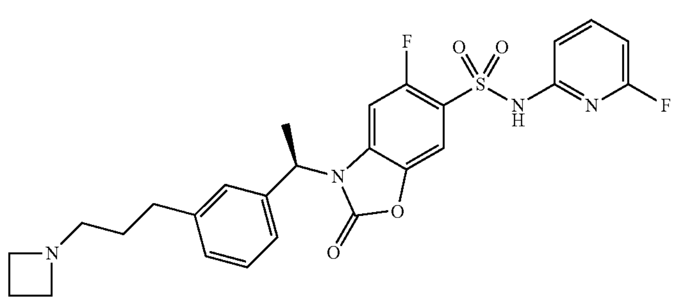 [SMILES: C[C@H](c1cccc(CCCN2CCC2)c1)n1c(=O)oc2cc(S(=O)(=O)Nc3cccc(F)n3)c(F)cc21] | 3-[(1R)-1-{3-[3-(azetidin-1-yl)propyl]phenyl}ethyl]-5-fluoro-N-(6-fluoro-pyridin-2-yl)-2-oxo-2,3-dihydro-1,3-benzoxazole-6-sulfonamide | Cacl'd 528.2 found 529.2 |

Example 22

Preparation 5-fluoro-N-(6-fluoropyridin-2-yl)-2-oxo-3-{(1R)-1-[2-(piperazin-1-yl)phenyl]ethyl}-2,3-dihydro-1,3-benzoxazole-6-sulfonamide (Compound 23-1)

Scheme 22 illustrates preparation of additional compounds of the invention by derivative reaction of Compound 18-4 prepared in accordance with the procedure of Example 18.

phenyl]ethyl}-2,3-dihydro-1,3-benzoxazole-6-sulfonamide 23-1 as the TFA salt. $^1$H NMR δ (ppm)(DMSO-$d_6$): 7.70-7.86 (3H, m), 7.38-7.47 (2H, m), 7.27 (1H, dd, J=7.69, 1.53 Hz), 6.87 (1H, dd, J=7.92, 1.99 Hz), 6.57 (1H, dd, J=8.02, 2.48 Hz), 6.47 (1H, d, J=9.94 Hz), 5.89-5.94 (1H, m), 4.23 (2H, dq, J=33.74, 7.10 Hz), 3.10-3.17 (2H, m), 1.86 (3H, d, J=7.18 Hz), 1.24-1.34 (4H, m). HRMS C24H23F2N5O4S [M+H] calc: 516.1512, obs: 516.1498

The following compounds were prepared from 18-9 by the synthetic sequence illustrated in Scheme 22:

TABLE 16

| Exp. No. | Structure | Name | Exact Mass [M + H]+ |
|---|---|---|---|
| 23-2 | 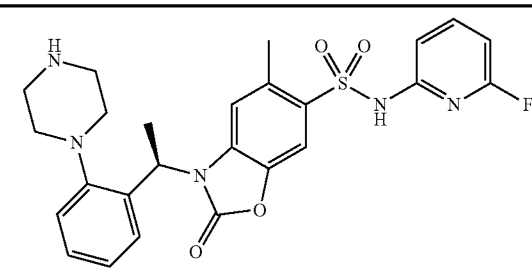 | N-(6-fluoropyridin-2-yl)-5-methyl-2-oxo-3-{(1R)-1-[2-(piperazin-1-yl)phenyl]ethyl}-2,3-dihydro-1,3-benzoxazole-6-sulfonamide | Calc'd 512.1762, found 512.1747 |

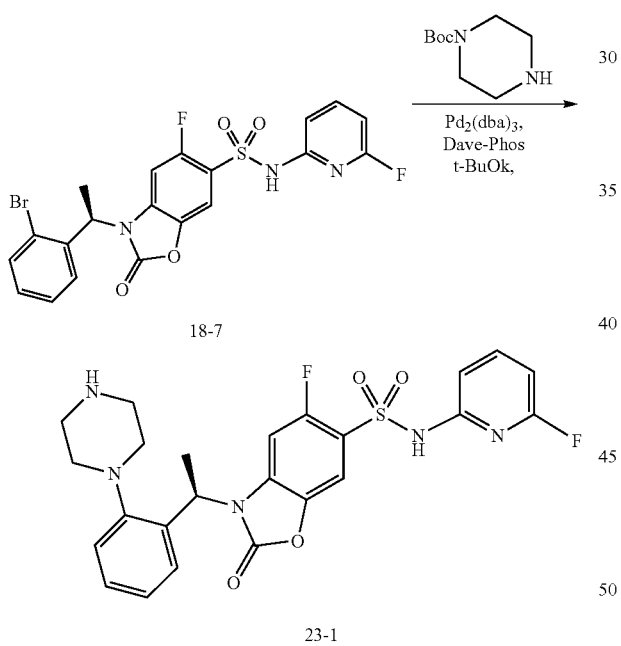

Scheme 22

Example 23

Preparation of 3-{(1R)-1-[2-(2-aminoethyl)phenyl]ethyl}-5-fluoro-N-(6-fluoropyridin-2-yl)-2-oxo-2,3-dihydro-1,3-benzoxazole-6-sulfonamide (Compound 24-2)

Scheme 23 illustrates preparation of additional compounds of the invention by derivative reaction of Compound 18-4 prepared in accordance with the procedure of Example 18.

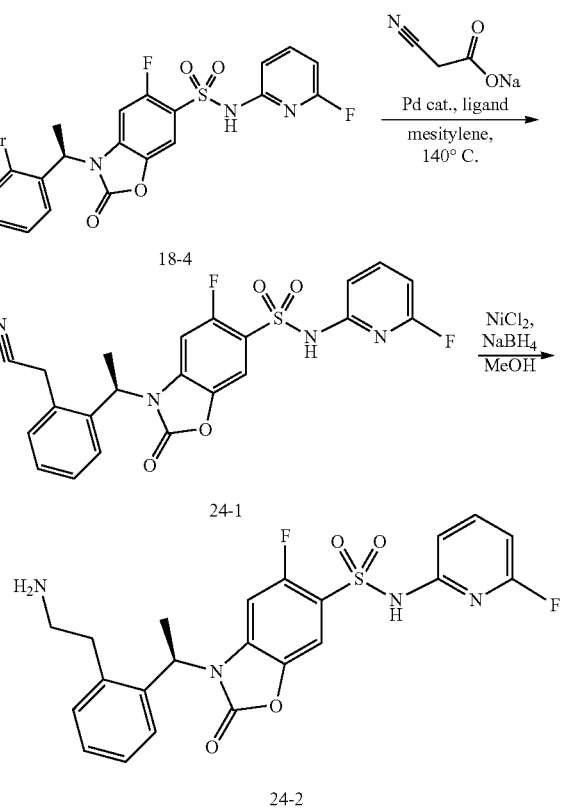

Scheme 23

The 2-bromo compound 18-4 (51 mg, 0.1 mmol), Pd2(dba)3 (9 mg, 0.01 mmol), Dave-phos (8 mg, 0.2 mmol), KOBut (56 mg, 0.5 mmol) and tert-butyl piperazine-1-carboxylate (93 mg, 0.5 mmol) were mixed in a 4 ml vial under N2. Then, dioxane (1 ml) was added under nitrogen and the mixture was blow with nitrogen for 2 min. The vial was sealed and was heated to 90° C. for 18 hours under an atmosphere of nitrogen. Upon cooling to room temperature, the reaction was filtered and concentrated in vacuo. Residue was taken up with DCM (5 ml) and treated with TFA (1 ml) and stirred at rt for 30 min. After concentration, the residue was purified via reverse phase prep HPLC (5-70% MeCN in water w/0.1% TFA, C18 column) to yield 5-fluoro-N-(6-fluoropyridin-2-yl)-2-oxo-3-{(1R)-1-[2-(piperazin-1-yl)

Preparation of 3-{(1R)-1-[2-(cyanomethyl)phenyl]ethyl}-5-fluoro-N-(6-fluoropyridin-2-yl)-2-oxo-2,3-dihydro-1,3-benzoxazole-6-sulfonamide (24-1)

The bromo-compound 18-4 (50 mg, 0.1 mmol) was mixed with sodium 2-cyanoacetate (16 mg, 0.15 mmol) and allylpalladium chloride dimer (4 mg, 0.01 mmol), 2-dicyclohexylphosphino-2',6'-dimethoxybiphenyl (12.3 mg, 0.03 mmol) and mesitylene (1 mL) under nitrogen. The mixture was blowed with nitrogen for 2 min and sealed. The mixture was heated upto 140° C. and stirred overnight. Cooled to rt and taken up in 10 mL of EtOAc, washed with water and brine. Combined organic layer was dried over sodium sulfate, filtered and concentrated in vacuo and purified on the Gilson reverse phase prep HPLC (5-70% MeCN in water w/0.1% TFA) (C18 column) to yield 24-1.

Preparation of 3-{(1R)-1-[2-(2-aminoethyl)phenyl]ethyl}-5-fluoro-N-(6-fluoropyridin-2-yl)-2-oxo-2,3-dihydro-1,3-benzoxazole-6-sulfonamide (Compound 24-2)

The starting material 24-1 (38 mg, not pure, 0.08 mmol) was dissolved in Methanol (5 mL) and $NiCl_2 \cdot 6H_2O$ (19 mg, 0.8 mmol) was added. Then, $NaBH_4$ (10 mg, 0.24 mmol) was added to this mixture and the reaction was turned to dark immediately. After 5 min, the reaction was concentrated and the residue was dissolved in DMSO and purified with Gilson HPLC (5-95% MeCN in water w/0.1% TFA, C18 column) to yield 24-2 as the TFA salt. $^1$H NMR δ (ppm)($CH_3OH$-$d_4$): 7.89 (1H, d, J=5.78 Hz), 7.71-7.77 (2H, m), 7.38-7.43 (2H, m), 7.29-7.31 (1H, m), 6.92 (1H, dd, J=7.92, 1.99 Hz), 6.83 (1H, d, J=10.02 Hz), 6.59 (1H, dd, J=8.02, 2.47 Hz), 5.80 (1H, q, J=7.04 Hz), 3.13-3.19 (2H, m), 2.98-3.06 (1H, m), 2.85-2.93 (1H, m), 1.90 (3H, d, J=7.12 Hz). HRMS C22H20F2N4O4S [M+H] calc: 475.1246, obs: 475.1236

The following compounds were prepared from 14-4 by the synthetic sequence illustrated in Scheme 23:

to the potential at which ~50% of the channels are inactivated was given followed by a hyperpolarizing 2 ms pulse to −120 mV and a 20 ms test pulse to −20 mV. The protocol was applied to cells in the absence, presence of compound and after washout. The temperature of PatchXpress® instruments was maintained at 22° C. The following recording solutions were used. Internal solution (mM): 30 CsCl, 5 HEPES, 10 EGTA, 120 CsF, 5 NaF, 2 $MgCl_2$, pH 7.3 with CsOH. External solution (mM): 120 NMDG, 40 NaCl, 1 KCl, 0.5 $MgCl_2$, 5 HEPES, 2.7 $CaCl_2$, pH 7.5 with NMDG-OH. Estimated $IC_{50}$ values were calculated based on at least two compound concentrations tested. For all electrophysiology experiments, offline analysis was used to correct for current rundown and to determine percent inhibition as a function of drug concentration. $IC_{50}$ values were determined by fitting to the Hill equation.

Various of the compounds exemplified above were assayed for activity and selectivity using the foregoing PatchXpress® technique. The results are reported in the following paragraph in a format expressing the identification of the compound with reference to Example number given to it in the Examples section, above (i.e. Ex2-5 refers to compound 2-5 presented in Scheme 2, above, and Ex4-5, refers to compound 4-5 presented in Table I following Scheme 4. Thus, Ex2-5: 1.7=152/ratio=316 identifies compound 2-5 as having 152 nM potency for the Nav 1.7 sodium ion channel (as measured by PatchExpress®) and a ratio of 316 Nav 1.5:Nav 1.7 potency, determined by PatchExpress® measurement. The following results are reported:

Ex2-5: 1.7=152/ratio=316; Ex3-5: 1.7=99/ratio=158; Ex4-4: 1.7=482/ratio=166; Ex4-5: 1.7=650/ratio=101; Ex5-9: 1.7=1142/ratio=26; Ex5-10: 1.7=961/ratio=>31; Ex5-11: 1.7=727/ratio=54; Ex7-5: 1.7=3/ratio=1398; Ex7-6: 1.7=460/ratio=123; Ex7-7 1.7=41/ratio=239; Ex7-8: 1.7=81/ratio=681; Ex7-9: 1.7=52/ratio=1475; Ex7-10: 1.7=127/ratio=331; Ex7-11: 1.7=65/ratio=461; Ex8-1: 1.7=50/ratio=546; Ex8-2: 1.7=434/ratio=23; Ex8-3: 1.7=14/ratio=2000; Ex8-4:

TABLE 17

| Exp No. | Structure | Name | Exact Mass [M + H]+ |
|---|---|---|---|
| 24-3 | 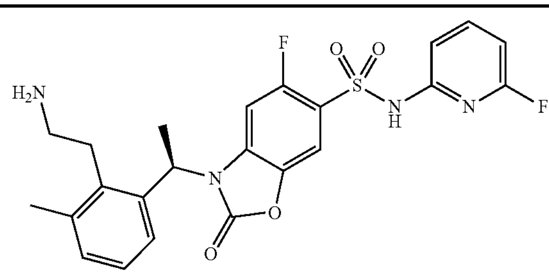 | 3-{(1R)-1-[2-(2-aminoethyl)-3-methylphenyl]-ethyl}-5-fluoro-N-(6-fluoropyridin-2-yl)-2-oxo-2,3-dihydro-1,3-benzoxazole-6-sulfonamide | Calc'd 489.1403, found 489.1387 |

Cell Based Assays for $Na_v$ 1.7 and $Na_v$ 1.5 Activity

Compounds were tested on human Nav1.7 and Nav1.5 channels stably expressed in HEK 293 cells.

Sodium Current Measurements on the PatchXpress 7000: To measure inactivated state block of sodium channels, test compounds were characterized in an automated PatchXpress® assay (Molecular Devices) using a double-pulse protocol on human Nav1.7 and Nav1.5 channels stably expressed in HEK 293 cells. Cells were held at a potential 20 mV negative to the potential at which ~50% of the channels are inactivated. A 8000 ms pre-pulse 7 mV positive 1.7=9/ratio=822; Ex8-5: 1.7=25/ratio=714; Ex8-6: 1.7=49/ratio=95; Ex8-7 1.7=108/ratio=>131; Ex8-8: 1.7=299/ratio=75; Ex8-9: 1.7=273/ratio=99; Ex8-10: 1.7=236/ratio=127; Ex9-1: 1.7=24/ratio=1525; Ex9-2: 1.7=124/ratio=84; Ex9-3: 1.7=300/ratio=68; Ex10-3: 1.7=39/ratio=1306; Ex11-1: 1.7=213/ratio=34; Ex12-4: 1.7=400/ratio=75; Ex12-6: 1.7=46/ratio=648; Ex13-4: 1.7=89/ratio=304; Ex13-5: 1.7=40/ratio=914; Ex13-6: 1.7=147/ratio=43; Ex14-4: 1.7=596/ratio=27; Ex15-5: 1.7=535/ratio=108; Ex15-6: 1.7=145/ratio=207; Ex16-8: 1.7=134/ratio=88; Ex17-4: 1.7=34/ratio=200;

Ex17-5: 1.7=24/ratio=310; Ex17-6: 1.7=12/ratio=178; Ex17-7: 1.7=49/ratio=147; Ex17-8: 1.7=6/ratio=1452; Ex18-3: 1.7=13/ratio=233; Ex18-6: 1.7=57/ratio=30; Ex18-7: 1.7=69/ratio=90; Ex18-8: 1.7=107/ratio=102; Ex19-1: 1.7=9/ratio=603; Ex19-2: 1.7=14/ratio=133; Ex19-3: 1.7=49/ratio=147; Ex19-5: 1.7=482/ratio=96; Ex19-11: 1.7=103/ratio=244; Ex19-12: 1.7=154/ratio=195; Ex20-1: 1.7=98/ratio=120; Ex20-2: 1.7=35/ratio=272; Ex20-3: 1.7=243/ratio=218; Ex21-1: 1.7=229/ratio=151; Ex21-2: 1.7=245/ratio=122; Ex21-3: 1.7=808/ratio=37; Ex21-4: 1.7=226/ratio=45; Ex21-5: 1.7=885/ratio=34; Ex21-6: 1.7=382/ratio=27; Ex21-7: 1.7=337/ratio=89; Ex21-9: 1.7=407/ratio=74; Ex21-10: 1.7=342/ratio=88; Ex21-11: 1.7=189/ratio=137; Ex21-12: 1.7=258/ratio=116; Ex21-13: 1.7=116/ratio=258; Ex21-14: 1.7=234/ratio=134; Ex21-15: 1.7=516/ratio=58; Ex21-17: 1.7=68/ratio=41; Ex21-18: 1.7=118/ratio=64; Ex21-20: 1.7=200/ratio=30; Ex21-21: 1.7=155/ratio=193; Ex21-22: 1.7=136/ratio=220; Ex21-23: 1.7=90/ratio=251; Ex21-24: 1.7=102/ratio=240; Ex21-25: 1.7=9/ratio=167; Ex21-26: 1.7=16/ratio=192; Ex21-27: 1.7=32/ratio=476; Ex22-1: 1.7=55/ratio=380; Ex22-2: 1.7=70/ratio=305; Ex22-3: 1.7=101/ratio=297; Ex22-4: 1.7=169/ratio=178; Ex23-1: 1.7=150/ratio=200; Ex23-2: 1.7=74/ratio=405; Ex24-2: 1.7=27/ratio=1097; Ex24-2: 1.7=18/ratio=263;

Those skilled in the art will recognize that the dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the Formula:

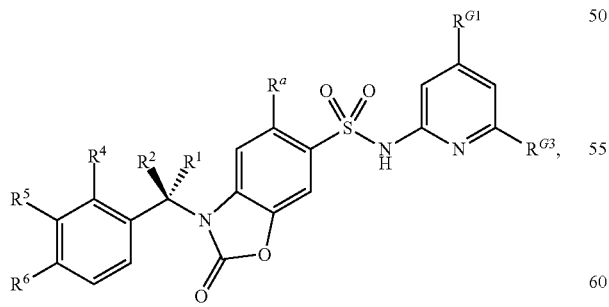

or a pharmaceutically acceptable salt thereof, wherein:
one of $R^1$ and $R^2$ is —H and the other is:
(i) —H;
(ii) —$C_{1-8}$ alkyl, wherein the alkyl moiety is optionally substituted with a $C_{3-6}$ cycloalkyl moiety;

$R^a$ is —H, $C_{1-6}$ alkyl, $C_{1-6}$ alkoxy, —CN or halogen;
one of $R^{G1}$ and $R^{G3}$ is —H and the other is —H or Halogen; and
$R^4$, $R^5$, and $R^6$ are independently:
(i) —H;
(ii) halogen;
(iii) linear $C_{1-8}$-alkyl, $C_{3-8}$-branched alkyl, $C_{3-8}$-cycloalkyl, $C_{2-8}$ alkenyl, or $C_{2-6}$ alkynyl, as these moieties are defined herein, which substituents may optionally be substituted by one or more moieties which are:
(a) halogen;
(b) hydroxyl;
(c) $C_{3-6}$-cycloalkyl substituted with an amino-moiety;
(d);
(e) $(R^{aa})_2N$-(J)-, wherein $R^{aa}$ is:
(1) independently for each occurrence —H or is $C_{1-6}$-linear alkyl or $C_{3-6}$-cycloalkyl;
(2) and wherein "J" is a moiety of the structure:

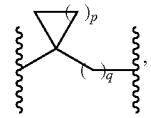

wherein "p" is an integer of 1 to 4 and "q" is an integer of 0 to 5;
(f) —$N(R^{ab})_2$, wherein $R^{ab}$ is: (1) independently for each occurrence —H or is $C_{1-6}$-linear alkyl or is $C_{3-6}$-cycloalkyl, which is optionally bonded to the ring through —$S(O_2)$— or —C(O)— moiety;
(iv).

2. A compound of claim 1, or a salt thereof, wherein:
$R^{G1}$ and $R^{G3}$ are selected to provide a moiety of Formula CA or CB:

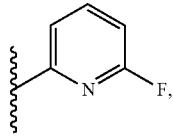

Formula CA

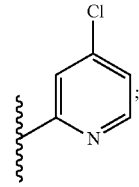

Formula CB and
one of $R^4$, $R^5$, and $R^6$ are —H, and the other two are independently for each occurrence:
(a) —H;
(b) halogen;
(c) $C_{1-8}$-alkyl, $C_{2-8}$ alkenyl, or $C_{2-6}$ alkynyl, which substituents may optionally be substituted by one or more moieties which are:
(i) halogen;
(ii) hydroxyl;

(iii) (R$^{aa}$)$_2$N-(J)-, wherein R$^{aa}$ is: (1) independently for each occurrence: —H; —SO$_2$C$_{1-8}$-alkyl; —SO$_2$-aryl; —(O=C)C$_{1-8}$-alkyl; C$_{1-6}$-linear alkyl-; or C$_{3-6}$-cycloalkyl-, and when R$^{aa}$ is selected to be an alkyl moiety it may be optionally substituted with one or more fluorine substituents, and wherein "J" is a moiety of the structure:

where "p" is an integer of 1 to 4 and "q" is an integer of 0 to 5;

(iv) —N(R$^{ab}$)$_2$, wherein R$^{ab}$ is: (1) independently for each occurrence: —H; —SO$_2$C$_{1-8}$-alkyl; —SO$_2$-aryl; —(O=C)C$_{1-8}$-alkyl; C$_{1-6}$-linear alkyl; or C$_{3-6}$-cycloalkyl and is optionally bonded to the ring through —S(O$_2$)— or —C(O)— moiety; or (v) C$_{1-6}$-alkoxy;

(d).

3. A compound of claim 1, or a salt thereof, wherein R$^6$ is —H.

4. A compound of claim 1, or a pharmaceutically acceptable salt thereof, which is:

3-{(1R)-1-[2-(4-aminocyclohex-1-en-1-yl)phenyl]ethyl}-5-fluoro-N-(6-fluoropyridin-2-yl)-2-oxo-2,3-dihydro-1,3-benzoxazole-6-sulfonamide;

3-{(1R)-1-[2-(3-aminoprop-1-yn-1-yl)phenyl]ethyl}-5-fluoro-N-(6-fluoropyridin-2-yl)-2-oxo-2,3-dihydro-1,3-benzoxazole-6-sulfonamide;

3-[(1R)-1-(2-{[(1R,2R)-2-aminocyclohexyl]ethynyl}phenyl)ethyl]-5-fluoro-N-(6-fluoropyridin-2-yl)-2-oxo-2,3-dihydro-1,3-benzoxazole-6-sulfonamide;

3-{(1R)-1-[2-(3-amino-4-hydroxybut-1-yn-1-yl)phenyl]ethyl}-5-fluoro-N-(6-fluoropyridin-2-yl)-2-oxo-2,3-dihydro-1,3-benzoxazole-6-sulfonamide;

3-[(1R)-1-(2-{[(1R,2S)-2-aminocyclohexyl]ethynyl}phenyl)ethyl]-5-fluoro-N-(6-fluoropyridin-2-yl)-2-oxo-2,3-dihydro-1,3-benzoxazole-6-sulfonamide;

3-[(1R)-1-{2-[(1-aminocyclohexyl)ethynyl]phenyl}ethyl]-5-fluoro-N-(6-fluoropyridin-2-yl)-2-oxo-2,3-dihydro-1,3-benzoxazole-6-sulfonamide;

3-{(1R)-1-[2-(4-amino-4-methylpent-1-yn-1-yl)phenyl]ethyl}-5-fluoro-N-(6-fluoropyridin-2-yl)-2-oxo-2,3-dihydro-1,3-benzoxazole-6-sulfonamide;

3-[(1R)-1-{2-[3-(dimethylamino)prop-1-yn-1-yl]phenyl}ethyl]-5-fluoro-N-(6-fluoropyridin-2-yl)-2-oxo-2,3-dihydro-1,3-benzoxazole-6-sulfonamide;

3-{(1R)-1-[2-(aminomethyl)phenyl]ethyl}-5-fluoro-N-(6-fluoropyridin-2-yl)-2-oxo-2,3-dihydro-1,3-benzoxazole-6-sulfonamide;

3-[(1R)-1-{2-[(dimethylamino)methyl]phenyl}ethyl]-5-fluoro-N-(6-fluoropyridin-2-yl)-2-oxo-2,3-dihydro-1,3-benzoxazole-6-sulfonamide;

3-[(1R)-1-(2-bromo-3-methylphenyl)ethyl]-5-fluoro-N-(6-fluoropyridin-2-yl)-2-oxo-2,3-dihydro-1,3-benzoxazole-6-sulfonamide;

3-{(1R)-1-[2-(aminomethyl)phenyl]ethyl}-N-(6-fluoropyridin-2-yl)-5-methyl-2-oxo-2,3-dihydro-1,3-benzoxazole-6-sulfonamide;

3-[(1R)-1-(2-bromophenyl)ethyl]-5-fluoro-N-(6-fluoropyridin-2-yl)-2-oxo-2,3-dihydro-1,3-benzoxazole-6-sulfonamide;

3-[(1R)-1-(3-bromophenyl)ethyl]-5-fluoro-N-(6-fluoropyridin-2-yl)-2-oxo-2,3-dihydro-1,3-benzoxazole-6-sulfonamide;

3-[(1R)-1-(3-bromophenyl)ethyl]-N-(6-fluoropyridin-2-yl)-5-methyl-2-oxo-2,3-dihydro-1,3-benzoxazole-6-sulfonamide;

3-[(1R)-1-(3-bromo-2-methylphenyl)ethyl]-N-(6-fluoropyridin-2-yl)-5-methyl-2-oxo-2,3-dihydro-1,3-benzoxazole-6-sulfonamide;

3-[(1R)-1-(2-bromo-3-methylphenyl)ethyl]-N-(6-fluoropyridin-2-yl)-5-methyl-2-oxo-2,3-dihydro-1,3-benzoxazole-6-sulfonamide;

3-[(1R)-1-(2-bromophenyl)ethyl]-N-(6-fluoropyridin-2-yl)-5-methyl-2-oxo-2,3-dihydro-1,3-benzoxazole-6-sulfonamide;

3-[(1R)-1-(3-bromo-2-methylphenyl)ethyl]-N-(6-fluoropyridin-2-yl)-5-fluoro-2-oxo-2,3-dihydro-1,3-benzoxazole-6-sulfonamide;

3-{(1R)-1-[2-(aminomethyl)-3-methylphenyl]ethyl}-5-fluoro-N-(6-fluoropyridin-2-yl)-2-oxo-2,3-dihydro-1,3-benzoxazole-6-sulfonamide;

3-{(1R)-1-[2-(aminomethyl)-3-methylphenyl]ethyl}-N-(6-fluoropyridin-2-yl)-5-methyl-2-oxo-2,3-dihydro-1,3-benzoxazole-6-sulfonamide;

3-{(1R)-1-[2-(aminomethyl)phenyl]ethyl}-N-(6-fluoropyridin-2-yl)-5-methyl-2-oxo-2,3-dihydro-1,3-benzoxazole-6-sulfonamide;

3-{(1R)-1-[3-(aminomethyl)-2-methylphenyl]ethyl}-5-fluoro-N-(6-fluoropyridin-2-yl)-2-oxo-2,3-dihydro-1,3-benzoxazole-6-sulfonamide;

3-{(1R)-1-[3-(aminomethyl)phenyl]ethyl}-5-fluoro-N-(6-fluoropyridin-2-yl)-2-oxo-2,3-dihydro-1,3-benzoxazole-6-sulfonamide;

3-[(1R)-1-{3-[(dimethylamino)methyl]phenyl}ethyl]-5-fluoro-N-(6-fluoropyridin-2-yl)-2-oxo-2,3-dihydro-1,3-benzoxazole-6-sulfonamide;

3-[(1R)-1-{3-[(tert-butylamino)methyl]phenyl}ethyl]-5-fluoro-N-(6-fluoropyridin-2-yl)-2-oxo-2,3-dihydro-1,3-benzoxazole-6-sulfonamide;

3-{(1R)-1-[3-(2-aminoethyl)phenyl]ethyl}-5-fluoro-N-(6-fluoropyridin-2-yl)-2-oxo-2,3-dihydro-1,3-benzoxazole-6-sulfonamide;

3-{(1R)-1-[3-(2-aminoethyl)-2-methylphenyl]ethyl}-5-fluoro-N-(6-fluoropyridin-2-yl)-2-oxo-2,3-dihydro-1,3-benzoxazole-6-sulfonamide;

3-{(1R)-1-[3-(3-amino-3-methylbut-1-yn-1-yl)phenyl]ethyl}-5-fluoro-N-(6-fluoropyridin-2-yl)-2-oxo-2,3-dihydro-1,3-benzoxazole-6-sulfonamide;

5-fluoro-N-(6-fluoropyridin-2-yl)-3-[(1R)-1-{3-[3-(methylamino)prop-1-yn-1-yl]phenyl}ethyl]-2-oxo-2,3-dihydro-1,3-benzoxazole-6-sulfonamide;

3-[(1R)-1-{3-[3-(dimethylamino)prop-1-yn-1-yl]phenyl}ethyl]-5-fluoro-N-(6-fluoropyridin-2-yl)-2-oxo-2,3-dihydro-1,3-benzoxazole-6-sulfonamide;

3-[(1R)-1-{3-[(1-aminocyclohexyl)ethynyl]phenyl}ethyl]-5-fluoro-N-(6-fluoropyridin-2-yl)-2-oxo-2,3-dihydro-1,3-benzoxazole-6-sulfonamide;

3-{(1R)-1-[3-(3-aminobut-1-yn-1-yl)phenyl]ethyl}-5-fluoro-N-(6-fluoropyridin-2-yl)-2-oxo-2,3-dihydro-1,3-benzoxazole-6-sulfonamide;

3-[(1R)-1-{3-[3-(cyclohexylamino)prop-1-yn-1-yl]phenyl}ethyl]-5-fluoro-N-(6-fluoropyridin-2-yl)-2-oxo-2,3-dihydro-1,3-benzoxazole-6-sulfonamide;

3-[(1R)-1-{3-[(1-aminocyclopropyl)ethynyl]phenyl}ethyl]-5-fluoro-N-(6-fluoropyridin-2-yl)-2-oxo-2,3-dihydro-1,3-benzoxazole-6-sulfonamide;

3-[(1R)-1-{3-[3-(diethylamino)prop-1-yn-1-yl]phenyl}ethyl]-5-fluoro-N-(6-fluoropyridin-2-yl)-2-oxo-2,3-dihydro-1,3-benzoxazole-6-sulfonamide;

3-[(1R)-1-(3-{[(1S,2S)-2-aminocyclohexyl]ethynyl}phenyl)ethyl]-5-fluoro-N-(6-fluoropyridin-2-yl)-2-oxo-2,3-dihydro-1,3-benzoxazole-6-sulfonamide;

3-[(1R)-1-{3-[(2-aminocyclopentyl)ethynyl]phenyl}ethyl]-5-fluoro-N-(6-fluoropyridin-2-yl)-2-oxo-2,3-dihydro-1,3-benzoxazole-6-sulfonamide;

3-{(1R)-1-[3-(3-aminoprop-1-yn-1-yl)phenyl]ethyl}-5-fluoro-N-(6-fluoropyridin-2-yl)-2-oxo-2,3-dihydro-1,3-benzoxazole-6-sulfonamide;

3-{(1R)-1-[3-(3-aminoprop-1-yn-1-yl)-2-methylphenyl]ethyl}-5-fluoro-N-(6-fluoropyridin-2-yl)-2-oxo-2,3-dihydro-1,3-benzoxazole-6-sulfonamide;

3-{(1R)-1-[3-(3-aminoprop-1-yn-1-yl)phenyl]ethyl}-N-(6-fluoropyridin-2-yl)-5-methyl-2-oxo-2,3-dihydro-1,3-benzoxazole-6-sulfonamide;

3-{(1R)-1-[3-(3-aminoprop-1-yn-1-yl)-2-methylphenyl]ethyl}-N-(6-fluoropyridin-2-yl)-5-methyl-2-oxo-2,3-dihydro-1,3-benzoxazole-6-sulfonamide;

3-[(1R)-1-(2-{[(1S,2S)-2-aminocyclohexyl]ethynyl}-3-methylphenyl)ethyl]-N-(6-fluoropyridin-2-yl)-5-methyl-2-oxo-2,3-dihydro-1,3-benzoxazole-6-sulfonamide;

3-[(1R)-1-(2-{[(1R,2R)-2-aminocyclohexyl]ethynyl}-3-methylphenyl)ethyl]-N-(6-fluoropyridin-2-yl)-5-methyl-2-oxo-2,3-dihydro-1,3-benzoxazole-6-sulfonamide;

3-[(1R)-1-(2-{[(1S,2S)-2-aminocyclohexyl]ethynyl}-3-methylphenyl)ethyl]-5-fluoro-N-(6-fluoropyridin-2-yl)-2-oxo-2,3-dihydro-1,3-benzoxazole-6-sulfonamide;

3-{(1R)-1-[3-(3-aminopropyl)phenyl]ethyl}-5-fluoro-N-(6-fluoropyridin-2-yl)-2-oxo-2,3-dihydro-1,3-benzoxazole-6-sulfonamide;

3-{(1R)-1-[3-(3-amino-propyl)phenyl]ethyl}-N-(6-fluoropyridin-2-yl)-5-methyl-2-oxo-2,3-dihydro-1,3-benzoxazole-6-sulfonamide;

3-{(1R)-1-[3-(3-amino-propyl)-2-methylphenyl]ethyl}-5-fluoro-N-(6-fluoropyridin-2-yl)-2-oxo-2,3-dihydro-1,3-benzoxazole-6-sulfonamide;

3-{(1R)-1-[2-(2-aminoethyl)phenyl]ethyl}-5-fluoro-N-(6-fluoropyridin-2-yl)-2-oxo-2,3-dihydro-1,3-benzoxazole-6-sulfonamide; or 3-{(1R)-1-[2-(2-aminoethyl)-3-methylphenyl]-ethyl}-5-fluoro-N-(6-fluoropyridin-2-yl)-2-oxo-2,3-dihydro-1,3-benzoxazole-6-sulfonamide.

5. A pharmaceutical composition comprising at least one compound of claim 4 or a pharmaceutically acceptable salt thereof, and at least one excipient.

* * * * *